US011047855B2

(12) United States Patent
Sorek et al.

(10) Patent No.: US 11,047,855 B2
(45) Date of Patent: Jun. 29, 2021

(54) DIAGNOSIS OF SYSTEMIC LUPUS ERYTHEMATOSUS USING PROTEIN, PEPTIDE AND OLIGONUCLEOTIDE ANTIGENS

(71) Applicants: IMMUNARRAY LTD., Rehovot Tel Aviv (IL); YEDA RESEARCH AND DEVELOPMENT CO. LTD., Rehovot (IL)

(72) Inventors: Rachel Sorek, Zafaria (IL); Keren Jakobi, Reut-Maccabim (IL); Pennina Safer, Rechovot (IL); Anat Reiner-Benaim, Binyamina (IL); Irun R. Cohen, Rehovot (IL)

(73) Assignees: IMMUNARRAY LTD., Rehovot Tel Aviv (IL); YEDA RESEARCH AND DEVELOPMENT CO. LTD., Rehovot (IL)

( * ) Notice: Subject to any disclaimer, the term of this patent is extended or adjusted under 35 U.S.C. 154(b) by 0 days.

(21) Appl. No.: 15/555,258

(22) PCT Filed: Feb. 29, 2016

(86) PCT No.: PCT/IL2016/050229
§ 371 (c)(1),
(2) Date: Sep. 1, 2017

(87) PCT Pub. No.: WO2016/139659
PCT Pub. Date: Sep. 9, 2016

(65) Prior Publication Data
US 2018/0238873 A1 Aug. 23, 2018

Related U.S. Application Data

(60) Provisional application No. 62/126,616, filed on Mar. 1, 2015, provisional application No. 62/181,231, filed on Jun. 18, 2015, provisional application No. 62/249,284, filed on Nov. 1, 2015.

(51) Int. Cl.
*G01N 33/564* (2006.01)
*G01N 33/68* (2006.01)
*G16B 40/00* (2019.01)

(52) U.S. Cl.
CPC ....... *G01N 33/564* (2013.01); *G01N 33/6854* (2013.01); *G01N 2800/104* (2013.01); *G16B 40/00* (2019.02)

(58) Field of Classification Search
CPC ............. G01N 33/564; G01N 33/6854; G01N 2800/104; G16B 40/00
See application file for complete search history.

(56) References Cited

U.S. PATENT DOCUMENTS

| | | |
|---|---|---|
| 3,849,550 A | 11/1974 | Teitelbaum et al. |
| 4,208,479 A | 6/1980 | Zuk et al. |
| 5,114,844 A | 5/1992 | Cohen et al. |
| 5,326,357 A | 7/1994 | Kandel |
| 5,578,303 A | 11/1996 | Cohen et al. |
| 5,671,848 A | 9/1997 | Cohen et al. |
| 5,700,641 A | 12/1997 | Salonen |
| 5,763,158 A | 6/1998 | Bohannon |
| 5,780,034 A | 7/1998 | Cohen et al. |
| 5,800,808 A | 9/1998 | Konfino et al. |
| 5,858,804 A | 1/1999 | Zanzucchi et al. |
| 5,981,700 A | 11/1999 | Rabin |
| 6,048,898 A | 4/2000 | Konfino et al. |
| 6,054,430 A | 4/2000 | Konfino et al. |
| 7,276,341 B2 | 10/2007 | Harley et al. |
| 7,476,514 B2 | 1/2009 | Britz et al. |
| 2003/0003516 A1 | 1/2003 | Robinson et al. |
| 2003/0087848 A1 | 5/2003 | Bratzler et al. |
| 2004/0014069 A1 | 1/2004 | Cohen et al. |
| 2005/0260770 A1 | 11/2005 | Cohen et al. |
| 2007/0141627 A1 | 6/2007 | Behrens et al. |
| 2008/0254482 A1 | 10/2008 | Mattoon et al. |
| 2008/0293660 A1 | 11/2008 | Coutts et al. |
| 2009/0246195 A1 | 10/2009 | Tedder |
| 2010/0160415 A1 | 6/2010 | Solvason et al. |
| 2011/0312016 A1 | 12/2011 | Pankewycz et al. |
| 2012/0077689 A1 | 3/2012 | Sarwal et al. |
| 2013/0183686 A1 | 7/2013 | Pankewycz et al. |

FOREIGN PATENT DOCUMENTS

| | | |
|---|---|---|
| CN | 1954216 A | 4/2007 |
| CN | 101329341 A | 12/2008 |
| EP | 0 417 271 B1 | 3/1991 |
| EP | 1 630 557 A1 | 3/2006 |
| EP | 2 336 769 A1 | 6/2011 |
| GB | 2460717 A | 12/2009 |
| JP | 2005-509127 A | 4/2005 |
| WO | 99/39210 A1 | 8/1999 |

(Continued)

OTHER PUBLICATIONS

Merbi et al., (2007) Newborn humans manifest autoantibodies to defined self molecules detected by antigen microarray informatics. Journal of Clinical Investigation, 117(3), 712-718.
Mor et al., (1996) IL-2 and TNF receptors as targets of regulatory T-T interactions: isolation and characterization of cytokine receptor-reactive T cell lines in the Lewis rat. J Immunol 157(11): 4855-4861.
Moreland et al., (1991) Collagen autoantibodies in patients with vasculitis and systemic lupus erythematosus. Clin Immunol Immunopathol 60(3): 412-418.
Nahon et al., (1982) Anti-poly (G)•poly (C) antibodies in the serum of patients with systemic lupus erythematosus. Clinical immunology and immunopathology, 22(3), 349-362.

(Continued)

*Primary Examiner* — Olga N Chernyshev
(74) *Attorney, Agent, or Firm* — J.A. Lindeman & Co., PLLC

(57) ABSTRACT

Methods and kits for diagnosing or monitoring systemic lupus erythematosus (SLE) in a subject are provided. Particularly, provided is a specific antibody reactivity profile useful in diagnosing or monitoring SLE in a subject.

3 Claims, 13 Drawing Sheets

Specification includes a Sequence Listing.

(56) References Cited

FOREIGN PATENT DOCUMENTS

| | | |
|---|---|---|
| WO | 01/82960 A1 | 11/2001 |
| WO | 02/08755 A2 | 1/2002 |
| WO | 2008/082730 A2 | 7/2008 |
| WO | 2010/055510 A2 | 5/2010 |
| WO | 2010/128506 A2 | 11/2010 |
| WO | 2011/099012 A1 | 8/2011 |
| WO | 2012/052994 A2 | 4/2012 |
| WO | 2013/022995 A2 | 2/2013 |
| WO | 2014/091490 A2 | 6/2014 |
| WO | 2014/195730 A2 | 12/2014 |
| WO | 2015/101987 A1 | 7/2015 |
| WO | 2015/101988 A1 | 7/2015 |
| WO | 2017/025954 A1 | 2/2017 |

OTHER PUBLICATIONS

Niller et al., (2008) Regulation and dysregulation of Epstein-Barr virus latency: implications for the development of autoimmune diseases. Autoimmonity 41(4): 298-328.

Oliva et al., (1998) Automated classification of antibody complementarity determining region 3 of the heavy chain (H3) loops into canonical forms and its application to protein structure prediction. J Mol Biol 279(5): 1193-210, pp. 1193-1194.

Pal et al., (2000) Identification and purification of cytolytic antibodies directed against O-acetylated sialic acid in childhood acute lymphoblastic leukemia. Glycobiology 10(6): 539-549.

Park, (2001) Primary structures and chain dominance of anti-DNA antibodies. Molecules & Cells (Springer Science & Business Media BV), 11(1), pp. 55-63.

Pavlovic et al., (2010) Pathogenic and Epiphenomenal Anti-DNA Antibodies in SLE. Autoimmune diseases, 462841, 18 pages.

Peng et al., (2005) Toll-like receptor 8-mediated reversal of CD4+ regulatory T cell function. Science, 309(5739), 1380-1384.

Petri et al., (1991) Morbidity of systemic lupus erythematosus: role of race and socioeconomic status. The American journal of medicine, 91(4), 345-353.

Petri et al., (2012) Derivation and validation of the Systemic Lupus International Collaborating Clinics classification criteria for systemic lupus erythematosus. Arthritis & Rheumatology, 64(8), 2677-2686.

Putterman et al., (2016) SLE-key® rule-out serologic test for excluding the diagnosis of systemic lupus erythematosus: Developing the ImmunArray iCHIP®. Journal of immunological methods, 429, 1-6.

Quintana et al., (2001) Autoantibody patterns in diabetes-prone NOD mice and in standard C57BL/6 mice. Journal of autoimmunity, 17(3), 191-197.

Quintana et al., (2003) Cluster analysis of human autoantibody reactivities in health and in type 1 diabetes mellitus: a bioinformatic approach to immune complexity. Journal of autoimmunity, 21(1), 65-75.

Quintana et al., (2004) Functional immunomics: microarray analysis of IgG autoantibody repertoires predicts the future response of mice to induced diabetes. Proceedings of the National Academy of Sciences, 101(suppl 2), 14615-14621.

Quintana et al., (2006) Antigen-chip technology for accessing global information about the state of the body. Lupus, 15(7), 428-430.

Quintana et al., (2008) Antigen microarrays identify unique serum autoantibody signatures in clinical and pathologic subtypes of multiple sclerosis. Proc Natl Acad Sci USA 105(48): 18889-18894.

Robinson et al., (2002) Autoantigen microarrays for multiplex characterization of autoantibody responses. Nature medicine, 8(3), 295-301.

Robinson et al., (2003) Protein microarrays guide tolerizing DNA vaccine treatment of autoimmune encephalomyelitis. Nature biotechnology, 21(9), 1033-1039.

Sen et al. (2003) Antineutrophil cytoplasmic autoantibodies in systemic lupus erythematosus. Lupus 12(9): 651-658.

Sherer et al., (2004) Autoantibody explosion in systemic lupus erythematosus: more than 100 different antibodies found in SLE patients. In Seminars in arthritis and rheumatism (vol. 34, No. 2, pp. 501-537). WB Saunders.

Sternbaek et al., (2017) Efficient evaluation of humoral immune responses by the use of serum pools. Journal of Immunological Methods, 443, 1-8.

Tan et al., (1982) The 1982 revised criteria for the classification of systemic lupus erythematosus. Arthritis & Rheumatology, 25(11), 1271-1277.

Toussirot et al., (2008) Epstein-Barr virus in autoimmune diseases. Best Pract Res Clin Rheumatol 22(5): 883-896.

Vincenti et al., (2010) A phase III study of belatacept-based immunosuppression regimens versus cyclosporine in renal transplant recipients (BENEFIT study). American Journal of Transplantation, 10(3), 535-546.

Wold et al., (1968) Deoxyribonucleic acid antibody: A method to detect its primary interaction with deoxyribonucleic acid. Science 161(3843): 806-807.

Zagorodniuk et al., (2005) A comparison of anti-desmoglein antibodies and indirect immunofluorescence in the serodiagnosis of pemphigus vulgaris. International journal of dermatology, 44(7), 541-544.

Zhen et al., (2005) Identification of autoantibody clusters that best predict lupus disease activity using glomerular proteome arrays. J Clin Invest 115(12): 3428-3439.

Hawro et al., (2015) "Serum neuron specific enolase—a novel indicator for neuropsychiatric systemic lupus erythematosus?", Lupus 24(14): 1492-1497.

Lin et al., (2013) "An antibody-based leukocyte-capture microarray for the diagnosis of systemic lupus erythematosus", PLoS One 8(3): e58199; 8 pages.

Ronnefarth, "Dissertation, The Role of Nucleosome-Induced Neutrophil Activation in Systemic Lupus Erythmatosus" The Eberhard Karls University of Tubingen, Germany 2007, 1-78.

Swissa et al., (1990) "Autoantibodies in neoplasia. An unresolved enigma", Cancer 65(11): 2554-2558.

Swissa et al., (1991) "Determination of autoantibodies in patients with familial Mediterranean fever and their first degree relatives", J Rheumatol 18(4): 606-608.

To et al., (2011) "Plasma and cellular fibronectin: distinct and independent functions during tissue repair", Fibrogenesis Tissue Repair 4: 21; 17 pages.

Abulafia-Lapid et al., (1999) T cell proliferative responses of type 1 diabetes patients and healthy individuals to human hsp60 and its peptides. J Autoimmun 12(2): 121-129.

Abulafia-Lapid et al., (2003) T cells and autoantibodies to human HSP70 in type 1 diabetes in children. J Autoimmun 20(4): 313-321.

Abu-Shakra et al., (1995) Mortality studies in systemic lupus erythematosus. Results from a single center. I. Causes of death. The Journal of Rheumatology, 22(7), 1259-1264.

Alon et al., (1999) Broad patterns of gene expression revealed by clustering analysis of tumor and normal colon issues probed by oligonucleotide arrays. Proc Natl Acad Sci U S A 96(12): 6745-6750.

Barzilai et al., (2007) Epstein-Barr virus and cytomegalovirus in autoimmune diseases: are they truly notorious? A preliminary report. Ann N Y Acad Sci 1108(1): 567-577.

Batstra et al., (2001) Prediction and diagnosis of type 1 diabetes using beta-cell autoantibodies. Clin Lab 47(9-10): 497-507, abstract.

Cahill (2000) Protein arrays: a high-throughput solution for proteomics research? Trends in Biotechnology 18: 47-51.

Cavallo et al., (2012) A Novel Method for Real-Time, Continuous, Fluorescence-Based Analysis of Anti-DNA Abzyme Activity in Systemic Lupus. Autoimmune diseases, 814048, 10 pages.

Chagnon et al., (2006) Identification and characterization of an Xp22.33;Yp11.2 translocation causing a triplication of several genes of the pseudoautosomal region 1 in an XX male patient with severe systemic lupus erythematosus. Arthritis Rheum 54(4): 1270-1278.

Cohen, (2007) Real and artificial immune systems: computing the state of the body. Nature Reviews Immunology, 7(7) : 569-574.

(56) References Cited

OTHER PUBLICATIONS

Diaz-Quijada et al., (2004) A simple approach to micropatterning and surface modification of poly(dimethylsiloxane). Langmuir, 20(22), 9607-9611.

Domany (1999) Superparamagnetic clustering of data—The definitive solution of an ill-posed problem. Physica A: Statistical Mechanics and its Applications 263(1-4): 158-169, pp. 166-168.

Eisen et al., (1998) Cluster analysis and display of genome-wide expression patterns. Proc Natl Acad Sci U S A 95(25): 14863-14868.

Elizur, Thesis, Antigen Chip: Development and Analysis; An Application to Autoimmune Diseases, The Weizmann Institute of Science, Israel, Jan. 2004, 1-78.

Esen et al., (2012) Serologic response to Epstein-Barr virus antigens in patients with systemic lupus erythematosus: a controlled study. Rheumatol Int 32(1): 79-83.

Faaber et al.,(1984) Cross-reactivity of anti-DNA antibodies with proteoglycans. Clin Exp Immunol 55(3): 502-508.

Fattal et al., (2010) an antibody profile of systemic lupus erythematosus detected by antigen microarray. Immunology, 130(3), 337-343.

Fattal et al., (2015) Guanine polynucleotides are self-antigens for human natural autoantibodies and are significantly reduced in the human genome. Immunology, 146(3), 401-410.

Ferreira et al., (1997) Instability of natural antibody repertoires in systemic lupus erythematosus patients, revealed by multiparametric analysis of serum antibody reactivities. Scand J Immunol 45(3): 331-341.

Fraley et al., (1998) How many clusters? Which clustering method? Answers via model-based cluster analysis. Technical report No. 329, Department of Statistics, University of Washington, Seattle, WA, P.I, 1-19.

Getz et al., (2000) Coupled two-way clustering analysis of gene microarray data. Proc Natl Acad Sci U S A 97(22): 12079-12084.

Golub et al., (1999) Molecular classification of cancer: class discovery and class prediction by gene expression monitoring. Science 286(5439): 531-537.

Grus et al., (1998) Diagnostic classification of autoantibody repertoires in endocrine ophthalmopathy using an artificial neural network. Ocular immunology and inflammation, 6(1), 43-50.

Hanly et al., (2010) Measurement of autoantibodies using multiplex methodology in patients with systemic lupus erythematosus. Journal of immunological methods, 352(1), 147-152.

Harley et al. (2006) Epstein-Barr virus infection induces lupus autoimmunity. Bull NYU Hosp Jt Dis 64(1-2): 45-50.

Herkel et al., (2001) Autoimmunity to the p53 protein is a feature of systemic lupus erythematosus (SLE) related to anti-DNA antibodies. J Autoimmun 17(1): 63-69.

Herkel et al., (2004) Monoclonal antibody to a DNA-binding domain of p53 mimics charge structure of DNA: anti-diotypes to the anti-p53 antibody are anti-DNA. European journal of immunology, 34(12), 3623-3632.

Hochberg, (1997) Updating the American College of Rheumatology revised criteria for the classification of systemic lupus erythematosus. Arthritis & Rheumatism, 40(9), 1725-1725.

Invitrogen, HuProtV2 array, 2007. 2 pages.

Isenberg et al., (1986) The relationship of anti-DNA antibody idiotypes and anti-cardiolipin antibodies to disease activity in systemic lupus erythematosus. Medicine (Baltimore) 65(1): 46-55.

Ito et al., (1992) Cell proliferation in childhood acute leukemia. Comparison of Ki-67 and proliferating cell nuclear antigen immunocytochemical and DNA flow cytometric analysis. Cancer 69(8): 2176-2182.

James et al., (2012) Lupus and epstein-barr. Current opinion in rheumatology, 24(4), 383-388.

James et al., (1997) An increased prevalence of Epstein-Barr virus infection in young patients suggests a possible etiology for systemic lupus erythematosus. J Clin Invest 100(12): 3019-3026.

Joos et al., (2000) A microarray enzyme-linked immunosorbent assay for autoimmune diagnostics. Electrophoresis 21(13): 2641-2650.

Kang et al., (2004) Defective control of latent Epstein-Barr virus infection in systemic lupus erythematosus. J Immunol 172(2): 1287-1294.

Kanter et al., (2006) Lipid microarrays identify key mediators of autoimmune brain inflammation. Nature medicine, 12(1), 138-143.

Khoshnoodi et al., (2008) Mammalian collagen IV. Microsc Res Tech 71(5): 357-370.

Kobayashi et al., (2013) Oligodeoxynucleotides expressing polyguanosine motifs promote antitumor activity through the upregulation of IL-2. The Journal of Immunology, 190(4), 1882-1889.

Koffler et al., (1971) Antibodies to polynucleotides in human sera: antigenic specificity and relation to disease. The Journal of experimental medicine, 134(1), 294-312.

Könen-Waisman et al., (1995) Self and foreign 60-kilodalton heat shock protein T cell epitope peptides serve as immunogenic carriers for a T cell-independent sugar antigen. J Immunol 154(11): 5977-5985.

Kupinski et al., (1999) Multiobjective genetic optimization of diagnostic classifiers with implications for generating receiver operating characteristic curves. IEEE Transactions on Medical Imaging, 18(8), 675-685.

Lenert, (2010) Nucleic acid sensing receptors in systemic lupus erythematosus: development of novel DNA-and/or RNA-like analogues for treating lupus. Clinical & Experimental Immunology, 161(2), 208-222.

Li et al., (2007) Protein array autoantibody profiles for insights into systemic lupus erythematosus and incomplete lupus syndromes. Clinical & Experimental Immunology, 147(1), 60-70.

Liang et al., (1989) Reliability and validity of six systems for the clinical assessment of disease activity in systemic lupus erythematosus. Arthritis & Rheumatology, 32(9), 1107-1118.

Lieberman et al., (2003) A comprehensive guide to antibody and T-cell responses in type 1 diabetes. Tissue Antigens 62(5): 359-377.

Lossos et al., (1998) Anticardiolipin antibodies in acute myeloid leukemia: prevalence and clinical significance. Am J Hematol 57(2): 139-143.

Love et al. (1990) Antiphospholipid antibodies: anticardiolipin and the lupus anticoagulant in systemic lupus erythematosus (SLE) and in non-SLE disorders. Prevalence and clinical significance. Ann Intern Med 112(9): 682-698.

Manolova et al., (2002) Predominance of IgG1 and IgG3 subclasses of autoantibodies to neutrophil cytoplasmic antigens in patients with systemic lupus erythematosus. Rheumatol Int 21(6): 227-233.

Masi, (1980) Preliminary criteria for the classification of systemic sclerosis (scleroderma). Arthritis & Rheumatism, 23(5), 581-590.

Mattoon et al., (2007) Biomarker Discovery: Immune Response Profiling on ProtoArray® Human Protein Microarrays. 1-6.

SEQUENCE LISTING

```
<160> NUMBER OF SEQ ID NOS: 42

<210> SEQ ID NO 1
<211> LENGTH: 282
<212> TYPE: PRT
<213> ORGANISM: Homo sapiens

<400> SEQUENCE: 1

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
    130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
    210                 215                 220

Thr Ala Thr Pro Thr His Cys Ala Tyr Asp Arg Ile Val Val Ala Gly
225                 230                 235                 240
```

```
Met Leu Leu Arg Gly Ala Val Val Pro Asp Ser Ala Leu Pro Phe Asn
            245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
            275                 280

<210> SEQ ID NO 2
<211> LENGTH: 1466
<212> TYPE: PRT
<213> ORGANISM: Homo sapiens

<400> SEQUENCE: 2

Met Met Ser Phe Val Gln Lys Gly Ser Trp Leu Leu Leu Ala Leu Leu
1               5                   10                  15

His Pro Thr Ile Ile Leu Ala Gln Gln Glu Ala Val Glu Gly Gly Cys
            20                  25                  30

Ser His Leu Gly Gln Ser Tyr Ala Asp Arg Asp Val Trp Lys Pro Glu
        35                  40                  45

Pro Cys Gln Ile Cys Val Cys Asp Ser Gly Ser Val Leu Cys Asp Asp
    50                  55                  60

Ile Ile Cys Asp Asp Gln Glu Leu Asp Cys Pro Asn Pro Glu Ile Pro
65                  70                  75                  80

Phe Gly Glu Cys Cys Ala Val Cys Pro Gln Pro Pro Thr Ala Pro Thr
                85                  90                  95

Arg Pro Pro Asn Gly Gln Gly Pro Gln Gly Pro Lys Gly Asp Pro Gly
            100                 105                 110

Pro Pro Gly Ile Pro Gly Arg Asn Gly Asp Pro Gly Ile Pro Gly Gln
        115                 120                 125

Pro Gly Ser Pro Gly Ser Pro Gly Pro Pro Gly Ile Cys Glu Ser Cys
    130                 135                 140

Pro Thr Gly Pro Gln Asn Tyr Ser Pro Gln Tyr Asp Ser Tyr Asp Val
145                 150                 155                 160

Lys Ser Gly Val Ala Val Gly Gly Leu Ala Gly Tyr Pro Gly Pro Ala
                165                 170                 175

Gly Pro Pro Gly Pro Pro Gly Pro Pro Gly Thr Ser Gly His Pro Gly
            180                 185                 190

Ser Pro Gly Ser Pro Gly Tyr Gln Gly Pro Pro Gly Glu Pro Gly Gln
        195                 200                 205

Ala Gly Pro Ser Gly Pro Pro Gly Pro Pro Gly Ala Ile Gly Pro Ser
    210                 215                 220

Gly Pro Ala Gly Lys Asp Gly Glu Ser Gly Arg Pro Gly Arg Pro Gly
225                 230                 235                 240

Glu Arg Gly Leu Pro Gly Pro Pro Gly Ile Lys Gly Pro Ala Gly Ile
                245                 250                 255

Pro Gly Phe Pro Gly Met Lys Gly His Arg Gly Phe Asp Gly Arg Asn
            260                 265                 270

Gly Glu Lys Gly Glu Thr Gly Ala Pro Gly Leu Lys Gly Glu Asn Gly
        275                 280                 285

Leu Pro Gly Glu Asn Gly Ala Pro Gly Pro Met Gly Pro Arg Gly Ala
    290                 295                 300

Pro Gly Glu Arg Gly Arg Pro Gly Leu Pro Gly Ala Ala Gly Ala Arg
305                 310                 315                 320

Gly Asn Asp Gly Ala Arg Gly Ser Asp Gly Gln Pro Gly Pro Pro Gly
```

-continued

```
                    325                 330                 335
Pro Pro Gly Thr Ala Gly Phe Pro Gly Ser Pro Gly Ala Lys Gly Glu
                340                 345                 350
Val Gly Pro Ala Gly Ser Pro Gly Ser Asn Gly Ala Pro Gly Gln Arg
                355                 360                 365
Gly Glu Pro Gly Pro Gln Gly His Ala Gly Ala Gln Gly Pro Pro Gly
                370                 375                 380
Pro Pro Gly Ile Asn Gly Ser Pro Gly Gly Lys Gly Glu Met Gly Pro
385                 390                 395                 400
Ala Gly Ile Pro Gly Ala Pro Gly Leu Met Gly Ala Arg Gly Pro Pro
                405                 410                 415
Gly Pro Ala Gly Ala Asn Gly Ala Pro Gly Leu Arg Gly Gly Ala Gly
                420                 425                 430
Glu Pro Gly Lys Asn Gly Ala Lys Gly Glu Pro Gly Pro Arg Gly Glu
                435                 440                 445
Arg Gly Glu Ala Gly Ile Pro Gly Val Pro Gly Ala Lys Gly Glu Asp
                450                 455                 460
Gly Lys Asp Gly Ser Pro Gly Glu Pro Gly Ala Asn Gly Leu Pro Gly
465                 470                 475                 480
Ala Ala Gly Glu Arg Gly Ala Pro Gly Phe Arg Gly Pro Ala Gly Pro
                485                 490                 495
Asn Gly Ile Pro Gly Glu Lys Gly Pro Ala Gly Glu Arg Gly Ala Pro
                500                 505                 510
Gly Pro Ala Gly Pro Arg Gly Ala Ala Gly Glu Pro Gly Arg Asp Gly
                515                 520                 525
Val Pro Gly Gly Pro Gly Met Arg Gly Met Pro Gly Ser Pro Gly Gly
                530                 535                 540
Pro Gly Ser Asp Gly Lys Pro Gly Pro Pro Gly Ser Gln Gly Glu Ser
545                 550                 555                 560
Gly Arg Pro Gly Pro Pro Gly Pro Ser Gly Pro Arg Gly Gln Pro Gly
                565                 570                 575
Val Met Gly Phe Pro Gly Pro Lys Gly Asn Asp Gly Ala Pro Gly Lys
                580                 585                 590
Asn Gly Glu Arg Gly Gly Pro Gly Gly Pro Gly Pro Gln Gly Pro Pro
                595                 600                 605
Gly Lys Asn Gly Glu Thr Gly Pro Gln Gly Pro Pro Gly Pro Thr Gly
                610                 615                 620
Pro Gly Gly Asp Lys Gly Asp Thr Gly Pro Pro Gly Pro Gln Gly Leu
625                 630                 635                 640
Gln Gly Leu Pro Gly Thr Gly Gly Pro Pro Gly Glu Asn Gly Lys Pro
                645                 650                 655
Gly Glu Pro Gly Pro Lys Gly Asp Ala Gly Ala Pro Gly Ala Pro Gly
                660                 665                 670
Gly Lys Gly Asp Ala Gly Ala Pro Gly Glu Arg Gly Pro Pro Gly Leu
                675                 680                 685
Ala Gly Ala Pro Gly Leu Arg Gly Gly Ala Gly Pro Pro Gly Pro Glu
                690                 695                 700
Gly Gly Lys Gly Ala Ala Gly Pro Pro Gly Pro Pro Gly Ala Ala Gly
705                 710                 715                 720
Thr Pro Gly Leu Gln Gly Met Pro Gly Glu Arg Gly Gly Leu Gly Ser
                725                 730                 735
Pro Gly Pro Lys Gly Asp Lys Gly Glu Pro Gly Gly Pro Gly Ala Asp
                740                 745                 750
```

-continued

Gly Val Pro Gly Lys Asp Gly Pro Arg Gly Thr Gly Pro Ile Gly
              755                 760                 765

Pro Pro Gly Pro Ala Gly Gln Pro Gly Asp Lys Gly Glu Gly Gly Ala
        770                 775                 780

Pro Gly Leu Pro Gly Ile Ala Gly Pro Arg Gly Ser Pro Gly Glu Arg
785                 790                 795                 800

Gly Glu Thr Gly Pro Pro Gly Pro Ala Gly Phe Pro Gly Ala Pro Gly
                805                 810                 815

Gln Asn Gly Glu Pro Gly Gly Lys Gly Glu Arg Gly Ala Pro Gly Glu
                820                 825                 830

Lys Gly Glu Gly Gly Pro Pro Gly Val Ala Gly Pro Pro Gly Gly Ser
                835                 840                 845

Gly Pro Ala Gly Pro Pro Gly Pro Gln Gly Val Lys Gly Glu Arg Gly
                850                 855                 860

Ser Pro Gly Gly Pro Gly Ala Ala Gly Phe Pro Gly Ala Arg Gly Leu
865                 870                 875                 880

Pro Gly Pro Pro Gly Ser Asn Gly Asn Pro Gly Pro Pro Gly Pro Ser
                885                 890                 895

Gly Ser Pro Gly Lys Asp Gly Pro Pro Gly Pro Ala Gly Asn Thr Gly
                900                 905                 910

Ala Pro Gly Ser Pro Gly Val Ser Gly Pro Lys Gly Asp Ala Gly Gln
                915                 920                 925

Pro Gly Glu Lys Gly Ser Pro Gly Ala Gln Gly Pro Pro Gly Ala Pro
        930                 935                 940

Gly Pro Leu Gly Ile Ala Gly Ile Thr Gly Ala Arg Gly Leu Ala Gly
945                 950                 955                 960

Pro Pro Gly Met Pro Gly Pro Arg Gly Ser Pro Gly Pro Gln Gly Val
                965                 970                 975

Lys Gly Glu Ser Gly Lys Pro Gly Ala Asn Gly Leu Ser Gly Glu Arg
                980                 985                 990

Gly Pro Pro Gly Pro Gln Gly Leu Pro Gly Leu Ala Gly Thr Ala Gly
        995                 1000                1005

Glu Pro Gly Arg Asp Gly Asn Pro Gly Ser Asp Gly Leu Pro Gly
    1010                1015                1020

Arg Asp Gly Ser Pro Gly Gly Lys Gly Asp Arg Gly Glu Asn Gly
    1025                1030                1035

Ser Pro Gly Ala Pro Gly Ala Pro Gly His Pro Gly Pro Pro Gly
    1040                1045                1050

Pro Val Gly Pro Ala Gly Lys Ser Gly Asp Arg Gly Glu Ser Gly
    1055                1060                1065

Pro Ala Gly Pro Ala Gly Ala Pro Gly Pro Ala Gly Ser Arg Gly
    1070                1075                1080

Ala Pro Gly Pro Gln Gly Pro Arg Gly Asp Lys Gly Glu Thr Gly
    1085                1090                1095

Glu Arg Gly Ala Ala Gly Ile Lys Gly His Arg Gly Phe Pro Gly
    1100                1105                1110

Asn Pro Gly Ala Pro Gly Ser Pro Gly Pro Ala Gly Gln Gln Gly
    1115                1120                1125

Ala Ile Gly Ser Pro Gly Pro Ala Gly Pro Arg Gly Pro Val Gly
    1130                1135                1140

Pro Ser Gly Pro Pro Gly Lys Asp Gly Thr Ser Gly His Pro Gly
    1145                1150                1155

```
Pro Ile Gly Pro Pro Gly Pro Arg Gly Asn Arg Gly Glu Arg Gly
    1160                1165                1170

Ser Glu Gly Ser Pro Gly His Pro Gly Gln Pro Gly Pro Pro Gly
    1175                1180                1185

Pro Pro Gly Ala Pro Gly Pro Cys Cys Gly Gly Val Gly Ala Ala
    1190                1195                1200

Ala Ile Ala Gly Ile Gly Gly Glu Lys Ala Gly Phe Ala Pro
    1205                1210                1215

Tyr Tyr Gly Asp Glu Pro Met Asp Phe Lys Ile Asn Thr Asp Glu
    1220                1225                1230

Ile Met Thr Ser Leu Lys Ser Val Asn Gly Gln Ile Glu Ser Leu
    1235                1240                1245

Ile Ser Pro Asp Gly Ser Arg Lys Asn Pro Ala Arg Asn Cys Arg
    1250                1255                1260

Asp Leu Lys Phe Cys His Pro Glu Leu Lys Ser Gly Glu Tyr Trp
    1265                1270                1275

Val Asp Pro Asn Gln Gly Cys Lys Leu Asp Ala Ile Lys Val Phe
    1280                1285                1290

Cys Asn Met Glu Thr Gly Glu Thr Cys Ile Ser Ala Asn Pro Leu
    1295                1300                1305

Asn Val Pro Arg Lys His Trp Trp Thr Asp Ser Ser Ala Glu Lys
    1310                1315                1320

Lys His Val Trp Phe Gly Glu Ser Met Asp Gly Gly Phe Gln Phe
    1325                1330                1335

Ser Tyr Gly Asn Pro Glu Leu Pro Glu Asp Val Leu Asp Val His
    1340                1345                1350

Leu Ala Phe Leu Arg Leu Leu Ser Ser Arg Ala Ser Gln Asn Ile
    1355                1360                1365

Thr Tyr His Cys Lys Asn Ser Ile Ala Tyr Met Asp Gln Ala Ser
    1370                1375                1380

Gly Asn Val Lys Lys Ala Leu Lys Leu Met Gly Ser Asn Glu Gly
    1385                1390                1395

Glu Phe Lys Ala Glu Gly Asn Ser Lys Phe Thr Tyr Thr Val Leu
    1400                1405                1410

Glu Asp Gly Cys Thr Lys His Thr Gly Glu Trp Ser Lys Thr Val
    1415                1420                1425

Phe Glu Tyr Arg Thr Arg Lys Ala Val Arg Leu Pro Ile Val Asp
    1430                1435                1440

Ile Ala Pro Tyr Asp Ile Gly Gly Pro Asp Gln Glu Phe Gly Val
    1445                1450                1455

Asp Val Gly Pro Val Cys Phe Leu
    1460                1465

<210> SEQ ID NO 3
<211> LENGTH: 475
<212> TYPE: PRT
<213> ORGANISM: Homo sapiens

<400> SEQUENCE: 3

Met Ala Ser Ala Ala Arg Leu Thr Met Met Trp Glu Glu Val Thr Cys
1               5                   10                  15

Pro Ile Cys Leu Asp Pro Phe Val Glu Pro Val Ser Ile Glu Cys Gly
                20                  25                  30

His Ser Phe Cys Gln Glu Cys Ile Ser Gln Val Gly Lys Gly Gly Gly
            35                  40                  45
```

```
Ser Val Cys Pro Val Cys Arg Gln Arg Phe Leu Leu Lys Asn Leu Arg
    50              55                  60

Pro Asn Arg Gln Leu Ala Asn Met Val Asn Asn Leu Lys Glu Ile Ser
65              70                  75                  80

Gln Glu Ala Arg Glu Gly Thr Gln Gly Glu Arg Cys Ala Val His Gly
                85                  90                  95

Glu Arg Leu His Leu Phe Cys Glu Lys Asp Gly Lys Ala Leu Cys Trp
            100                 105                 110

Val Cys Ala Gln Ser Arg Lys His Arg Asp His Ala Met Val Pro Leu
        115                 120                 125

Glu Glu Ala Ala Gln Glu Tyr Gln Glu Lys Leu Gln Val Ala Leu Gly
    130                 135                 140

Glu Leu Arg Arg Lys Gln Glu Leu Ala Glu Lys Leu Glu Val Glu Ile
145                 150                 155                 160

Ala Ile Lys Arg Ala Asp Trp Lys Lys Thr Val Glu Thr Gln Lys Ser
                165                 170                 175

Arg Ile His Ala Glu Phe Val Gln Gln Lys Asn Phe Leu Val Glu Glu
            180                 185                 190

Glu Gln Arg Gln Leu Gln Glu Leu Glu Lys Asp Glu Arg Glu Gln Leu
        195                 200                 205

Arg Ile Leu Gly Glu Lys Glu Ala Lys Leu Ala Gln Gln Ser Gln Ala
    210                 215                 220

Leu Gln Glu Leu Ile Ser Glu Leu Asp Arg Arg Cys His Ser Ser Ala
225                 230                 235                 240

Leu Glu Leu Leu Gln Glu Val Ile Ile Val Leu Glu Arg Ser Glu Ser
                245                 250                 255

Trp Asn Leu Lys Asp Leu Asp Ile Thr Ser Pro Glu Leu Arg Ser Val
            260                 265                 270

Cys His Val Pro Gly Leu Lys Lys Met Leu Arg Thr Cys Ala Val His
        275                 280                 285

Ile Thr Leu Asp Pro Asp Thr Ala Asn Pro Trp Leu Ile Leu Ser Glu
    290                 295                 300

Asp Arg Arg Gln Val Arg Leu Gly Asp Thr Gln Gln Ser Ile Pro Gly
305                 310                 315                 320

Asn Glu Glu Arg Phe Asp Ser Tyr Pro Met Val Leu Gly Ala Gln His
                325                 330                 335

Phe His Ser Gly Lys His Tyr Trp Glu Val Asp Val Thr Gly Lys Glu
            340                 345                 350

Ala Trp Asp Leu Gly Val Cys Arg Asp Ser Val Arg Arg Lys Gly His
        355                 360                 365

Phe Leu Leu Ser Ser Lys Ser Gly Phe Trp Thr Ile Trp Leu Trp Asn
    370                 375                 380

Lys Gln Lys Tyr Glu Ala Gly Thr Tyr Pro Gln Thr Pro Leu His Leu
385                 390                 395                 400

Gln Val Pro Pro Cys Gln Val Gly Ile Phe Leu Asp Tyr Glu Ala Gly
                405                 410                 415

Met Val Ser Phe Tyr Asn Ile Thr Asp His Gly Ser Leu Ile Tyr Ser
            420                 425                 430

Phe Ser Glu Cys Ala Phe Thr Gly Pro Leu Arg Pro Phe Phe Ser Pro
        435                 440                 445

Gly Phe Asn Asp Gly Gly Lys Asn Thr Ala Pro Leu Thr Leu Cys Pro
    450                 455                 460
```

```
Leu Asn Ile Gly Ser Gln Gly Ser Thr Asp Tyr
465                 470                 475
```

<210> SEQ ID NO 4
<211> LENGTH: 105
<212> TYPE: PRT
<213> ORGANISM: Homo sapiens

<400> SEQUENCE: 4

```
Met Arg Ser Phe Phe Ser Phe Leu Gly Glu Ala Phe Asp Gly Ala Arg
1               5                   10                  15

Asp Met Trp Arg Ala Tyr Ser Asp Met Arg Glu Ala Asn Tyr Ile Gly
            20                  25                  30

Ser Asp Lys Tyr Phe His Ala Arg Gly Asn Tyr Asp Ala Ala Lys Arg
        35                  40                  45

Gly Pro Gly Gly Val Trp Ala Ala Glu Ala Ile Ser Asn Ala Arg Glu
    50                  55                  60

Asn Ile Gln Arg Phe Phe Gly Arg Gly Ala Glu Asp Ser Leu Ala Asp
65                  70                  75                  80

Gln Ala Ala Asn Glu Trp Gly Arg Ser Gly Lys Asp Pro Asn His Phe
                85                  90                  95

Arg Pro Ala Gly Leu Pro Glu Lys Tyr
            100                 105
```

<210> SEQ ID NO 5
<211> LENGTH: 130
<212> TYPE: PRT
<213> ORGANISM: Homo sapiens

<400> SEQUENCE: 5

```
Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ala Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Lys Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys
    130
```

<210> SEQ ID NO 6
<211> LENGTH: 24
<212> TYPE: DNA
<213> ORGANISM: Artificial Sequence
<220> FEATURE:
<223> OTHER INFORMATION: synthetic

<400> SEQUENCE: 6

```
ttagggttag ggttagggtt aggg                                    24
```

<210> SEQ ID NO 7
<211> LENGTH: 132
<212> TYPE: PRT
<213> ORGANISM: Homo sapiens

<400> SEQUENCE: 7

Met Thr Gly Glu Leu Glu Val Lys Asn Met Asp Met Lys Pro Gly Ser
1               5                   10                  15

Thr Leu Lys Ile Thr Gly Ser Ile Ala Asp Gly Thr Asp Gly Phe Val
            20                  25                  30

Ile Asn Leu Gly Gln Gly Thr Asp Lys Leu Asn Leu His Phe Asn Pro
        35                  40                  45

Arg Phe Ser Glu Ser Thr Ile Val Cys Asn Ser Leu Asp Gly Ser Asn
    50                  55                  60

Trp Gly Gln Glu Gln Arg Glu Asp His Leu Cys Phe Ser Pro Gly Ser
65                  70                  75                  80

Glu Val Lys Phe Thr Val Thr Phe Glu Ser Asp Lys Phe Lys Val Lys
                85                  90                  95

Leu Pro Asp Gly His Glu Leu Thr Phe Pro Asn Arg Leu Gly His Ser
            100                 105                 110

His Leu Ser Tyr Leu Ser Val Arg Gly Gly Phe Asn Met Ser Ser Phe
        115                 120                 125

Lys Leu Lys Glu
    130

<210> SEQ ID NO 8
<211> LENGTH: 250
<212> TYPE: PRT
<213> ORGANISM: Mus musculus

<400> SEQUENCE: 8

Met Gly Asn His Ser Gly Lys Arg Glu Leu Ser Ala Glu Lys Ala Ser
1               5                   10                  15

Lys Asp Gly Glu Ile His Arg Gly Glu Ala Gly Lys Lys Arg Ser Val
            20                  25                  30

Gly Lys Leu Ser Gln Thr Ala Ser Glu Asp Ser Asp Val Phe Gly Glu
        35                  40                  45

Ala Asp Ala Ile Gln Asn Asn Gly Thr Ser Ala Glu Asp Thr Ala Val
    50                  55                  60

Thr Asp Ser Lys His Thr Ala Asp Pro Lys Asn Asn Trp Gln Gly Ala
65                  70                  75                  80

His Pro Ala Asp Pro Gly Asn Arg Pro His Leu Ile Arg Leu Phe Ser
                85                  90                  95

Arg Asp Ala Pro Gly Arg Glu Asp Asn Thr Phe Lys Arg Pro Arg Ser
            100                 105                 110

Glu Ser Asp Glu Leu Gln Thr Ile Gln Glu Asp Pro Thr Ala Ala Ser
        115                 120                 125

Gly Gly Leu Asp Val Met Ala Ser Gln Lys Arg Pro Ser Gln Arg Ser
    130                 135                 140

Lys Tyr Leu Ala Thr Ala Ser Thr Met Asp His Ala Arg His Gly Phe
145                 150                 155                 160

Leu Pro Arg His Arg Asp Thr Gly Ile Leu Asp Ser Ile Gly Arg Phe
                165                 170                 175

Phe Ser Gly Asp Arg Gly Ala Pro Lys Arg Gly Ser Gly Lys Asp Ser
            180                 185                 190

```
His Thr Arg Thr Thr His Tyr Gly Ser Leu Pro Gln Lys Ser Gln His
            195                 200                 205

Gly Arg Thr Gln Asp Glu Asn Pro Val Val His Phe Lys Asn Ile
    210                 215                 220

Val Thr Pro Arg Thr Pro Pro Ser Gln Gly Lys Gly Gly Arg Asp
225                 230                 235                 240

Ser Arg Ser Gly Ser Pro Met Ala Arg Arg
                245                 250

<210> SEQ ID NO 9
<211> LENGTH: 491
<212> TYPE: PRT
<213> ORGANISM: Homo sapiens

<400> SEQUENCE: 9

Met Asn Pro Phe Leu Ile Leu Ala Phe Val Gly Ala Ala Val Ala Val
1               5                   10                  15

Pro Phe Asp Asp Asp Lys Ile Val Gly Gly Tyr Thr Cys Glu Glu
                20                  25                  30

Asn Ser Leu Pro Tyr Gln Val Ser Leu Asn Ser Gly Ser His Phe Cys
            35                  40                  45

Gly Gly Ser Leu Ile Ser Glu Gln Trp Val Val Ser Ala Ala His Cys
    50                  55                  60

Tyr Lys Thr Arg Ile Gln Val Arg Leu Gly Glu His Asn Ile Lys Val
65                  70                  75                  80

Leu Glu Gly Asn Glu Gln Phe Ile Asn Ala Ala Lys Ile Ile Arg His
                85                  90                  95

Pro Gln Tyr Asp Arg Lys Thr Leu Asn Asn Asp Ile Met Leu Ile Lys
            100                 105                 110

Leu Ser Ser Arg Ala Val Ile Asn Ala Arg Val Ser Thr Ile Ser Leu
        115                 120                 125

Pro Thr Ala Pro Pro Ala Thr Gly Thr Lys Cys Leu Ile Ser Gly Trp
    130                 135                 140

Gly Asn Thr Ala Ser Ser Gly Ala Asp Tyr Pro Asp Glu Leu Gln Cys
145                 150                 155                 160

Leu Asp Ala Pro Val Leu Ser Gln Ala Lys Cys Glu Ala Ser Tyr Pro
                165                 170                 175

Gly Lys Ile Thr Ser Asn Met Phe Cys Val Gly Phe Leu Glu Gly Gly
            180                 185                 190

Lys Asp Ser Cys Gln Gly Asp Ser Gly Gly Pro Val Val Cys Asn Gly
        195                 200                 205

Gln Leu Gln Gly Val Val Ser Trp Gly Asp Gly Cys Ala Gln Lys Asn
    210                 215                 220

Lys Pro Gly Val Tyr Thr Lys Val Tyr Asn Tyr Val Lys Trp Ile Lys
225                 230                 235                 240

Asn Thr Ile Ala Ala Asn Ser Asp Ala Asp Gly Cys Glu Ala Leu Gly
                245                 250                 255

Thr Val Ala Val Pro Phe Asp Asp Asp Lys Ile Val Gly Gly Tyr
            260                 265                 270

Thr Cys Glu Glu Asn Ser Leu Pro Tyr Gln Val Ser Leu Asn Ser Gly
        275                 280                 285

Ser His Phe Cys Gly Gly Ser Leu Ile Ser Glu Gln Trp Val Val Ser
    290                 295                 300

Ala Ala His Cys Tyr Lys Thr Arg Ile Gln Val Arg Leu Gly Glu His
305                 310                 315                 320
```

Asn Ile Lys Val Leu Glu Gly Asn Glu Gln Phe Ile Asn Ala Ala Lys
             325                 330                 335

Ile Ile Arg His Pro Lys Tyr Asn Arg Asp Thr Leu Asp Asn Asp Ile
            340                 345                 350

Met Leu Ile Lys Leu Ser Ser Pro Ala Val Ile Asn Ala Arg Val Ser
            355                 360                 365

Thr Ile Ser Leu Pro Thr Thr Pro Ala Ala Gly Thr Glu Cys Leu
        370                 375                 380

Ile Ser Gly Trp Gly Asn Thr Leu Ser Phe Gly Ala Asp Tyr Pro Asp
385                 390                 395                 400

Glu Leu Lys Cys Leu Asp Ala Pro Val Leu Thr Gln Ala Glu Cys Lys
                405                 410                 415

Ala Ser Tyr Pro Gly Lys Ile Thr Asn Ser Met Phe Cys Val Gly Phe
            420                 425                 430

Leu Glu Gly Gly Lys Asp Ser Cys Gln Arg Asp Ser Gly Gly Pro Val
        435                 440                 445

Val Cys Asn Gly Gln Leu Gln Gly Val Val Ser Trp Gly His Gly Cys
    450                 455                 460

Ala Trp Lys Asn Arg Pro Gly Val Tyr Thr Lys Val Tyr Asn Tyr Val
465                 470                 475                 480

Asp Trp Ile Lys Asp Thr Ile Ala Ala Asn Ser
            485                 490

<210> SEQ ID NO 10
<211> LENGTH: 336
<212> TYPE: PRT
<213> ORGANISM: Toxoplasma gondii

<400> SEQUENCE: 10

Met Ser Val Ser Leu His His Phe Ile Ile Ser Ser Gly Phe Leu Thr
1               5                   10                  15

Ser Met Phe Pro Lys Ala Val Arg Arg Ala Val Thr Ala Gly Val Phe
            20                  25                  30

Ala Ala Pro Thr Leu Met Ser Phe Leu Arg Cys Gly Ala Met Ala Ser
        35                  40                  45

Asp Pro Pro Leu Val Ala Asn Gln Val Val Thr Cys Pro Asp Lys Lys
    50                  55                  60

Ser Thr Ala Ala Val Ile Leu Thr Pro Thr Glu Asn His Phe Thr Leu
65                  70                  75                  80

Lys Cys Pro Lys Thr Ala Leu Thr Glu Pro Pro Thr Leu Ala Tyr Ser
                85                  90                  95

Pro Asn Arg Gln Ile Cys Pro Ala Gly Thr Thr Ser Ser Cys Thr Ser
            100                 105                 110

Lys Ala Val Thr Leu Ser Ser Leu Ile Pro Glu Ala Glu Asp Ser Trp
        115                 120                 125

Trp Thr Gly Asp Ser Ala Ser Leu Asp Thr Ala Gly Ile Lys Leu Thr
    130                 135                 140

Val Pro Ile Glu Lys Phe Pro Val Thr Thr Gln Thr Phe Val Val Gly
145                 150                 155                 160

Cys Ile Lys Gly Asp Asp Ala Gln Ser Cys Met Val Thr Val Thr Val
                165                 170                 175

Gln Ala Arg Ala Ser Ser Val Val Asn Asn Val Ala Arg Cys Ser Tyr
            180                 185                 190

Gly Ala Asn Ser Thr Leu Gly Pro Val Lys Leu Ser Ala Glu Gly Pro

```
            195                 200                 205
Thr Thr Met Thr Leu Val Cys Gly Lys Asp Gly Val Lys Val Pro Gln
    210                 215                 220

Asp Asn Asn Gln Tyr Cys Ser Gly Thr Thr Leu Thr Gly Cys Asn Glu
225                 230                 235                 240

Lys Ser Phe Lys Asp Ile Leu Pro Lys Leu Ser Glu Asn Pro Trp Gln
                245                 250                 255

Gly Asn Ala Ser Ser Asp Asn Gly Ala Thr Leu Thr Ile Asn Lys Glu
                260                 265                 270

Ala Phe Pro Ala Glu Ser Lys Ser Val Ile Ile Gly Cys Thr Gly Gly
            275                 280                 285

Ser Pro Glu Lys His His Cys Thr Val Gln Leu Glu Phe Ala Gly Ala
290                 295                 300

Ala Gly Ser Ala Lys Ser Ser Ala Gly Thr Ala Ser His Val Ser Ile
305                 310                 315                 320

Phe Ala Met Val Thr Gly Leu Ile Gly Ser Ile Ala Ala Cys Val Ala
                325                 330                 335

<210> SEQ ID NO 11
<211> LENGTH: 168
<212> TYPE: PRT
<213> ORGANISM: Homo sapiens

<400> SEQUENCE: 11

Met Gly Ser Ser His His His His His His Ser Ser Gly Leu Val Pro
1               5                   10                  15

Arg Gly Ser His Met Glu Val Lys Asp Ala Asn Ser Ala Leu Leu Ser
            20                  25                  30

Asn Tyr Glu Val Phe Gln Leu Leu Thr Asp Leu Lys Glu Gln Arg Lys
        35                  40                  45

Glu Ser Gly Lys Asn Lys His Ser Ser Gly Gln Gln Asn Leu Asn Thr
    50                  55                  60

Ile Thr Tyr Glu Thr Leu Lys Tyr Ile Ser Lys Thr Pro Cys Arg His
65                  70                  75                  80

Gln Ser Pro Glu Ile Val Arg Glu Phe Leu Thr Ala Leu Lys Ser His
                85                  90                  95

Lys Leu Thr Lys Ala Glu Lys Leu Gln Leu Leu Asn His Arg Pro Val
            100                 105                 110

Thr Ala Val Glu Ile Gln Leu Met Val Glu Glu Ser Glu Glu Arg Leu
        115                 120                 125

Thr Glu Glu Gln Ile Glu Ala Leu Leu His Thr Val Thr Ser Ile Leu
    130                 135                 140

Pro Ala Glu Pro Glu Ala Glu Gln Lys Lys Asn Thr Asn Ser Asn Val
145                 150                 155                 160

Ala Met Asp Glu Glu Asp Pro Ala
                165

<210> SEQ ID NO 12
<211> LENGTH: 270
<212> TYPE: PRT
<213> ORGANISM: Homo sapiens

<400> SEQUENCE: 12

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
```

```
            20                  25                  30
Thr Asp Tyr Thr Ala Glu Cys Lys Pro Gln Val Thr Arg Gly Asp Val
         35                  40                  45

Phe Thr Met Pro Glu Asp Glu Tyr Thr Val Tyr Asp Asp Gly Glu Glu
 50                  55                  60

Lys Asn Asn Ala Thr Val His Glu Gln Val Gly Pro Ser Leu Thr
 65                  70                  75                  80

Ser Asp Leu Gln Ala Gln Ser Lys Gly Asn Pro Glu Gln Thr Pro Val
                 85                  90                  95

Leu Lys Pro Glu Glu Glu Ala Pro Ala Pro Glu Val Gly Ala Ser Lys
                100                 105                 110

Pro Glu Gly Ile Asp Ser Arg Pro Glu Thr Leu His Pro Gly Arg Pro
             115                 120                 125

Gln Pro Pro Ala Glu Glu Leu Cys Ser Gly Lys Pro Phe Asp Ala
     130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                 165                 170                 175

Ile Arg Asp Val Trp Gly Ile Glu Gly Pro Ile Asp Ala Ala Phe Thr
                 180                 185                 190

Arg Ile Asn Cys Gln Gly Lys Thr Tyr Leu Phe Lys Gly Ser Gln Tyr
             195                 200                 205

Trp Arg Phe Glu Asp Gly Val Leu Asp Pro Asp Tyr Pro Arg Asn Ile
     210                 215                 220

Ser Asp Gly Phe Asp Gly Ile Pro Asp Asn Val Asp Ala Ala Leu Ala
225                 230                 235                 240

Leu Pro Ala His Ser Tyr Ser Gly Arg Glu Arg Val Tyr Phe Phe Lys
                 245                 250                 255

Gly Lys Gln Tyr Trp Glu Tyr Gln Phe Gln His Gln Pro Ser
                 260                 265                 270

<210> SEQ ID NO 13
<211> LENGTH: 230
<212> TYPE: PRT
<213> ORGANISM: Homo sapiens

<400> SEQUENCE: 13

Met Glu Pro Leu Arg Leu Leu Ile Leu Leu Phe Val Thr Glu Leu Ser
 1               5                  10                  15

Gly Ala His Asn Thr Thr Val Phe Gln Gly Val Ala Gly Gln Ser Leu
                 20                  25                  30

Gln Val Ser Cys Pro Tyr Asp Ser Met Lys His Trp Gly Arg Arg Lys
             35                  40                  45

Ala Trp Cys Arg Gln Leu Gly Glu Lys Gly Pro Cys Gln Arg Val Val
 50                  55                  60

Ser Thr His Asn Leu Trp Leu Leu Ser Phe Leu Arg Arg Trp Asn Gly
 65                  70                  75                  80

Ser Thr Ala Ile Thr Asp Asp Thr Leu Gly Gly Thr Leu Thr Ile Thr
                 85                  90                  95

Leu Arg Asn Leu Gln Pro His Asp Ala Gly Leu Tyr Gln Cys Gln Ser
                100                 105                 110

Leu His Gly Ser Glu Ala Asp Thr Leu Arg Lys Val Leu Val Glu Val
             115                 120                 125
```

Leu Ala Asp Pro Leu Asp His Arg Asp Ala Gly Asp Leu Trp Phe Pro
130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
            165                 170                 175

Leu Leu Leu Ala Cys Ile Phe Leu Ile Lys Ile Leu Ala Ala Ser Ala
            180                 185                 190

Leu Trp Ala Ala Ala Trp His Gly Gln Lys Pro Gly Thr His Pro Pro
            195                 200                 205

Ser Glu Leu Asp Cys Gly His Asp Pro Gly Tyr Gln Leu Gln Thr Leu
210                 215                 220

Pro Gly Leu Arg Asp Thr
225                 230

<210> SEQ ID NO 14
<211> LENGTH: 350
<212> TYPE: PRT
<213> ORGANISM: Homo sapiens

<400> SEQUENCE: 14

Met Ser Ile Arg Val Thr Gln Lys Ser Tyr Lys Val Ser Thr Ser Gly
1               5                   10                  15

Pro Arg Ala Phe Ser Ser Arg Ser Tyr Thr Ser Gly Pro Gly Ser Arg
            20                  25                  30

Ile Ser Ser Ser Ser Phe Ser Arg Val Gly Ser Ser Asn Phe Arg Gly
            35                  40                  45

Gly Leu Gly Gly Gly Tyr Gly Gly Ala Ser Gly Met Gly Gly Ile Thr
50                  55                  60

Ala Val Thr Val Asn Gln Ser Leu Leu Ser Pro Leu Val Leu Glu Val
65                  70                  75                  80

Asp Pro Asn Ile Gln Ala Val Arg Thr Gln Glu Lys Glu Gln Ile Lys
            85                  90                  95

Thr Leu Asn Asn Lys Phe Ala Ser Phe Ile Asp Lys Val Arg Phe Leu
            100                 105                 110

Glu Gln Gln Asn Lys Met Leu Glu Thr Lys Trp Ser Leu Leu Gln Gln
            115                 120                 125

Gln Lys Thr Ala Arg Ser Asn Met Asp Asn Met Phe Glu Ser Tyr Ile
130                 135                 140

Asn Asn Leu Arg Arg Gln Leu Glu Thr Leu Gly Gln Glu Lys Leu Lys
145                 150                 155                 160

Leu Glu Ala Glu Leu Gly Asn Met Gln Gly Leu Val Glu Asp Phe Lys
            165                 170                 175

Asn Lys Tyr Glu Asp Glu Ile Asn Lys Arg Thr Glu Met Glu Asn Glu
            180                 185                 190

Phe Val Leu Ile Lys Lys Asp Val Asp Glu Ala Tyr Met Asn Lys Val
            195                 200                 205

Glu Leu Glu Ser Arg Leu Glu Gly Leu Thr Asp Glu Ile Asn Phe Leu
210                 215                 220

Arg Gln Leu Tyr Glu Glu Glu Ile Arg Glu Leu Gln Ser Gln Ile Ser
225                 230                 235                 240

Asp Thr Ser Val Val Leu Ser Met Asp Asn Ser Arg Ser Leu Asp Met
            245                 250                 255

Asp Ser Ile Ile Ala Glu Val Lys Ala Gln Tyr Glu Asp Ile Ala Asn
            260                 265                 270

-continued

Arg Ser Arg Ala Glu Ala Glu Ser Met Tyr Gln Ile Lys Tyr Glu Glu
            275                 280                 285

Leu Gln Ser Leu Ala Gly Lys His Gly Asp Asp Leu Arg Arg Thr Lys
        290                 295                 300

Thr Glu Ile Ser Glu Met Asn Arg Asn Ile Ser Arg Leu Gln Ala Glu
305                 310                 315                 320

Ile Glu Gly Leu Lys Gly Gln Arg Ala Ser Leu Glu Ala Ala Ile Ala
                325                 330                 335

Asp Ala Glu Gln Arg Gly Glu Leu Ala Ile Lys Asp Ala Asn
            340                 345                 350

<210> SEQ ID NO 15
<211> LENGTH: 197
<212> TYPE: PRT
<213> ORGANISM: Homo sapiens

<400> SEQUENCE: 15

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195

<210> SEQ ID NO 16
<211> LENGTH: 102
<212> TYPE: PRT
<213> ORGANISM: Homo sapiens

<400> SEQUENCE: 16

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

-continued

Lys Ala Phe Thr Val Cys Leu His Phe Tyr Thr Glu Leu Ser Ser Thr
 50                  55                  60

His Glu Ile Asn Thr Ile Tyr Leu Gly Gly Pro Phe Ser Pro Asn Val
 65                  70                  75                  80

Leu Asn Trp Arg Ala Leu Lys Tyr Glu Val Gln Gly Val Phe Thr
                 85                  90                  95

Lys Pro Gln Leu Trp Pro
            100

<210> SEQ ID NO 17
<211> LENGTH: 247
<212> TYPE: PRT
<213> ORGANISM: Homo sapiens

<400> SEQUENCE: 17

Met Glu Glu Gln Pro Gln Met Gln Asp Ala Asp Glu Pro Ala Asp Ser
 1               5                  10                  15

Gly Gly Glu Gly Arg Ala Gly Pro Pro Gln Val Ala Gly Ala Gln
                 20                  25                  30

Ala Ala Cys Ser Glu Asp Arg Met Thr Leu Leu Leu Arg Leu Arg Ala
            35                  40                  45

Gln Thr Lys Gln Gln Leu Leu Glu Tyr Lys Ser Met Val Asp Ala Ser
 50                  55                  60

Glu Glu Lys Thr Pro Glu Gln Ile Met Gln Glu Lys Gln Ile Glu Ala
 65                  70                  75                  80

Lys Ile Glu Asp Leu Glu Asn Glu Ile Glu Val Lys Val Ala Phe
                 85                  90                  95

Glu Ile Lys Lys Leu Ala Leu Asp Arg Met Arg Leu Ser Thr Ala Leu
            100                 105                 110

Lys Lys Asn Leu Glu Lys Ile Ser Arg Gln Ser Ser Val Leu Met Asp
            115                 120                 125

Asn Met Lys His Leu Leu Glu Leu Asn Lys Leu Ile Met Lys Ser Gln
            130                 135                 140

Gln Glu Ser Trp Asp Leu Glu Glu Lys Leu Leu Asp Ile Arg Lys Lys
145                 150                 155                 160

Arg Leu Gln Leu Lys Gln Ala Ser Glu Ser Lys Leu Leu Glu Ile Gln
                 165                 170                 175

Thr Glu Lys Asn Lys Gln Lys Ile Asp Leu Asp Ser Met Glu Asn Ser
            180                 185                 190

Glu Arg Ile Lys Ile Ile Arg Gln Asn Leu Gln Met Glu Ile Lys Ile
            195                 200                 205

Thr Thr Val Ile Gln His Val Phe Gln Asn Leu Ile Leu Gly Ser Lys
            210                 215                 220

Val Asn Trp Ala Glu Asp Pro Ala Leu Lys Glu Ile Val Leu Gln Leu
225                 230                 235                 240

Glu Lys Asn Val Asp Met Met
            245

<210> SEQ ID NO 18
<211> LENGTH: 222
<212> TYPE: PRT
<213> ORGANISM: Homo sapiens

<400> SEQUENCE: 18

Met Gly Lys Gly Asp Pro Lys Lys Pro Arg Gly Lys Met Ser Ser Tyr
 1               5                  10                  15

```
Ala Phe Phe Val Gln Thr Cys Arg Glu Glu His Lys Lys His Pro
             20                  25                  30

Asp Ala Ser Val Asn Phe Ser Glu Phe Ser Lys Lys Cys Ser Glu Arg
         35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu Asp
                180                 185                 190

Glu Glu Asp Glu Glu Glu Glu Asp Glu Glu Asp Glu Asp Glu Glu
            195                 200                 205

Glu Asp Asp Asp Glu Leu Glu His His His His His
            210                 215                 220

<210> SEQ ID NO 19
<211> LENGTH: 933
<212> TYPE: PRT
<213> ORGANISM: Homo sapiens

<400> SEQUENCE: 19

Met Arg Ala Leu Ala Val Leu Ser Val Thr Leu Val Met Ala Cys Thr
 1               5                  10                  15

Glu Ala Phe Phe Pro Phe Ile Ser Arg Gly Lys Glu Leu Leu Trp Gly
             20                  25                  30

Lys Pro Glu Glu Ser Arg Val Ser Val Leu Glu Ser Lys Arg
         35                  40                  45

Leu Val Asp Thr Ala Met Tyr Ala Thr Met Gln Arg Asn Leu Lys Lys
 50                  55                  60

Arg Gly Ile Leu Ser Pro Ala Gln Leu Leu Ser Phe Ser Lys Leu Pro
 65                  70                  75                  80

Glu Pro Thr Ser Gly Val Ile Ala Arg Ala Ala Glu Ile Met Glu Thr
                 85                  90                  95

Ser Ile Gln Ala Met Lys Arg Lys Val Asn Leu Lys Thr Gln Gln Ser
            100                 105                 110

Gln His Pro Thr Asp Ala Leu Ser Glu Asp Leu Leu Ser Ile Ile Ala
        115                 120                 125

Asn Met Ser Gly Cys Leu Pro Tyr Met Leu Pro Lys Cys Pro Asn
                130                 135                 140

Thr Cys Leu Ala Asn Lys Tyr Arg Pro Ile Thr Gly Ala Cys Asn Asn
145                 150                 155                 160

Arg Asp His Pro Arg Trp Gly Ala Ser Asn Thr Ala Leu Ala Arg Trp
```

```
                    165                 170                 175
Leu Pro Pro Val Tyr Glu Asp Gly Phe Ser Gln Pro Arg Gly Trp Asn
                180                 185                 190

Pro Gly Phe Leu Tyr Asn Gly Phe Pro Leu Pro Pro Val Arg Glu Val
            195                 200                 205

Thr Arg His Val Ile Gln Val Ser Asn Glu Val Val Thr Asp Asp Asp
        210                 215                 220

Arg Tyr Ser Asp Leu Leu Met Ala Trp Gly Gln Tyr Ile Asp His Asp
225                 230                 235                 240

Ile Ala Phe Thr Pro Gln Ser Thr Ser Lys Ala Ala Phe Gly Gly Gly
                245                 250                 255

Ala Asp Cys Gln Met Thr Cys Glu Asn Gln Asn Pro Cys Phe Pro Ile
            260                 265                 270

Gln Leu Pro Glu Glu Ala Arg Pro Ala Ala Gly Thr Ala Cys Leu Pro
        275                 280                 285

Phe Tyr Arg Ser Ser Ala Ala Cys Gly Thr Gly Asp Gln Gly Ala Leu
    290                 295                 300

Phe Gly Asn Leu Ser Thr Ala Asn Pro Arg Gln Gln Met Asn Gly Leu
305                 310                 315                 320

Thr Ser Phe Leu Asp Ala Ser Thr Val Tyr Gly Ser Pro Ala Leu
                325                 330                 335

Glu Arg Gln Leu Arg Asn Trp Thr Ser Ala Glu Gly Leu Leu Arg Val
            340                 345                 350

His Ala Arg Leu Arg Asp Ser Gly Arg Ala Tyr Leu Pro Phe Val Pro
        355                 360                 365

Pro Arg Ala Pro Ala Ala Cys Ala Pro Glu Pro Gly Ile Pro Gly Glu
    370                 375                 380

Thr Arg Gly Pro Cys Phe Leu Ala Gly Asp Gly Arg Ala Ser Glu Val
385                 390                 395                 400

Pro Ser Leu Thr Ala Leu His Thr Leu Trp Leu Arg Glu His Asn Arg
                405                 410                 415

Leu Ala Ala Ala Leu Lys Ala Leu Asn Ala His Trp Ser Ala Asp Ala
            420                 425                 430

Val Tyr Gln Glu Ala Arg Lys Val Val Gly Ala Leu His Gln Ile Ile
        435                 440                 445

Thr Leu Arg Asp Tyr Ile Pro Arg Ile Leu Gly Pro Glu Ala Phe Gln
    450                 455                 460

Gln Tyr Val Gly Pro Tyr Glu Gly Tyr Asp Ser Thr Ala Asn Pro Thr
465                 470                 475                 480

Val Ser Asn Val Phe Ser Thr Ala Ala Phe Arg Phe Gly His Ala Thr
                485                 490                 495

Ile His Pro Leu Val Arg Arg Leu Asp Ala Ser Phe Gln Glu His Pro
            500                 505                 510

Asp Leu Pro Gly Leu Trp Leu His Gln Ala Phe Phe Ser Pro Trp Thr
        515                 520                 525

Leu Leu Arg Gly Gly Gly Leu Asp Pro Leu Ile Arg Gly Leu Leu Ala
    530                 535                 540

Arg Pro Ala Lys Leu Gln Val Gln Asp Gln Leu Met Asn Glu Glu Leu
545                 550                 555                 560

Thr Glu Arg Leu Phe Val Leu Ser Asn Ser Ser Thr Leu Asp Leu Ala
                565                 570                 575

Ser Ile Asn Leu Gln Arg Gly Arg Asp His Gly Leu Pro Gly Tyr Asn
            580                 585                 590
```

```
Glu Trp Arg Glu Phe Cys Gly Leu Pro Arg Leu Glu Thr Pro Ala Asp
            595                 600                 605

Leu Ser Thr Ala Ile Ala Ser Arg Ser Val Ala Asp Lys Ile Leu Asp
610                 615                 620

Leu Tyr Lys His Pro Asp Asn Ile Asp Val Trp Leu Gly Gly Leu Ala
625                 630                 635                 640

Glu Asn Phe Leu Pro Arg Ala Arg Thr Gly Pro Leu Phe Ala Cys Leu
                645                 650                 655

Ile Gly Lys Gln Met Lys Ala Leu Arg Asp Gly Asp Trp Phe Trp Trp
                660                 665                 670

Glu Asn Ser His Val Phe Thr Asp Ala Gln Arg Glu Leu Glu Lys
                675                 680                 685

His Ser Leu Ser Arg Val Ile Cys Asp Asn Thr Gly Leu Thr Arg Val
            690                 695                 700

Pro Met Asp Ala Phe Gln Val Gly Lys Phe Pro Glu Asp Phe Glu Ser
705                 710                 715                 720

Cys Asp Ser Ile Thr Gly Met Asn Leu Glu Ala Trp Arg Glu Thr Phe
                725                 730                 735

Pro Gln Asp Asp Lys Cys Gly Phe Pro Glu Ser Val Glu Asn Gly Asp
                740                 745                 750

Phe Val His Cys Glu Glu Ser Gly Arg Arg Val Leu Val Tyr Ser Cys
            755                 760                 765

Arg His Gly Tyr Glu Leu Gln Gly Arg Glu Gln Leu Thr Cys Thr Gln
            770                 775                 780

Glu Gly Trp Asp Phe Gln Pro Pro Leu Cys Lys Asp Val Asn Glu Cys
785                 790                 795                 800

Ala Asp Gly Ala His Pro Pro Cys His Ala Ser Ala Arg Cys Arg Asn
                805                 810                 815

Thr Lys Gly Gly Phe Gln Cys Leu Cys Ala Asp Pro Tyr Glu Leu Gly
                820                 825                 830

Asp Asp Gly Arg Thr Cys Val Asp Ser Gly Arg Leu Pro Arg Val Thr
            835                 840                 845

Trp Ile Ser Met Ser Leu Ala Ala Leu Leu Ile Gly Gly Phe Ala Gly
            850                 855                 860

Leu Thr Ser Thr Val Ile Cys Arg Trp Thr Arg Thr Gly Thr Lys Ser
865                 870                 875                 880

Thr Leu Pro Ile Ser Glu Thr Gly Gly Gly Thr Pro Glu Leu Arg Cys
                885                 890                 895

Gly Lys His Gln Ala Val Gly Thr Ser Pro Gln Arg Ala Ala Ala Gln
                900                 905                 910

Asp Ser Glu Gln Glu Ser Ala Gly Met Glu Gly Arg Asp Thr His Arg
            915                 920                 925

Leu Pro Arg Ala Leu
    930

<210> SEQ ID NO 20
<211> LENGTH: 119
<212> TYPE: PRT
<213> ORGANISM: Homo sapiens

<400> SEQUENCE: 20

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
```

```
              20                  25                  30

His Pro Ala Glu Asn Gly Lys Ser Asn Phe Leu Asn Cys Tyr Val Ser
            35                  40                  45

Gly Phe His Pro Ser Asp Ile Glu Val Asp Leu Leu Lys Asn Gly Glu
        50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
            115

<210> SEQ ID NO 21
<211> LENGTH: 692
<212> TYPE: PRT
<213> ORGANISM: Homo sapiens

<400> SEQUENCE: 21

Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
            20                  25                  30

Val Asn Thr Ala Asp Gln Cys Ala Asn Arg Cys Thr Arg Asn Lys Gly
        35                  40                  45

Leu Pro Phe Thr Cys Lys Ala Phe Val Phe Asp Lys Ala Arg Lys Gln
    50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
            100                 105                 110

Lys Ser Gly Ile Lys Cys Gln Pro Trp Ser Ser Met Ile Pro His Glu
        115                 120                 125

His Ser Tyr Arg Gly Lys Asp Leu Gln Glu Asn Tyr Cys Arg Asn Pro
    130                 135                 140

Arg Gly Glu Glu Gly Gly Pro Trp Cys Phe Thr Ser Asn Pro Glu Val
145                 150                 155                 160

Arg Tyr Glu Val Cys Asp Ile Pro Gln Cys Ser Glu Val Glu Cys Met
                165                 170                 175

Thr Cys Asn Gly Glu Ser Tyr Arg Gly Leu Met Asp His Thr Glu Ser
            180                 185                 190

Gly Lys Ile Cys Gln Arg Trp Asp His Gln Thr Pro His Arg His Lys
        195                 200                 205

Phe Leu Pro Glu Arg Tyr Pro Asp Lys Gly Phe Asp Asp Asn Tyr Cys
    210                 215                 220

Arg Asn Pro Asp Gly Gln Pro Arg Pro Trp Cys Tyr Thr Leu Asp Pro
225                 230                 235                 240

His Thr Arg Trp Glu Tyr Cys Ala Ile Lys Thr Cys Ala Asp Asn Thr
                245                 250                 255

Met Asn Asp Thr Asp Val Pro Leu Glu Thr Thr Glu Cys Ile Gln Gly
            260                 265                 270
```

-continued

```
Gln Gly Glu Gly Tyr Arg Gly Thr Val Asn Thr Ile Trp Asn Gly Ile
            275                 280                 285

Pro Cys Gln Arg Trp Asp Ser Gln Tyr Pro His Glu His Asp Met Thr
290                 295                 300

Pro Glu Asn Phe Lys Cys Lys Asp Leu Arg Glu Asn Tyr Cys Arg Asn
305                 310                 315                 320

Pro Asp Gly Ser Glu Ser Pro Trp Cys Phe Thr Thr Asp Pro Asn Ile
                325                 330                 335

Arg Val Gly Tyr Cys Ser Gln Ile Pro Asn Cys Asp Met Ser His Gly
                340                 345                 350

Gln Asp Cys Tyr Arg Gly Asn Gly Lys Asn Tyr Met Gly Asn Leu Ser
            355                 360                 365

Gln Thr Arg Ser Gly Leu Thr Cys Ser Met Trp Asp Lys Asn Met Glu
370                 375                 380

Asp Leu His Arg His Ile Phe Trp Glu Pro Asp Ala Ser Lys Leu Asn
385                 390                 395                 400

Glu Asn Tyr Cys Arg Asn Pro Asp Asp Ala His Gly Pro Trp Cys
                405                 410                 415

Tyr Thr Gly Asn Pro Leu Ile Pro Trp Asp Tyr Cys Pro Ile Ser Arg
                420                 425                 430

Cys Glu Gly Asp Thr Thr Pro Thr Ile Val Asn Leu Asp His Pro Val
            435                 440                 445

Ile Ser Cys Ala Lys Thr Lys Gln Leu Arg Val Val Asn Gly Ile Pro
            450                 455                 460

Thr Arg Thr Asn Ile Gly Trp Met Val Ser Leu Arg Tyr Arg Asn Lys
465                 470                 475                 480

His Ile Cys Gly Gly Ser Leu Ile Lys Glu Ser Trp Val Leu Thr Ala
                485                 490                 495

Arg Gln Cys Phe Pro Ser Arg Asp Leu Lys Asp Tyr Glu Ala Trp Leu
            500                 505                 510

Gly Ile His Asp Val His Gly Arg Gly Asp Glu Lys Cys Lys Gln Val
            515                 520                 525

Leu Asn Val Ser Gln Leu Val Tyr Gly Pro Glu Gly Ser Asp Leu Val
530                 535                 540

Leu Met Lys Leu Ala Arg Pro Ala Val Leu Asp Asp Phe Val Ser Thr
545                 550                 555                 560

Ile Asp Leu Pro Asn Tyr Gly Cys Thr Ile Pro Glu Lys Thr Ser Cys
                565                 570                 575

Ser Val Tyr Gly Trp Gly Tyr Thr Gly Leu Ile Asn Tyr Asp Gly Leu
                580                 585                 590

Leu Arg Val Ala His Leu Tyr Ile Met Gly Asn Glu Lys Cys Ser Gln
            595                 600                 605

His His Arg Gly Lys Val Thr Leu Asn Glu Ser Glu Ile Cys Ala Gly
610                 615                 620

Ala Glu Lys Ile Gly Ser Gly Pro Cys Glu Gly Asp Tyr Gly Gly Pro
625                 630                 635                 640

Leu Val Cys Glu Gln His Lys Met Arg Met Val Leu Gly Val Ile Val
                645                 650                 655

Pro Gly Arg Gly Cys Ala Ile Pro Asn Arg Pro Gly Ile Phe Val Arg
                660                 665                 670

Val Ala Tyr Tyr Ala Lys Trp Ile His Lys Ile Ile Leu Thr Tyr Lys
            675                 680                 685

Val Pro Gln Ser
```

690

<210> SEQ ID NO 22
<211> LENGTH: 20
<212> TYPE: DNA
<213> ORGANISM: Artificial Sequence
<220> FEATURE:
<223> OTHER INFORMATION: synthetic

<400> SEQUENCE: 22
ccataattgc aaagcttctg    20

<210> SEQ ID NO 23
<211> LENGTH: 154
<212> TYPE: PRT
<213> ORGANISM: Homo sapiens

<400> SEQUENCE: 23

Met Lys Gly Arg Lys Thr Arg Ala Arg Arg Ala Ile Ala Ala His Tyr
1               5                   10                  15

Glu Val His Pro Arg Pro Gly Gln Asp Gly Ala Gln Ala Gly Val Asp
            20                  25                  30

Gly Thr Val Ser Gly Trp Glu Glu Ala Arg Ile Asn Ser Ser Ser Pro
        35                  40                  45

Leu Arg Tyr Asn Arg Gln Ile Gly Glu Phe Ile Val Thr Arg Ala Gly
50                  55                  60

Leu Tyr Tyr Leu Tyr Cys Gln Val His Phe Asp Glu Gly Lys Ala Val
65                  70                  75                  80

Tyr Leu Lys Leu Asp Leu Leu Val Asp Gly Val Leu Ala Leu Arg Cys
                85                  90                  95

Leu Glu Glu Phe Ser Ala Thr Ala Ala Ser Ser Leu Gly Pro Gln Leu
            100                 105                 110

Arg Leu Cys Gln Val Ser Gly Leu Leu Ala Leu Arg Pro Gly Ser Ser
        115                 120                 125

Leu Arg Ile Arg Thr Leu Pro Trp Ala His Leu Lys Ala Ala Pro Phe
130                 135                 140

Leu Thr Tyr Phe Gly Leu Phe Gln Val His
145                 150

<210> SEQ ID NO 24
<211> LENGTH: 106
<212> TYPE: PRT
<213> ORGANISM: Homo sapiens

<400> SEQUENCE: 24

Met Gly Ser Ser His His His His His His Ser Ser Gly Leu Val Pro
1               5                   10                  15

Arg Gly Ser His Met Ser Leu Pro Leu Asn Pro Lys Pro Phe Leu Asn
            20                  25                  30

Gly Leu Thr Gly Lys Pro Val Met Val Lys Leu Lys Trp Gly Met Glu
        35                  40                  45

Tyr Lys Gly Tyr Leu Val Ser Val Asp Gly Tyr Met Asn Met Gln Leu
50                  55                  60

Ala Asn Thr Glu Glu Tyr Ile Asp Gly Ala Leu Ser Gly His Leu Gly
65                  70                  75                  80

Glu Val Leu Ile Arg Cys Asn Asn Val Leu Tyr Ile Arg Gly Val Glu
                85                  90                  95

Glu Glu Glu Glu Asp Gly Glu Met Arg Glu

<210> SEQ ID NO 25
<211> LENGTH: 240
<212> TYPE: PRT
<213> ORGANISM: Homo sapiens

<400> SEQUENCE: 25

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Met Ala Lys Val Gln Val Asn Asn Val Val Leu
        35                  40                  45

Asp Asn Pro Ser Pro Phe Tyr Asn Pro Phe Gln Phe Glu Ile Thr Phe
    50                  55                  60

Glu Cys Ile Glu Asp Leu Ser Glu Asp Leu Glu Trp Lys Ile Ile Tyr
65                  70                  75                  80

Val Gly Ser Ala Glu Ser Glu Tyr Asp Gln Val Leu Asp Ser Val
                85                  90                  95

Leu Val Gly Pro Val Pro Ala Gly Arg His Met Phe Val Phe Gln Ala
            100                 105                 110

Asp Ala Pro Asn Pro Gly Leu Ile Pro Asp Ala Asp Ala Val Gly Val
            115                 120                 125

Thr Val Val Leu Ile Thr Cys Thr Tyr Arg Gly Gln Glu Phe Ile Arg
130                 135                 140

Val Gly Tyr Tyr Val Asn Asn Glu Tyr Thr Glu Thr Glu Leu Arg Glu
145                 150                 155                 160

Asn Pro Pro Val Lys Pro Asp Phe Ser Lys Leu Gln Arg Asn Ile Leu
                165                 170                 175

Ala Ser Asn Pro Arg Val Thr Arg Phe His Ile Asn Trp Glu Asp Asn
            180                 185                 190

Thr Glu Lys Leu Glu Asp Ala Glu Ser Ser Asn Pro Asn Leu Gln Ser
        195                 200                 205

Leu Leu Ser Thr Asp Ala Leu Pro Ser Ala Ser Lys Gly Trp Ser Thr
    210                 215                 220

Ser Glu Asn Ser Leu Asn Val Met Leu Glu Ser His Met Asp Cys Met
225                 230                 235                 240

<210> SEQ ID NO 26
<211> LENGTH: 893
<212> TYPE: PRT
<213> ORGANISM: Gallus gallus

<400> SEQUENCE: 26

Met Asp His His Tyr Asp Pro Gln Gln Thr Asn Asp Tyr Met Gln Pro
1               5                   10                  15

Glu Glu Asp Trp Asp Arg Asp Leu Leu Leu Asp Pro Ala Trp Glu Lys
            20                  25                  30

Gln Gln Arg Lys Thr Phe Thr Ala Trp Cys Asn Ser His Leu Arg Lys
        35                  40                  45

Ala Gly Thr Gln Ile Glu Asn Ile Glu Glu Asp Phe Arg Asp Gly Leu
    50                  55                  60

Lys Leu Met Leu Leu Leu Glu Val Ile Ser Gly Glu Arg Leu Ala Lys
65                  70                  75                  80

Pro Glu Arg Gly Lys Met Arg Val His Lys Ile Ser Asn Val Asn Lys

```
            85                  90                  95
Ala Leu Asp Phe Ile Ala Ser Lys Gly Val Lys Leu Val Ser Ile Gly
            100                 105                 110

Ala Glu Glu Ile Val Asp Gly Asn Val Lys Met Thr Leu Gly Met Ile
            115                 120                 125

Trp Thr Ile Ile Leu Arg Phe Ala Ile Gln Asp Ile Ser Val Glu Glu
            130                 135                 140

Thr Ser Ala Lys Glu Gly Leu Leu Leu Trp Cys Gln Arg Lys Thr Ala
145                 150                 155                 160

Pro Tyr Lys Asn Val Asn Ile Gln Asn Phe His Ile Ser Trp Lys Asp
                165                 170                 175

Gly Leu Gly Phe Cys Ala Leu Ile His Arg His Arg Pro Glu Leu Ile
                180                 185                 190

Asp Tyr Gly Lys Leu Arg Lys Asp Asp Pro Leu Thr Asn Leu Asn Thr
                195                 200                 205

Ala Phe Asp Val Ala Glu Lys Tyr Leu Asp Ile Pro Lys Met Leu Asp
            210                 215                 220

Ala Glu Asp Ile Val Gly Thr Ala Arg Pro Asp Glu Lys Ala Ile Met
225                 230                 235                 240

Thr Tyr Val Ser Ser Phe Tyr His Ala Phe Ser Gly Ala Gln Lys Ala
                245                 250                 255

Glu Thr Ala Ala Asn Arg Ile Cys Lys Val Leu Ala Val Asn Gln Glu
                260                 265                 270

Asn Glu Gln Leu Met Glu Asp Tyr Glu Lys Leu Ala Ser Asp Leu Leu
                275                 280                 285

Glu Trp Ile Arg Arg Thr Ile Pro Trp Leu Glu Asn Arg Ala Pro Glu
            290                 295                 300

Asn Thr Met Gln Ala Met Gln Gln Lys Leu Glu Asp Phe Arg Asp Tyr
305                 310                 315                 320

Arg Arg Leu His Lys Pro Pro Lys Val Gln Glu Lys Cys Gln Leu Glu
                325                 330                 335

Ile Asn Phe Asn Thr Leu Gln Thr Lys Leu Arg Leu Ser Asn Arg Pro
                340                 345                 350

Ala Phe Met Pro Ser Glu Gly Lys Met Val Ser Asp Ile Asn Asn Ala
                355                 360                 365

Trp Gly Gly Leu Glu Gln Ala Glu Lys Gly Tyr Glu Glu Trp Leu Leu
            370                 375                 380

Asn Glu Ile Arg Arg Leu Glu Arg Leu Asp His Leu Ala Glu Lys Phe
385                 390                 395                 400

Arg Gln Lys Ala Ser Ile His Glu Ser Trp Thr Asp Gly Lys Glu Ala
                405                 410                 415

Met Leu Gln Gln Lys Asp Tyr Glu Thr Ala Thr Leu Ser Glu Ile Lys
                420                 425                 430

Ala Leu Leu Lys Lys His Glu Ala Phe Glu Ser Asp Leu Ala Ala His
                435                 440                 445

Gln Asp Arg Val Glu Gln Ile Ala Ala Ile Ala Gln Glu Leu Asn Glu
            450                 455                 460

Leu Asp Tyr Tyr Asp Ser Pro Ser Val Asn Ala Arg Cys Gln Lys Ile
465                 470                 475                 480

Cys Asp Gln Trp Asp Asn Leu Gly Ala Leu Thr Gln Lys Arg Arg Glu
                485                 490                 495

Ala Leu Glu Arg Thr Glu Lys Leu Leu Glu Thr Ile Asp Gln Leu Tyr
            500                 505                 510
```

```
Leu Glu Tyr Ala Lys Arg Ala Ala Pro Phe Asn Asn Trp Met Glu Gly
            515                 520                 525

Ala Met Glu Asp Leu Gln Asp Thr Phe Ile Val His Thr Ile Glu Glu
        530                 535                 540

Ile Gln Gly Leu Thr Thr Ala His Glu Gln Phe Lys Ala Thr Leu Pro
545                 550                 555                 560

Asp Ala Asp Lys Glu Arg Gln Ala Ile Leu Gly Ile His Asn Glu Val
                565                 570                 575

Ser Lys Ile Val Gln Thr Tyr His Val Asn Met Ala Gly Thr Asn Pro
            580                 585                 590

Tyr Thr Thr Ile Thr Pro Gln Glu Ile Asn Gly Lys Trp Glu His Val
        595                 600                 605

Arg Gln Leu Val Pro Arg Arg Asp Gln Ala Leu Met Glu His Ala
    610                 615                 620

Arg Gln Gln Gln Asn Glu Arg Leu Arg Lys Gln Phe Gly Ala Gln Ala
625                 630                 635                 640

Asn Val Ile Gly Pro Trp Ile Gln Thr Lys Met Glu Ile Gly Arg
                645                 650                 655

Ile Ser Ile Glu Met His Gly Thr Leu Glu Asp Gln Leu Asn His Leu
            660                 665                 670

Arg Gln Tyr Glu Lys Ser Ile Val Asn Tyr Lys Pro Lys Ile Asp Gln
        675                 680                 685

Leu Glu Gly Asp His Gln Gln Ile Gln Glu Ala Leu Ile Phe Asp Asn
    690                 695                 700

Lys His Thr Asn Tyr Thr Met Glu His Ile Arg Val Gly Trp Glu Gln
705                 710                 715                 720

Leu Leu Thr Thr Ile Ala Arg Thr Ile Asn Glu Val Glu Asn Gln Ile
                725                 730                 735

Leu Thr Arg Asp Ala Lys Gly Ile Ser Gln Glu Gln Met Asn Glu Phe
            740                 745                 750

Arg Ala Ser Phe Asn His Phe Asp Arg Asp His Ser Gly Thr Leu Gly
        755                 760                 765

Pro Glu Glu Phe Lys Ala Cys Leu Ile Ser Leu Gly Tyr Asp Ile Gly
    770                 775                 780

Asn Asp Ala Gln Gly Glu Ala Glu Phe Ala Arg Ile Met Ser Ile Val
785                 790                 795                 800

Asp Pro Asn Arg Met Gly Val Val Thr Phe Gln Ala Phe Ile Asp Phe
                805                 810                 815

Met Ser Arg Glu Thr Ala Asp Thr Asp Thr Ala Asp Gln Val Met Ala
            820                 825                 830

Ser Phe Lys Ile Leu Ala Gly Asp Lys Asn Tyr Ile Thr Val Asp Glu
        835                 840                 845

Leu Arg Arg Glu Leu Pro Pro Asp Gln Ala Glu Tyr Cys Ile Ala Arg
    850                 855                 860

Met Ala Pro Tyr Asn Gly Arg Asp Ala Val Pro Gly Ala Leu Asp Tyr
865                 870                 875                 880

Met Ser Phe Ser Thr Ala Leu Tyr Gly Glu Ser Asp Leu
                885                 890

<210> SEQ ID NO 27
<211> LENGTH: 578
<212> TYPE: PRT
<213> ORGANISM: Toxoplasma gondii
```

<400> SEQUENCE: 27

```
Met Gly His Pro Thr Ser Phe Gly Gln Pro Ser Cys Leu Val Trp Leu
1               5                   10                  15

Ala Ala Ala Phe Leu Val Leu Gly Leu Cys Leu Val Gln Gln Gly Ala
            20                  25                  30

Gly Arg Gln Arg Pro His Gln Trp Lys Ser Ser Glu Ala Ala Leu Ser
        35                  40                  45

Val Ser Pro Ala Gly Asp Ile Val Asp Lys Tyr Ser Arg Asp Ser Thr
    50                  55                  60

Glu Gly Glu Asn Thr Val Ser Glu Gly Glu Ala Glu Gly Ser Arg Gly
65                  70                  75                  80

Gly Ser Trp Leu Glu Gln Gly Val Glu Leu Arg Ser Pro Ser Gln
                85                  90                  95

Asp Ser Gln Thr Gly Thr Ser Thr Ala Ser Pro Thr Gly Phe Arg Arg
            100                 105                 110

Leu Leu Arg Arg Leu Arg Phe Trp Arg Arg Gly Ser Thr Arg Gly Ser
        115                 120                 125

Asp Asp Ala Ala Glu Val Ser Arg Arg Thr Arg Val Pro Leu His Thr
    130                 135                 140

Arg Leu Leu Gln His Leu Arg Arg Val Ala Arg Ile Ile Arg His Gly
145                 150                 155                 160

Val Ser Ala Ala Gly Arg Leu Phe Gly Arg Val Arg Gln Val Glu
                165                 170                 175

Ala Glu Arg Pro Gln Pro Val Phe Thr Glu Gly Asp Pro Pro Asp Leu
            180                 185                 190

Glu Thr Asn Ser Leu Tyr Tyr Arg Asp Lys Val Pro Gly Gln Gly Ile
        195                 200                 205

Ile Gln Glu Ile Leu Arg Gln Lys Pro Gly Ile Ala His His Pro Glu
    210                 215                 220

Ser Phe Ser Val Val Ala Ala Asp Glu Arg Val Ser Arg Thr Leu Trp
225                 230                 235                 240

Ala Glu Gly Gly Val Val Arg Val Ala Ser Glu Leu Gly Gln Pro Gly
                245                 250                 255

Arg Val Leu Val Arg Gly Arg Arg Ile Gly Leu Phe Arg Pro Gly Met
            260                 265                 270

Gln Phe Glu Ala Thr Asp Gln Ala Thr Gly Glu Pro Met Thr Ala Leu
        275                 280                 285

Val Gly His Thr Val Leu Glu Ala Thr Ala Arg Asp Val Asp Ser Met
    290                 295                 300

Arg Asn Glu Gly Leu Ala Val Gly Leu Phe Gln Lys Val Lys Asn Pro
305                 310                 315                 320

Tyr Leu Ala Asn Arg Tyr Leu Arg Phe Leu Ala Pro Phe Asp Leu Val
                325                 330                 335

Thr Ile Pro Gly Lys Pro Leu Val Gln Lys Ala Lys Ser Arg Asn Glu
            340                 345                 350

Val Gly Trp Val Lys Asn Leu Leu Phe Leu Leu Pro Pro Thr His Val
        355                 360                 365

Asp Met Glu Thr Phe Val Asp Val Ile Gly Arg Phe Pro Gln Glu Asp
    370                 375                 380

Arg Pro Leu Ala Asp Ala Ala Arg Leu Tyr Leu Thr Val Gln Ala Val
385                 390                 395                 400

Arg Leu Val Ala His Leu Gln Asp Glu Gly Val Val His Gly Lys Ile
                405                 410                 415
```

Met Pro Asp Ser Phe Cys Leu Lys Arg Glu Gly Gly Leu Tyr Leu Arg
            420                 425                 430

Asp Phe Gly Ser Leu Val Arg Ala Gly Ala Lys Val Val Pro Ala
            435                 440                 445

Glu Tyr Asp Glu Tyr Thr Pro Pro Glu Gly Arg Ala Ala Arg Ser
450                 455                 460

Arg Phe Gly Ser Gly Ala Thr Thr Met Thr Tyr Ala Phe Asp Ala Trp
465                 470                 475                 480

Thr Leu Gly Ser Val Ile Phe Leu Ile Trp Cys Ser Arg Ala Pro Asp
                485                 490                 495

Thr Lys Ser Gly Tyr Glu Tyr Ser Val Glu Phe Phe Ser Arg Cys
            500                 505                 510

Arg Arg Val Pro Glu Asn Val Lys Leu Leu Val Tyr Lys Leu Ile Asn
            515                 520                 525

Pro Ser Val Glu Ala Arg Leu Leu Ala Leu Gln Ala Ile Glu Thr Pro
530                 535                 540

Glu Tyr Arg Glu Met Glu Glu Gln Leu Ser Ala Ala Ser Arg Leu Tyr
545                 550                 555                 560

Ser Gly Asp Gly Thr Leu Thr Gly Gly Asp Asp Met Pro Pro Leu
                565                 570                 575

Glu Thr

<210> SEQ ID NO 28
<211> LENGTH: 578
<212> TYPE: PRT
<213> ORGANISM: Homo sapiens

<400> SEQUENCE: 28

Met Gly Ser Ser His His His His His His Ser Ser Gly Leu Val Pro
1               5                   10                  15

Arg Gly Ser His Met Ala Ala Leu Thr Arg Asp Pro Gln Phe Gln Lys
                20                  25                  30

Leu Gln Gln Trp Tyr Arg Glu His Arg Ser Glu Leu Asn Leu Arg Arg
            35                  40                  45

Leu Phe Asp Ala Asn Lys Asp Arg Phe Asn His Phe Ser Leu Thr Leu
        50                  55                  60

Asn Thr Asn His Gly His Ile Leu Val Asp Tyr Ser Lys Asn Leu Val
65                  70                  75                  80

Thr Glu Asp Val Met Arg Met Leu Val Asp Leu Ala Lys Ser Arg Gly
                85                  90                  95

Val Glu Ala Ala Arg Glu Arg Met Phe Asn Gly Glu Lys Ile Asn Tyr
            100                 105                 110

Thr Glu Gly Arg Ala Val Leu His Val Ala Leu Arg Asn Arg Ser Asn
        115                 120                 125

Thr Pro Ile Leu Val Asp Gly Lys Asp Val Met Pro Glu Val Asn Lys
130                 135                 140

Val Leu Asp Lys Met Lys Ser Phe Cys Gln Arg Val Arg Ser Gly Asp
145                 150                 155                 160

Trp Lys Gly Tyr Thr Gly Lys Thr Ile Thr Asp Val Ile Asn Ile Gly
                165                 170                 175

Ile Gly Gly Ser Asp Leu Gly Pro Leu Met Val Thr Glu Ala Leu Lys
            180                 185                 190

Pro Tyr Ser Ser Gly Gly Pro Arg Val Trp Tyr Val Ser Asn Ile Asp
        195                 200                 205

```
Gly Thr His Ile Ala Lys Thr Leu Ala Gln Leu Asn Pro Glu Ser Ser
        210                 215                 220
Leu Phe Ile Ile Ala Ser Lys Thr Phe Thr Thr Gln Glu Thr Ile Thr
225                 230                 235                 240
Asn Ala Glu Thr Ala Lys Glu Trp Phe Leu Gln Ala Ala Lys Asp Pro
                245                 250                 255
Ser Ala Val Ala Lys His Phe Val Ala Leu Ser Thr Asn Thr Thr Lys
                260                 265                 270
Val Lys Glu Phe Gly Ile Asp Pro Gln Asn Met Phe Glu Phe Trp Asp
                275                 280                 285
Trp Val Gly Gly Arg Tyr Ser Leu Trp Ser Ala Ile Gly Leu Ser Ile
                290                 295                 300
Ala Leu His Val Gly Phe Asp Asn Phe Glu Gln Leu Leu Ser Gly Ala
305                 310                 315                 320
His Trp Met Asp Gln His Phe Arg Thr Thr Pro Leu Glu Lys Asn Ala
                325                 330                 335
Pro Val Leu Leu Ala Leu Leu Gly Ile Trp Tyr Ile Asn Cys Phe Gly
                340                 345                 350
Cys Glu Thr His Ala Met Leu Pro Tyr Asp Gln Tyr Leu His Arg Phe
                355                 360                 365
Ala Ala Tyr Phe Gln Gln Gly Asp Met Glu Ser Asn Gly Lys Tyr Ile
                370                 375                 380
Thr Lys Ser Gly Thr Arg Val Asp His Gln Thr Gly Pro Ile Val Trp
385                 390                 395                 400
Gly Glu Pro Gly Thr Asn Gly Gln His Ala Phe Tyr Gln Leu Ile His
                405                 410                 415
Gln Gly Thr Lys Met Ile Pro Cys Asp Phe Leu Ile Pro Val Gln Thr
                420                 425                 430
Gln His Pro Ile Arg Lys Gly Leu His His Lys Ile Leu Leu Ala Asn
                435                 440                 445
Phe Leu Ala Gln Thr Glu Ala Leu Met Arg Gly Lys Ser Thr Glu Glu
                450                 455                 460
Ala Arg Lys Glu Leu Gln Ala Ala Gly Lys Ser Pro Glu Asp Leu Glu
465                 470                 475                 480
Arg Leu Leu Pro His Lys Val Phe Glu Gly Asn Arg Pro Thr Asn Ser
                485                 490                 495
Ile Val Phe Thr Lys Leu Thr Pro Phe Met Leu Gly Ala Leu Val Ala
                500                 505                 510
Met Tyr Glu His Lys Ile Phe Val Gln Gly Ile Ile Trp Asp Ile Asn
                515                 520                 525
Ser Phe Asp Gln Trp Gly Val Glu Leu Gly Lys Gln Leu Ala Lys Lys
                530                 535                 540
Ile Glu Pro Glu Leu Asp Gly Ser Ala Gln Val Thr Ser His Asp Ala
545                 550                 555                 560
Ser Thr Asn Gly Leu Ile Asn Phe Ile Lys Gln Gln Arg Glu Ala Arg
                565                 570                 575
Val Gln
```

<210> SEQ ID NO 29
<211> LENGTH: 381
<212> TYPE: PRT
<213> ORGANISM: Homo sapiens

<400> SEQUENCE: 29

```
Met Pro Phe Ser Asn Ser His Asn Ala Leu Lys Leu Arg Phe Pro Ala
1               5                   10                  15

Glu Asp Glu Phe Pro Asp Leu Ser Ala His Asn Asn His Met Ala Lys
            20                  25                  30

Val Leu Thr Pro Glu Leu Tyr Ala Glu Leu Arg Ala Lys Ser Thr Pro
        35                  40                  45

Ser Gly Phe Thr Leu Asp Asp Val Ile Gln Thr Gly Val Asp Asn Pro
50                  55                  60

Gly His Pro Tyr Ile Met Thr Val Gly Cys Val Ala Gly Asp Glu Glu
65                      70                  75                  80

Ser Tyr Glu Val Phe Lys Asp Leu Phe Asp Pro Ile Ile Glu Asp Arg
                85                  90                  95

His Gly Gly Tyr Lys Pro Ser Asp Glu His Lys Thr Asp Leu Asn Pro
            100                 105                 110

Asp Asn Leu Gln Gly Gly Asp Asp Leu Asp Pro Asn Tyr Val Leu Ser
        115                 120                 125

Ser Arg Val Arg Thr Gly Arg Ser Ile Arg Gly Phe Cys Leu Pro Pro
130                 135                 140

His Cys Ser Arg Gly Glu Arg Arg Ala Ile Glu Lys Leu Ala Val Glu
145                     150                 155                 160

Ala Leu Ser Ser Leu Asp Gly Asp Leu Ala Gly Arg Tyr Tyr Ala Leu
                165                 170                 175

Lys Ser Met Thr Glu Ala Glu Gln Gln Gln Leu Ile Asp Asp His Phe
            180                 185                 190

Leu Phe Asp Lys Pro Val Ser Pro Leu Leu Leu Ala Ser Gly Met Ala
        195                 200                 205

Arg Asp Trp Pro Asp Ala Arg Gly Ile Trp His Asn Asp Asn Lys Thr
210                 215                 220

Phe Leu Val Trp Val Asn Glu Glu Asp His Leu Arg Val Ile Ser Met
225                     230                 235                 240

Gln Lys Gly Gly Asn Met Lys Glu Val Phe Thr Arg Phe Cys Thr Gly
                245                 250                 255

Leu Thr Gln Ile Glu Thr Leu Phe Lys Ser Lys Asp Tyr Glu Phe Met
            260                 265                 270

Trp Asn Pro His Leu Gly Tyr Ile Leu Thr Cys Pro Ser Asn Leu Gly
        275                 280                 285

Thr Gly Leu Arg Ala Gly Val His Ile Lys Leu Pro Asn Leu Gly Lys
290                 295                 300

His Glu Lys Phe Ser Glu Val Leu Lys Arg Leu Arg Leu Gln Lys Arg
305                     310                 315                 320

Gly Thr Gly Gly Val Asp Thr Ala Ala Val Gly Gly Val Phe Asp Val
                325                 330                 335

Ser Asn Ala Asp Arg Leu Gly Phe Ser Glu Val Glu Leu Val Gln Met
            340                 345                 350

Val Val Asp Gly Val Lys Leu Leu Ile Glu Met Glu Gln Arg Leu Glu
        355                 360                 365

Gln Gly Gln Ala Ile Asp Asp Leu Met Pro Ala Gln Lys
370                 375                 380
```

<210> SEQ ID NO 30
<211> LENGTH: 354
<212> TYPE: PRT
<213> ORGANISM: Homo sapiens

<400> SEQUENCE: 30

```
Met Lys Ser Lys Leu Pro Lys Pro Val Gln Asp Leu Ile Lys Met Ile
1               5                   10                  15

Phe Asp Val Glu Ser Met Lys Lys Ala Met Val Glu Tyr Glu Ile Asp
            20                  25                  30

Leu Gln Lys Met Pro Leu Gly Lys Leu Ser Lys Arg Gln Ile Gln Ala
        35                  40                  45

Ala Tyr Ser Ile Leu Ser Glu Val Gln Gln Ala Val Ser Gln Gly Ser
    50                  55                  60

Ser Asp Ser Gln Ile Leu Asp Leu Ser Asn Arg Phe Tyr Thr Leu Ile
65                  70                  75                  80

Pro His Asp Phe Gly Met Lys Lys Pro Pro Leu Leu Asn Asn Ala Asp
                85                  90                  95

Ser Val Gln Ala Lys Ala Glu Met Leu Asp Asn Leu Leu Asp Ile Glu
            100                 105                 110

Val Ala Tyr Ser Leu Leu Arg Gly Gly Ser Asp Asp Ser Ser Lys Asp
        115                 120                 125

Pro Ile Asp Val Asn Tyr Glu Lys Leu Lys Thr Asp Ile Lys Val Val
130                 135                 140

Asp Arg Asp Ser Glu Glu Ala Glu Ile Ile Arg Lys Tyr Val Lys Asn
145                 150                 155                 160

Thr His Ala Thr Thr His Asn Ala Tyr Asp Leu Glu Val Ile Asp Ile
                165                 170                 175

Phe Lys Ile Glu Arg Glu Gly Glu Cys Gln Arg Tyr Lys Pro Phe Lys
            180                 185                 190

Gln Leu His Asn Arg Arg Leu Leu Trp His Gly Ser Arg Thr Thr Asn
        195                 200                 205

Phe Ala Gly Ile Leu Ser Gln Gly Leu Arg Ile Ala Pro Pro Glu Ala
    210                 215                 220

Pro Val Thr Gly Tyr Met Phe Gly Lys Gly Ile Tyr Phe Ala Asp Met
225                 230                 235                 240

Val Ser Lys Ser Ala Asn Tyr Cys His Thr Ser Gln Gly Asp Pro Ile
                245                 250                 255

Gly Leu Ile Leu Leu Gly Glu Val Ala Leu Gly Asn Met Tyr Glu Leu
            260                 265                 270

Lys His Ala Ser His Ile Ser Lys Leu Pro Lys Gly Lys His Ser Val
        275                 280                 285

Lys Gly Leu Gly Lys Thr Thr Pro Asp Pro Ser Ala Asn Ile Ser Leu
    290                 295                 300

Asp Gly Val Asp Val Pro Leu Gly Thr Gly Ile Ser Ser Gly Val Asn
305                 310                 315                 320

Asp Thr Ser Leu Leu Tyr Asn Glu Tyr Ile Val Tyr Asp Ile Ala Gln
                325                 330                 335

Val Asn Leu Lys Tyr Leu Leu Lys Leu Lys Phe Asn Phe Lys Thr Ser
            340                 345                 350

Leu Trp
```

<210> SEQ ID NO 31
<211> LENGTH: 161
<212> TYPE: PRT
<213> ORGANISM: Homo sapiens

<400> SEQUENCE: 31

```
Met Asp Asp Ile Tyr Lys Ala Ala Val Glu Gln Leu Thr Glu Glu Gln
```

```
              1               5                   10                  15
Lys Asn Glu Phe Lys Ala Ala Phe Asp Ile Phe Val Leu Gly Ala Glu
              20                  25                  30

Asp Gly Cys Ile Ser Thr Lys Glu Leu Gly Lys Val Met Arg Met Leu
              35                  40                  45

Gly Gln Asn Pro Thr Pro Glu Leu Gln Glu Met Ile Asp Glu Val
              50                  55                  60

Asp Glu Asp Gly Ser Gly Thr Val Asp Phe Asp Glu Phe Leu Val Met
65                70                  75                  80

Met Val Arg Cys Met Lys Asp Asp Ser Lys Gly Lys Ser Glu Glu Glu
                  85                  90                  95

Leu Ser Asp Leu Phe Arg Met Phe Asp Lys Asn Ala Asp Gly Tyr Ile
                  100                 105                 110

Asp Leu Asp Glu Leu Lys Ile Met Leu Gln Ala Thr Gly Glu Thr Ile
                  115                 120                 125

Thr Glu Asp Asp Ile Glu Glu Leu Met Lys Asp Gly Asp Lys Asn Asn
              130                 135                 140

Asp Gly Arg Ile Asp Tyr Asp Glu Phe Leu Glu Phe Met Lys Gly Val
145               150                 155                 160

Glu

<210> SEQ ID NO 32
<211> LENGTH: 471
<212> TYPE: PRT
<213> ORGANISM: Homo sapiens

<400> SEQUENCE: 32

Ser Thr Arg Ser Val Ser Ser Ser Tyr Arg Arg Met Phe Gly Gly
1               5                   10                  15

Pro Gly Thr Ala Ser Arg Pro Ser Ser Ser Arg Ser Tyr Val Thr Thr
              20                  25                  30

Ser Thr Arg Thr Tyr Ser Leu Gly Ser Ala Leu Arg Pro Ser Thr Ser
              35                  40                  45

Arg Ser Leu Tyr Ala Ser Ser Pro Gly Gly Val Tyr Ala Thr Arg Ser
              50                  55                  60

Ser Ala Val Arg Leu Arg Ser Ser Val Pro Gly Val Arg Leu Leu Gln
65                70                  75                  80

Asp Ser Val Asp Phe Ser Leu Ala Asp Ala Ile Asn Thr Glu Phe Lys
                  85                  90                  95

Asn Thr Arg Thr Asn Glu Lys Val Glu Leu Gln Glu Leu Asn Asp Arg
                  100                 105                 110

Phe Ala Asn Tyr Ile Asp Lys Val Arg Phe Leu Glu Gln Gln Asn Lys
                  115                 120                 125

Ile Leu Leu Ala Glu Leu Glu Gln Leu Lys Gly Gln Gly Lys Ser Arg
              130                 135                 140

Leu Gly Asp Leu Tyr Glu Glu Glu Met Arg Glu Leu Arg Arg Gln Val
145               150                 155                 160

Asp Gln Leu Thr Asn Asp Lys Ala Arg Val Glu Val Glu Arg Asp Asn
                  165                 170                 175

Leu Ala Glu Asp Ile Met Arg Leu Arg Glu Lys Leu Gln Glu Glu Met
                  180                 185                 190

Leu Gln Arg Glu Glu Ala Glu Asn Thr Leu Gln Ser Phe Arg Gln Asp
                  195                 200                 205

Val Asp Asn Ala Ser Leu Ala Arg Leu Asp Leu Glu Arg Lys Val Glu
```

```
                  210                 215                 220

Ser Leu Gln Glu Glu Ile Ala Phe Leu Lys Lys Leu His Glu Glu
225                 230                 235                 240

Ile Gln Glu Leu Gln Ala Gln Ile Gln Glu Gln His Val Gln Ile Asp
                    245                 250                 255

Val Asp Val Ser Lys Pro Asp Leu Thr Ala Ala Leu Arg Asp Val Arg
                260                 265                 270

Gln Gln Tyr Glu Ser Val Ala Ala Lys Asn Leu Gln Glu Ala Glu Glu
            275                 280                 285

Trp Tyr Lys Ser Lys Phe Ala Asp Leu Ser Glu Ala Ala Asn Arg Asn
        290                 295                 300

Asn Asp Ala Leu Arg Gln Ala Lys Gln Glu Ser Thr Glu Tyr Arg Arg
305                 310                 315                 320

Gln Val Gln Ser Leu Thr Cys Glu Val Asp Ala Leu Lys Gly Thr Asn
                325                 330                 335

Glu Ser Leu Glu Arg Gln Met Arg Glu Met Glu Glu Asn Phe Ala Val
                340                 345                 350

Glu Ala Ala Asn Tyr Gln Asp Thr Ile Gly Arg Leu Gln Asp Glu Ile
            355                 360                 365

Gln Asn Met Lys Glu Glu Met Ala Arg His Leu Arg Glu Tyr Gln Asp
        370                 375                 380

Leu Leu Asn Val Lys Met Ala Leu Asp Ile Glu Ile Ala Thr Tyr Arg
385                 390                 395                 400

Lys Leu Leu Glu Gly Glu Glu Ser Arg Ile Ser Leu Pro Leu Pro Asn
                405                 410                 415

Phe Ser Ser Leu Asn Leu Arg Glu Thr Asn Leu Asp Ser Leu Pro Leu
                420                 425                 430

Val Asp Thr His Ser Lys Arg Thr Leu Leu Ile Lys Thr Val Glu Thr
            435                 440                 445

Arg Asp Gly Gln Val Ile Asn Glu Thr Ser Gln His His Asp Asp Leu
        450                 455                 460

Glu His His His His His His
465                 470

<210> SEQ ID NO 33
<211> LENGTH: 20
<212> TYPE: DNA
<213> ORGANISM: Artificial Sequence
<220> FEATURE:
<223> OTHER INFORMATION: synthetic

<400> SEQUENCE: 33
gagagagaga gagagagaga                                              20

<210> SEQ ID NO 34
<211> LENGTH: 140
<212> TYPE: PRT
<213> ORGANISM: Homo sapiens

<400> SEQUENCE: 34

Met Gly Pro Arg Arg Ser Arg Lys Pro Glu Ala Pro Arg Arg
1               5                   10                  15

Ser Pro Ser Pro Thr Pro Thr Pro Gly Pro Ser Arg Arg Gly Pro Ser
                20                  25                  30

Leu Gly Ala Ser Ser His Gln His Ser Arg Arg Arg Gln Gly Trp Leu
            35                  40                  45
```

```
Lys Glu Ile Arg Lys Leu Gln Lys Ser Thr His Leu Leu Ile Arg Lys
         50                  55                  60

Leu Pro Phe Ser Arg Leu Ala Arg Glu Ile Cys Val Lys Phe Thr Arg
 65                  70                  75                  80

Gly Val Asp Phe Asn Trp Gln Ala Gln Ala Leu Leu Ala Leu Gln Glu
                 85                  90                  95

Ala Ala Glu Ala Phe Leu Val His Leu Phe Glu Asp Ala Tyr Leu Leu
            100                 105                 110

Thr Leu His Ala Gly Arg Val Thr Leu Phe Pro Lys Asp Val Gln Leu
            115                 120                 125

Ala Arg Arg Ile Arg Gly Leu Glu Glu Gly Leu Gly
130                 135                 140
```

<210> SEQ ID NO 35
<211> LENGTH: 359
<212> TYPE: PRT
<213> ORGANISM: Toxoplasma gondii

<400> SEQUENCE: 35

```
Met Arg Gly Gly Thr Ser Ala Leu Leu His Ala Leu Thr Phe Ser Gly
 1               5                  10                  15

Ala Val Trp Met Cys Thr Pro Ala Glu Ala Leu Pro Ile Gln Lys Ser
                20                  25                  30

Val Gln Leu Gly Ser Phe Asp Lys Val Val Pro Ser Arg Glu Val Val
            35                  40                  45

Ser Glu Ser Leu Ala Pro Ser Phe Ala Val Thr Glu Thr His Ser Ser
        50                  55                  60

Val Gln Ser Pro Ser Lys Gln Glu Thr Gln Leu Cys Ala Ile Ser Ser
 65                  70                  75                  80

Glu Gly Lys Pro Cys Arg Asn Arg Gln Leu His Thr Asp Asn Gly Tyr
                 85                  90                  95

Phe Ile Gly Ala Ser Cys Pro Lys Ser Ala Cys Cys Ser Lys Thr Met
            100                 105                 110

Cys Gly Pro Gly Gly Cys Gly Glu Phe Cys Ser Ser Asn Trp Ile Phe
            115                 120                 125

Cys Ser Ser Ser Leu Ile Tyr His Pro Asp Lys Ser Tyr Gly Gly Asp
            130                 135                 140

Cys Ser Cys Glu Lys Gln Gly His Arg Cys Asp Lys Asn Ala Glu Cys
145                 150                 155                 160

Val Glu Asn Leu Asp Ala Gly Gly Val His Cys Lys Cys Lys Asp
                165                 170                 175

Gly Phe Val Gly Thr Gly Leu Thr Cys Ser Glu Asp Pro Cys Ser Lys
            180                 185                 190

Arg Gly Asn Ala Lys Cys Gly Pro Asn Gly Thr Cys Ile Val Val Asp
            195                 200                 205

Ser Val Ser Tyr Thr Cys Thr Cys Gly Asp Gly Glu Thr Leu Val Asn
            210                 215                 220

Leu Pro Glu Gly Gly Gln Gly Cys Lys Arg Thr Gly Cys His Ala Phe
225                 230                 235                 240

Arg Glu Asn Cys Ser Pro Gly Arg Cys Ile Asp Asp Ala Ser His Glu
                245                 250                 255

Asn Gly Tyr Thr Cys Glu Cys Pro Thr Gly Tyr Ser Arg Glu Val Thr
            260                 265                 270

Ser Lys Ala Glu Glu Ser Cys Val Glu Gly Val Glu Val Thr Leu Ala
            275                 280                 285
```

Glu Lys Cys Glu Lys Glu Phe Gly Ile Ser Ala Ser Ser Cys Lys Cys
        290                 295                 300

Asp Asn Gly Tyr Ser Gly Ser Ala Ser Ala Thr Ser His His Gly Lys
305                 310                 315                 320

Gly Glu Ser Gly Ser Glu Gly Ser Leu Ser Glu Lys Met Asn Ile Val
                325                 330                 335

Phe Lys Cys Pro Ser Gly Tyr His Pro Arg Tyr His Ala His Thr Val
                340                 345                 350

Thr Cys Glu Lys Ile Lys Gln
            355

<210> SEQ ID NO 36
<211> LENGTH: 20
<212> TYPE: DNA
<213> ORGANISM: Artificial Sequence
<220> FEATURE:
<223> OTHER INFORMATION: synthetic

<400> SEQUENCE: 36
ccataattgc aaacgttctg                                               20

<210> SEQ ID NO 37
<211> LENGTH: 10
<212> TYPE: DNA
<213> ORGANISM: Artificial Sequence
<220> FEATURE:
<223> OTHER INFORMATION: synthetic

<400> SEQUENCE: 37
gggggggggg                                                          10

<210> SEQ ID NO 38
<211> LENGTH: 18
<212> TYPE: DNA
<213> ORGANISM: Artificial Sequence
<220> FEATURE:
<223> OTHER INFORMATION: synthetic

<400> SEQUENCE: 38
tttttttttt tttttgg                                                  18

<210> SEQ ID NO 39
<211> LENGTH: 20
<212> TYPE: DNA
<213> ORGANISM: Artificial Sequence
<220> FEATURE:
<223> OTHER INFORMATION: synthetic

<400> SEQUENCE: 39
aaaaaaaaaa aaaaaaaaaa                                               20

<210> SEQ ID NO 40
<211> LENGTH: 106
<212> TYPE: PRT
<213> ORGANISM: Homo sapiens

<400> SEQUENCE: 40

Lys Lys Asn Lys Asn Cys Arg Arg His Ser Leu Tyr Val Asp Phe Ser
1               5                   10                  15

Asp Val Gly Trp Asn Asp Trp Ile Val Ala Pro Pro Gly Tyr Gln Ala
                20                  25                  30

Phe Tyr Cys His Gly Asp Cys Pro Phe Pro Leu Ala Asp His Leu Asn

```
                35                  40                  45
Ser Thr Asn His Ala Ile Val Gln Thr Leu Val Asn Ser Val Asn Ser
    50                  55                  60

Ser Ile Pro Lys Ala Cys Cys Val Pro Thr Glu Leu Ser Ala Ile Ser
65                  70                  75                  80

Met Leu Tyr Leu Asp Glu Tyr Asp Lys Val Val Leu Lys Asn Tyr Gln
                85                  90                  95

Glu Met Val Val Glu Gly Cys Gly Cys Arg
                100                 105

<210> SEQ ID NO 41
<211> LENGTH: 17
<212> TYPE: DNA
<213> ORGANISM: Artificial Sequence
<220> FEATURE:
<223> OTHER INFORMATION: synthetic

<400> SEQUENCE: 41
gggggggggg gggggt                                                  17

<210> SEQ ID NO 42
<211> LENGTH: 20
<212> TYPE: DNA
<213> ORGANISM: Artificial Sequence
<220> FEATURE:
<223> OTHER INFORMATION: synthetic

<400> SEQUENCE: 42
ccataattcg aaacgttctg                                              20
```

DIAGNOSIS OF SYSTEMIC LUPUS ERYTHEMATOSUS USING PROTEIN, PEPTIDE AND OLIGONUCLEOTIDE ANTIGENS

SEQUENCE LISTING

The Sequence Listing submitted in text format (.txt) filed on Jan. 4, 2018, named "SequenceListing.txt", created on Jan. 3, 2018, 101 KB), is incorporated herein by reference.

FIELD OF THE INVENTION

The present invention relates to protein, peptide, polynucleotide and oligonucleotide antigens useful in diagnosing or monitoring an autoimmune disorder such as systemic lupus erythematosus (SLE) in a subject.

BACKGROUND OF THE INVENTION

Systemic lupus erythematosus (SLE) is a chronic, recurrent, potentially fatal multisystem inflammatory disorder mainly affecting women. SLE is associated with a large spectrum of autoantibodies. IgG antibodies to more than 100 different antigens including DNA, nucleosomes, histones, viral antigens, transcription factors and more have been reported in different SLE patients (Sherer et al., 2004, Semin. Arthritis. Rheum. 34:501-37). Surprisingly, there is no serologic diagnosis of SLE and SLE is diagnosed on the basis of eleven criteria defined by the American College of Rheumatology (ACR). These criteria include malar rash, discoid rash, photosensitivity, oral ulcers, arthritis, serositis, renal disorder, neurologic disorder, hematologic disorder (e.g., leucopenia, lymphopenia, hemolytic anemia or thrombocytopenia), immunologic disorder and antibody abnormalities (particularly anti-nuclear antibodies (ANA) and anti-DNA antibodies) (Tan et al., 1997, Arthritis Rheum 1997, 40:1725). According to these criteria, subjects can be clinically diagnosed with SLE if they meet at least four of the eleven criteria. Recently, the Systemic Lupus Collaborating Clinics (SLICC) revised these criteria, as reviewed in Petri et al. (Arthritis and Rheumatism, 2012, Vol. 64, pages 2677-2686). Nevertheless, SLE is still possible even in cases when less than four criteria are present.

ANA laboratory testing is one of the standards in SLE diagnosis; negative test results help 'rule out' SLE in >95% of cases. Positive ANAs lack specificity, since any antibody to nuclear components is an ANA and can occur in many autoimmune rheumatic diseases, chronic inflammatory and infectious diseases, malignancies, and can also be induced by certain drugs. Furthermore, the unaffected healthy population is estimated to be 20% ANA positive (ANA+) at a 1:80 serum dilution-level. As a result, ANA+ test results contribute to the false positive rate of the laboratory testing component when initially diagnosing SLE. Therefore, it is recommended that ANA+ test results be followed by testing for antigen-specific ANAs, including anti double stranded DNA (dsDNA) and anti-Smith antibodies; however, these are detectable in only ~30% of SLE patients.

Although the precise pathology of SLE is not clear, it is widely accepted that autoantibodies play an important role. Autoantibodies to DNA are highly heterogeneous with respect to their avidity, immunoglobulin subclass composition, cross-reactivity and complement fixing ability. A number of techniques have been utilized for DNA autoantibodies detection, including immunofluorescent assays (IFA), enzyme-linked immunosorbent assays (ELISAs) and radio-immunoassays (RIA). However, the clinical value of anti-dsDNA antibodies largely depends on the assay principle and analytical variables of the methods used to quantitate and immunologically characterize them.

F. J. Quintana et al. ("Antigen-chip technology for accessing global information about the state of the body", Lupus, 2006, Vol. 15(7), pages 428-30) describe the use of microarray technology and informatics to develop an antigen chip capable of detecting global patterns of antibodies binding to hundreds of antigens simultaneously. Lupus is disclosed to be one of the interests of the authors.

J. G. Hanly at al. ("Measurement of autoantibodies using multiplex methodology in patients with systemic lupus erythematosus", Journal of Immunological Methods, 2010, Vol. 352, pages 147-152) have compared laser bead immunoassay technology to more traditional measures of autoantibody detection in diagnosis and assessment of systemic lupus erythematosus (SLE). The autoantigens used included, for example, dsDNA, Sm, and RNP.

Q. Z. Li et al. ("Protein array autoantibody profiles for insights into systemic lupus erythematosus and incomplete lupus syndromes", Clinical & Experimental Immunology, 2006, Vol. 147 (1), pages 60-70) investigated the prevalence and clinical significance of a spectrum of autoantibodies in systemic lupus erythematosus and incomplete lupus syndromes using a proteome microarray bearing 70 autoantigens, such as ssDNA and U1 snRNP.

W. H. Robinson et al. ("Autoantigen microarrays for multiplex characterization of autoantibody responses", Nature Medicine, 2002, Vol. 8, pages 295-301) describe and characterize arrays bearing 196 autoantigens containing the major autoantigens in eight distinct human autoimmune diseases, including systemic lupus erythematosus. The autoantigens included, for example, ssDNA, Sm/RNP and U1 snRNP.

Flares occur in approximately 80% of patients during the course of their disease [Petri M, et al., Am J Med 1991; 91: 345-54], and generally require the introduction or increase in dose of a variety of potentially toxic therapies. The morbidity and mortality associated with flares can be substantial, and is related to organ damage resulting from active SLE per se and the adverse effects of corticosteroids and immunosuppressive drugs [Abu-Sharaka M, et al., J Rheumatol 1995; 22: 1259-64].

One of the most difficult challenges in clinical management of complex autoimmune diseases such as SLE is the accurate and early identification of the disease in a patient and differentiation between patients with active disease (flare) and those with non-active disease (in remission). There remains a need for improved diagnostic methods and kits useful in diagnosing SLE in a subject.

SUMMARY OF THE INVENTION

The present invention provides methods and kits for diagnosing or monitoring an autoimmune disorder, particularly systemic lupus erythematosus (SLE). The present invention further provides antigen probe arrays for practicing such a diagnosis, and antigen probe sets for generating such arrays.

The present invention is based, in part, on the unexpected results obtained when testing the antibody reactivity of SLE patients compared to healthy controls. Surprisingly, significantly different immunoglobulin G (IgG) and IgM reactivities to specific protein, peptide, polynucleotide and oligonucleotide antigens were found in the tested SLE patients, compared to healthy controls. Thus, the present invention provides unique protein, peptide polynucleotide and oligonucleotide antigens indicative to SLE. The present invention further provides antigen-autoantibody reactivity patterns relevant to SLE. In particular embodiments, the present invention provides highly sensitive, specific, reliable, accurate and discriminatory assays for diagnosing SLE, based on the indicative protein, peptide and oligonucleotide antigens, or on reactivity patterns thereof.

The present invention is also based, in part; on the use of specific classifiers involve machine learning algorithms on pre-selected features which contain the highest ranking of information discriminating SLE samples from healthy controls. For example, the logistic regression (LR) analysis of a particular antibody immune signature as described herein, provided an assay for diagnosing SLE with remarkably high sensitivity and specificity (0.98 and 0.59, respectively). The present invention is further based, in part, on the unexpected finding that the antibody reactivity profile in serum of SLE patients was clearly distinct from healthy control individuals.

Thus, according to embodiments of the invention, there are provided novel methods for diagnosing, ruling out a diagnosis, and monitoring the progression of SLE. According to embodiments of the invention, there are provided methods for diagnosing pre-lupus state or early lupus state.

According to embodiments of the invention, the methods comprise determining the reactivity of antibodies in a sample obtained or derived from a subject to a plurality of antigens as described herein. The methods of the invention further comprise a step of comparing the reactivity of antibodies in the sample to the plurality of antigens to control reactivity to said plurality of antigens. According to certain embodiments, a significantly different reactivity of the antibodies in the sample compared to the reactivity of the healthy control is an indication that the subject is afflicted with SLE.

According to a first aspect, the present invention provides a method of diagnosing SLE in a subject suspected of having SLE, the method comprising the steps of: obtaining a sample from the subject; determining the reactivity of antibodies in the sample to at least four antigens selected from the group consisting of ssDNA, Sm, DNAse I, Histone III-S, Ro52 (TRIM21), U1 snRNP, Collagen III, Apo-SAA, H2a and Oligo21, thereby determining the reactivity pattern of the sample to the plurality of antigens; and comparing the reactivity of antibodies in the sample to a reactivity of a healthy control by a supervised classification algorithm; wherein a significantly different reactivity of the antibodies in the sample compared to the reactivity of the healthy control is an indication that the subject is afflicted with SLE.

According to another embodiment, the source of said ssDNA antigen is selected from a human, a salmon and a calf. According to said embodiment, determining the reactivity of ssDNA comprises determining the reactivity of ssDNA from a human source, a salmon source or reactivity of ssDNA from a calf source. According to another embodiment, the source of said ssDNA antigen is a calf.

According to some embodiments, the reactivity of antibodies comprises IgG reactivities, IgM reactivities, or any combination thereof. According to some embodiments, the reactivity of the antibodies comprises increased IgG and IgM reactivities.

According to certain embodiments, the supervised classification algorithm is selected from the group consisting of a decision tree classifier, logistic regression (LR) classifier, nearest neighbor classifier, neural network classifier, Gaussian mixture model (GMM), Support Vector Machine (SVM) classifier, nearest centroid classifier, linear regression classifier, linear discriminant analysis (LDA) classifier, quadratic discriminant analysis (QDA) classifier and random forest classifier.

According to some embodiments, the supervised classification algorithm is selected from the group consisting of support vector machines (SVMs), logistic regression (LR), quadratic discriminant analysis (QDA), and linear discriminant analysis (LDA).

According to some embodiments, the method of the present invention comprising determining the reactivities of IgG antibodies in the sample to ssDNA, Sm, DNAse I, Ro52 and U1 snRNP, determining the reactivities of IgM antibodies in the sample to Histone III-S, and comparing the reactivity of antibodies in the sample to a reactivity of a healthy control by support vector machines (SVMs).

According to some embodiments, the method of the present invention comprising determining the reactivities of IgG antibodies in the sample to ssDNA, U1 snRNP, Ro52, Collagen III and Apo-SAA, determining the reactivities of IgM antibodies in the sample to Histone III-S, and comparing the reactivity of antibodies in the sample to a reactivity of a healthy control by logistic regression (LR).

According to some embodiments, the method of the present invention comprising determining the reactivities of IgG antibodies in the sample to ssDNA, U1 snRNP, Sm, Apo-SAA and Ro52, determining the reactivities of IgM antibodies in the sample to H2a, and comparing the reactivity of antibodies in the sample to a reactivity of a healthy control by quadratic discriminant analysis (QDA).

According to some embodiments, the method of the present invention comprising determining the reactivities of IgG antibodies in the sample to ssDNA, U1 snRNP and Sm, determining the reactivities of IgM antibodies in the sample to Histone III-S, U1 snRNP and Oligo21, and comparing the reactivity of antibodies in the sample to a reactivity of a healthy control by linear discriminant analysis (LDA).

According to some embodiments, the method of the present invention comprising determining the reactivities of antibodies in the sample to ssDNA, U1 snRNP and Histone III-S.

According to some embodiments, the logistic regression (LR), quadratic discriminant analysis (QDA), and linear discriminant analysis (LDA) have predicted probability values of 0-1.

According to some embodiments of the methods of the present invention, the sample obtained from the subject is a biological fluid. According to some embodiments, the sample is selected from the group consisting of plasma, serum, blood, cerebrospinal fluid, synovial fluid, sputum, urine, saliva, tears, lymph specimen, or any other biological fluid known in the art. Each possibility represents a separate embodiment of the invention. According to certain embodiments, the sample obtained from the subject is selected from the group consisting of serum, plasma and blood. According to one embodiment, the sample is a serum sample.

According to certain embodiments of the methods of the present invention, the control is selected from the group consisting of a sample from at least one healthy individual, a panel of control samples from a set of healthy individuals, a baseline sample from same subject, and a stored set of data from healthy individuals. Typically, a healthy individual is a subject not afflicted with SLE (or any other form of lupus). In another embodiment, a healthy individual is a subject not afflicted with an autoimmune disease.

According to certain embodiments, the subject is positive for an antinuclear antibody (ANA) test. According to certain embodiments, the method of the present invention can be used to rule out a diagnosis of SLE. According to certain embodiments, the method of the present invention can be used to rule in a diagnosis of SLE.

According to another aspect, the present invention provides a method for classifying a subject as having systemic lupus erythematosus (SLE) in an active phase or in a non-active phase, the method comprising the steps of: obtaining a sample from the subject; determining the reactivity of antibodies in the sample to at least four antigens selected from Table 8, thereby determining the reactivity pattern of the sample to the plurality of antigens; calculating a score based on the reactivity of antibodies in the sample by a supervised classification algorithm and comparing said score to a pre-determined threshold level; wherein a significantly different reactivity of the antibodies in the sample with a score above the pre-determined threshold level, is an indication that the subject is afflicted with an active phase of SLE According to certain embodiments, the supervised classification algorithm is selected from the group consisting of support vector machines (SVMs), logistic regression (LR), and classification and regression tree (CART).

According to another aspect the present invention provides a kit for the diagnosis or monitoring of SLE in a subject comprising the plurality of antigens of the invention or a subset thereof.

According to another aspect, the present invention provides an antigen probe set comprising the plurality of antigen probes of the invention, or a subset thereof.

According to another aspect, the present invention provides an article of manufacture comprising the antigen probe set of the present invention.

According to another aspect, there is provided use of an antigen probe set comprising a plurality of antigen probes of the invention, for the preparation of a diagnostic kit for diagnosing SLE in a subject. Said diagnostic kit is, in some embodiments, useful for determining the reactivity of antibodies in a sample, thereby determining the reactivity pattern of the sample to said plurality of antigens. In some embodiments, a significant difference between the reactivity pattern of said sample compared to a reactivity pattern of a control sample is an indication for SLE.

Other objects, features and advantages of the present invention will become clear from the following description and drawings.

DETAILED DESCRIPTION OF THE INVENTION

Figure 1:
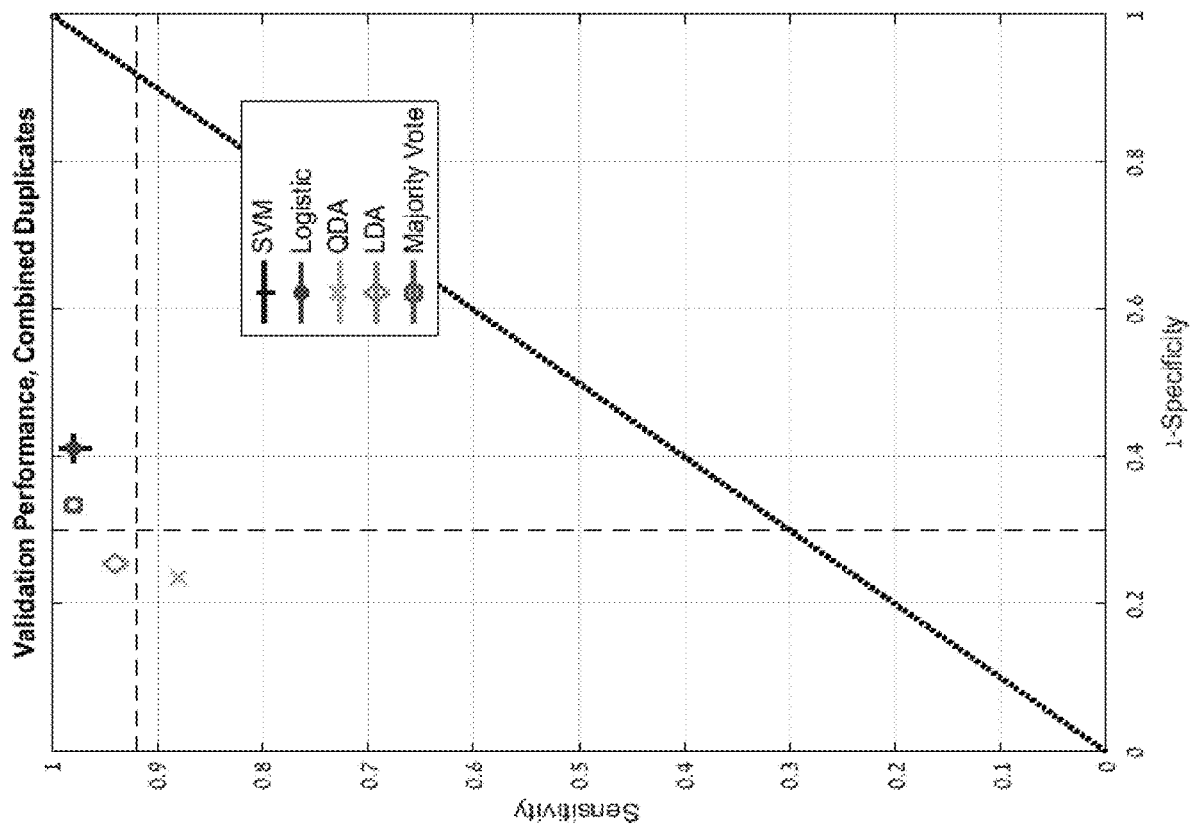
FIG. 1 demonstrates the performance of five classification methods (SVM, LR, QDA, LDA and Majority Vote) in the validation test. Validation of the performance of the different classification methods was performed on a set of 50 SLE patients and 50 healthy controls comparing the sensitivity (y-axis) and the specificity (1-specificity, x-axis) of the classification methods. Dashed lines represent the thresholds.

The present invention provides methods of diagnosing an autoimmune disease or disorder, specifically systemic lupus erythematosus (SLE), in a subject. The present invention further provides antigen probe sets or arrays for practicing such a diagnosis, and identifies specific antigen probe sets for generating such arrays. The platform technology of the present invention apply novel biomarker signature to measure changes in immune system response by observing changes in autoantibodies. The present invention can predict response prior to therapy and identify adverse events prior to irreversible injury/damage. The present invention can objectively identify disease or healthy state such as excluding SLE from patient with unclear diagnosis and excluding SLE from otherwise healthy ANA(+) patient. The classification methods of the present invention can be used to support decision making to the diagnosis or ruling out of SLE. The methods may also be used to track patients' immune profiles over time to monitor changes in disease state and/or response to therapy.

Without wishing to be bound by any particular theory or mechanism of action, the invention is based, in part, on the finding of unique, highly distinctive antibody reactivity profiles in serum of SLE patients, clearly distinct from healthy control individuals. Although serum autoantibodies have been extensively investigated in SLE, the unique antibody immune signatures as described herein had not been described before. Advantageously, the unique antibody signatures of the present disclosure provide highly sensitive and specific assays for diagnosing SLE or for ruling out a diagnosis of SLE.

The methods of the present invention allow the determination of the pattern of circulating antibodies to said array of antigens. This pattern is compared to SLE affected and healthy control patterns. The classifier algorithms of the present invention are used to determine the likelihood of the patient being affected with SLE, along with a probability score.

Further, the present invention provides, in some embodiments, unique antigen-autoantibody reactivity patterns particularly relevant to SLE. As exemplified herein below, a quadratic discriminant classifier (QDA) analysis including the following antigens: ssDNA, U1 snRNP, Sm, Apo-SAA and Ro52, H2a, exhibited an AUC value of 95%. Additional SLE-related antigens are presented herein below in Table 1.

As exemplified herein below, antigen analysis of autoantibodies (e.g., using microarray analysis) can identify serum autoantibody patterns associated with SLE. In particular embodiments, the methods of the invention are based on collective autoantibody patterns. The informative patterns include, in some embodiments, decreases and increases of IgG antibodies as well as decreases and increases of IgM antibodies, relative to those found in healthy controls.

In some embodiment, the method comprises: obtaining a sample from a subject; determining the reactivity of IgG and/or IgM antibodies in the sample to the plurality of antigens described herein; thereby determining the reactivity pattern of the sample to the plurality of antigens; and comparing the reactivity pattern of said sample to a control reactivity pattern; wherein a significant difference between the reactivity pattern of said sample obtained from the subject compared to the reactivity pattern of a control sample is an indication that the subject is afflicted with SLE.

In some embodiment, the plurality of antigens for discriminating SLE and healthy controls is selected from the group consisting of: ssDNA, Sm, DNAse I, Histone IIIS, Ro52, U1 snRNP, Collagen III, Apo-SAA, H2a and Oligo21. In particular embodiments, said plurality of antigens comprises Histone IIIS and at least one, at least two, at least three, at least four, at least five, at least six or at least seven antigens selected from the group consisting of: U1 snRNP, ssDNA, Sm, DNAse I, Ro52, Collagen III, Apo-SAA, H2a and Oligo21.

In some embodiment, the plurality of antigens for discriminating SLE and healthy controls is selected from the group of antigens listed in Table 1 (SEQ ID NO: 1-11) and any combinations thereof.

TABLE 1

List of SLE related antigens used for discriminating SLE and healthy controls

| Antigen | SEQ ID NO: | Full name/amino acid or oligonucleotide sequence | Manufacture (catalolg no.) |
|---|---|---|---|
| DNAse I | 1 | Deoxyribonuclease I<br>MRGMKLLGALLALAALLQGAVSLKIAAFNIQTFGETKMSNATLVSYIVQILSR<br>YDIALVQEVRDSHLTAVGKLLDNLNQDAPDTYHYVVSEPLGRNSYKERYLFVY<br>RPDQVSAVDSYYYDDGCEPCGNDTFNREPAIVRFFSRFTEVREFAIVPLHAAP<br>GDAVAEIDALYDVYLDVQEKWGLEDVMLMGDFNAGCSYVRPSQWSSIRLWTSP<br>TFQWLIPDSADTTATPTHCAYDRIVVAGMLLRGAVVPDSALPFNFQAAYGLSD<br>QLAQAISDHYPVEVMLK | AKRON biotech (AK3778) |
| salmon ssDNA | | single stranded DNA (salmon testes) | Sigma (D9156) |
| calf ssDNA | | single stranded DNA (calf) | Sigma (D8899) |
| Histone IIIS | | Histone from calf thymus (Type III-S) | Sigma (H5505) |
| Collagen III | 2 | Type III collagen<br>MMSFVQKGSWLLLALLHPTIILAQQEAVEGGCSHLGQSYADRDVWKPEPCQIC<br>VCDSGSVLCDDIICDDQELDCPNPEIPFGECCAVCPQPPTAPTRPPNGQGPQG<br>PKGDPGPPGIPGRNGDPGIPGQPGSPGSPGPPGICESCPTGPQNYSPQYDSYD<br>VKSGVAVGGLAGYPGPAGPPGPPGPPGTSGHPGSPGSPGYQGPPGEPGQAGPS<br>GPPGPPGAIGPSGPAGKDGESGRPGRPGERGLPGPPGIKGPAGIPGFPGMKGH<br>RGFDGRNGEKGETGAPGLKGENGLPGENGAPGPMGPRGAPGERGRPGLPGAAG<br>ARGNDGARGSDGQPGPPGPPGTAGFPGSPGAKGEVGPAGSPGSNGAPGQRGEP<br>GPQGHAGAQGPPGPPGINGSPGGKGEMGPAGIPGAPGLMGARGPPGPAGANGA<br>PGLRGGAGEPGKNGAKGEPGPRGERGEAGIPGVPGAKGEDGKDGSPGEPGANG<br>LPGAAGERGAPGFRGPAGPNGIPGEKGPAGERGAPGPAGPRGAAGEPGRDGVP<br>GGPGMRGMPGSPGGPGSDGKPGPPGSQGESGRPGPPGPSGPRGQPGVMGFPGP<br>KGNDGAPGKNGERGGPGGPGPQGPPGKNGETGPQGPPGPTGPGGDKGDTGPPG<br>PQGLQGLPGTGGPPGENGKPGEPGPKGDAGAPGAPGGKGDAGAPGERGPPGLA<br>GAPGLRGGAGPPGPEGGKGAAGPPGPPGAAGTPGLQGMPGERGGLGSPGPKGD<br>KGEPGQPGADGVPGKDGPRGPTGPIGPPGPAGQPGDKGEGGAPGLPGIAGPRG<br>SPGERGETGPPGPAGFPGAPGQNGEPGGKGERGAPGEKGEGGPPGVAGPPGGS<br>GPAGPPGPQGVKGERGSPGQPGAAGFPGARGLPGPPGSNGNPGPPGPSGSPGK<br>DGPPGPAGNTGAPGSPGVSGPKGDAGQPGEKGSPGAQGPPGAPGPLGIAGITG<br>ARGLAGPPGMPGPRGSPGPQGVKGESGKPGANGLSGERGPPGPQGLPGLAGTA<br>GEPGRDGNPGSDGLPGRDGSPGGKGDRGENGSPGAPGAPGHPGPPGPVGPAGK<br>SGDRGESGPAGPAGAPGPAGSRGAPGPQGPRGDKGETGERGAAGIKGHRGFPG | AKRON biotech (AK9914) |

TABLE 1-continued

List of SLE related antigens used for discriminating SLE and healthy controls

| Antigen | SEQ ID NO: | Full name/amino acid or oligonucleotide sequence | Manufacture (catalolg no.) |
|---|---|---|---|
| | | NPGAPGSPGPAGQQGAIGSPGPAGPRGPVGPSGPPGKDGTSGHPGPIGPPGPR<br>GNRGERGSEGSPGHPGQPGPPGPPGAPGPCCGGVGAAAIAGIGGEKAGGFAPY<br>YGDEPMDFKINTDEIMTSLKSVNGQIESLISPDGSRKNPARNCRDLKFCHPEL<br>KSGEYWVDPNQGCKLDAIKVFCNMETGETCISANPLNVPRKHWWTDSSAEKKH<br>VWFGESMDGGFQFSYGNPELPEDVLDVHLAFLRLLSSRASQNITYHCKNSIAY<br>MDQASGNVKKALKLMGSNEGEFKAEGNSKFTYTVLEDGCTKHTGEWSKTVFEY<br>RTRKAVRLPIVDIAPYDIGGPDQEFGVDVGPVCFL | |
| U1 snRNP | | Small Nuclear Ribonucleoprotein 70 kDa Human Recombinant | Prospec (pro-445) |
| Ro52 | 3 | 52 kDa Ro protein<br>MASAARLTMMWEEVTCPICLDPFVEPVSIECGHSFCQECISQVGKGGGSVCPV<br>CRQRFLLKNLRPNRQLANMVNNLKEISQEAREGTQGERCAVHGERLHLFCEKD<br>GKALCWVCAQSRKHRDHAMVPLEEAAQEYQEKLQVALGELRRKQELAEKLEVE<br>IAIKRADWKKTVETQKSRIHAEFVQQKNFLVEEEQRQLQELEKDEREQLRILG<br>EKEAKLAQQSQALQELISELDRRCHSSALELLQEVIIVLERSESWNLKDLDIT<br>SPELRSVCHVPGLKKMLRTCAVHITLDPDTANPWLILSEDRRQVRLGDTQQSI<br>PGNEERFDSYPMVLGAQHFHSGKHYWEVDVTGKEAWDLGVCRDSVRRKGHFLL<br>SSKSGFWTIWLWNKQKYEAGTYPQTPLHLQVPPCQVGIFLDYEAGMVSFYNIT<br>DHGSLIYSFSECAFTGPLRPFFSPGFNDGGKNTAPLTLCPLNIGSQGSTDY | Prospec (PRO-328) |
| Sm | | Smith antigen | US Biological (s1014-29F) |
| Apo-SAA | 4 | Recombinant Human Apo-SAA<br>MRSFFSPLGE AFDGARDMWR AYSDMREANY IGSDKYFHAR<br>GNYDAAKRGP GGVWAAEAIS NARENIQRFF GRGAEDSLAD<br>QAANEWGRSG KDPNHFRPAG LPEKY | Peprotec (300-13) |
| H2a | 5 | Histone H2A Human<br>MSGRGKQGGKARAKAKTRSSRAGLQFPVGRVHRLLRKGNYAERVGAGAPVYLA<br>AVLEYLTAEILELAGNAARDNKKTRIIPRHLQLAIRNDEELNKLLGKVTIAQG<br>GVLPNIQAVLLPKKTESHHKAKGK | Sigma (H9250) |
| Oligo21 | 6 | TTA GGG TTA GGG TTA GGG TTA GGG | SBS GenetechCo.,Ltd |

Definitions

It is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The term "about" as used herein means in quantitative terms plus or minus 5%, or in another embodiment plus or minus 10%, or in another embodiment plus or minus 15%, or in another embodiment plus or minus 20%.

The terms "systemic lupus erythematosus", "lupus" and "SLE" as used herein are interchangeable, and generally refer to an autoimmune disease characterized by the criteria set by the 1982 American College of Rheumatology (ACR) for the diagnosis of SLE, and/or by the Systemic Lupus Collaborating Clinics (SLICC) revised criteria, reviewed in Petri et al. (Arthritis and Rheumatism, 2012, Vol. 64, pages 2677-2686).

"An SLE flare" is defined herein as either SLEDAI score >4 or physician assessed flares. The rationale for including physician assessed flares is that the SLEDAI does not cover some rarer manifestations of flares, e.g. gut vasculitis, new onset of peripheral neuropathy.

As used herein, 'incipient flare' means the sub-clinical, beginning, early or emerging stages of a flare.

As used herein, 'quiescent state' means the subject is not experiencing a clinical flare, in the presence or absence of serological indications. About 10% of SLE patients are "clinically quiescent, biochemically active" (i.e. no clinical flare though existing biomarkers suggest the presence of a flare) and another 10% of SLE patients are "clinically active, biochemically quiescent" (i.e. clinical flare though existing biomarkers do not suggest the presence of a flare).

The terms "patient," "individual," or "subject" are used interchangeably herein, and refer to a mammal, particularly, a human. The patient may have mild, intermediate or severe disease. The patient may be treatment naive, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The term "healthy control" as used herein refers to a healthy individual; a plurality of healthy individuals, a data set or value corresponding to or obtained from a healthy individual or a plurality of healthy individuals. According to some embodiments, the control group comprises patients with other rheumatologic disorders or baseline sample from same patient.

As used herein the term "reference control" means a value that statistically correlates to a particular outcome when compared to an assay result. The reference value may be a threshold score value or a cutoff score value. Typically a reference value will be a threshold above which one outcome is more probable and below which an alternative threshold is more probable.

The terms "measuring", "detecting" and "determining" are used interchangeably throughout, and refer to methods which include obtaining a patient sample and detecting reactivity of antibodies in a sample. In some embodiments, the terms refer to obtaining a patient sample and detecting the reactivity of antibodies in the sample to one or more antigens. Measuring can be accomplished by methods known in the art and those further described herein.

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of SLE. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, cerebrospinal fluid, urine, saliva, stool and synovial fluid). In a specific embodiment, a sample comprises a blood sample. In another embodiment, a serum sample is used. The definition also includes samples that have been manipulated in any way after their procurement, such as by centrifugation, filtration, precipitation, dialysis, chromatography, treatment with reagents, washed or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry. The samples may be tested immediately after collection, after storage at RT, 4 degrees, −20 degrees, or −80 degrees Celsius. After storage for 24 hours, 1 week, 1 month, 1 year, 10 years or up to 30 years.

As used herein, the term "autoantibodies" refers to antibodies that are capable of reacting against an antigenic constituent of an individual's own tissue or cells (e.g., the antibodies recognize and bind to "self-antigens").

Unless otherwise indicated, the term "oligonucleotide antigen" as used herein relates to a nucleotide sequence of between 15 and 40 nucleotides in length, alternatively between 17 and 28 nucleotides in length, or between 18-25 nucleotides in length. In certain embodiments, an oligonucleotide antigen consists of at least 4, at least 5, at least 6, at least 7, at least 8, at least 9, at least 10, at least 16, at least 24, or more contiguous nucleotides. Each possibility represents a separate embodiment of the invention. In certain embodiments, an antigen consists of not more than 50, not more than 45, not more than 40, not more than 35, not more than 30, not more than 25, not more than 20, not more than 16, or less contiguous nucleotides. Each possibility represents a separate embodiment of the invention. In certain embodiments, an antigen consists of 10-30, 15-25 or 17-20 contiguous nucleotides. In certain embodiments, an antigen consists of 17, 18, 19 or 20 contiguous nucleotides.

The nomenclature used to refer to the oligonucleotide sequence of the oligonucleotide antigen disclosed in the present invention is as follows: an oligonucleotide antigen consisting of the oligonucleotide sequence of $X_2Y_3Z_2$, i.e. two oligonucleotides of X followed by three oligonucleotides of Y followed by two oligonucleotides of Z is labeled as X2Y3Z2, (X)2(Y)3(Z)2, or XXYYYZZ, or referred to by its corresponding SEQ ID NO. It should be understood that in this example, X, Y and Z may relate to more than one oligonucleotide, e.g. to 2-20 oligonucleotides. Therefore, an oligonucleotide antigen consisting of the oligonucleotide sequence of $X_2$, wherein X is a stretch of e.g. two oligonucleotides, e.g. YZ, is labeled as X2, (X)2, or YZYZ, or referred to by its corresponding SEQ ID NO.

Unless otherwise indicated, the terms "peptide antigen" as used herein relate to an amino-acid sequence of between 15 and 40 amino-acids in length, alternatively between 17 and 28 amino-acids in length, or between 18-25 amino-acids in length. In certain embodiments, a peptide antigen consists of at least 4, at least 5, at least 6, at least 7, at least 8, at least 9, at least 10, at least 16, or more contiguous amino-acids. Each possibility represents a separate embodiment of the invention. In certain embodiments, an antigen consists of not more than 50, not more than 45, not more than 40, not more than 35, not more than 30, not more than 25, not more than 20, not more than 16, or less contiguous amino-acids. Each possibility represents a separate embodiment of the invention. In certain embodiments, an antigen consists of 10-30, 15-25 or 17-20 contiguous amino-acids. In certain embodiments, an antigen consists of 17, 18, 19 or 20 contiguous amino-acids.

As defined herein, "U1 SnRNP" refers to a ribonuclear protein, which is conserved between species. In a particular embodiment, Small Nuclear Ribonucleoprotein 70 kDa Human Recombinant (U1 SnRNP) is commercially available, e.g., from Prospec, catalog number pro-445.

"DNAse I" is considered the major serum nuclease. DNAse I is the founding member of the DNAse I-like family of divalent cation-dependent endonucleases. In a particular embodiment, DNAse I antigen is commercially available, e.g., from AKRON biotech, catalog number AK3778.

"Histones" are the chief protein components of chromatin. They act as spools around which DNA winds and they play a role in gene regulation. Six major histone classes are known: H1 (sometimes called the linker histone; also related to Histone H5); H2A; H2B; H3; H4; and archaeal histones. Two each of the class H2A, H2B, H3 and H4, so-called core histones, assemble to form one octameric nucleo some core particle by wrapping 146 base pairs of DNA around the protein spool in 1.65 left-handed super-helical turn. The linker histone H1 binds the nucleosome and the entry and exit sites of the DNA, thus locking the DNA into place and allowing the formation of higher order structure. The most basic such formation is the 10 nm fiber or beads on a string conformation. This involves the wrapping of DNA around nucleosomes with approximately 50 base pairs of DNA spaced between each nucleosome (also referred to as linker DNA). The assembled histones and DNA is called chromatin. Higher order structures include the 30 nm fiber (forming an irregular zigzag) and 100 nm fiber, these being the structures found in normal cells. During mitosis and meiosis, the condensed chromosomes are assembled through interactions between nucleosomes and other regulatory proteins. In a particular embodiment, Histone H2A human antigen is commercially available, e.g., from Sigma Aldrich, catalog number H9250. In another particular embodiment, Histone Type III-S calf antigen is commercially available, e.g., from Sigma Aldrich, catalog number H5505.

Single Strand Deoxyribonucleic Acid (ssDNA)

The reactivity of antibodies to the ssDNA antigen may be determined according to techniques known in the art. The ssDNA antigen may be obtained from any source, such as but not limit to, calf, human, horse, pig or bovine source. In a particular embodiment, ssDNA has a CAS number of 91080-16-9. The ssDNA antigen is commercially available, e.g., from Sigma Aldrich, catalog number D8899.

Collagen Type III

Type III collagen is the second most abundant collagen in human tissues and occurs particularly in tissues exhibiting elastic properties, such as skin, blood vessels and various internal organs. Mutations of type III collagen cause the most severe form of Ehlers-Danlos syndrome, EDS IV, which affect arteries, internal organs, joints and skin, and may cause sudden death when the large arteries rupture. In a particular embodiment, the type III collagen antigen of the present invention is a Bornstein and Traub Type III collagen, e.g., from human placenta. The reactivity of antibodies to the collagen-III antigen may be determined according to techniques known in the art. In a particular embodiment, collagen-III has a CAS number of 9007-34-5. The collagen-III antigen is commercially available, e.g., from Sigma Aldrich, catalog number C4407.

Ro52

The function of the Ro52 protein has not been fully established, although a role in ubiquitination and other regulatory processes has been proposed. Ro52 includes several predicted functional domains; two zinc-finger motifs are situated in the N-terminal region and a SPRY-region is near the C-terminus. The central part of Ro52 consists of a coiled-coil region, including a leucine zipper comprising amino acid (aa) residues 200-232. Leucine zippers, which contain periodic repeats of leucine amino acids every seventh residue, give rise to a helical structure, and are likely to be of importance for the correct folding of the protein, as well as its interaction with other molecules. Based on an analysis of sequence similarity, the 475 amino acid (aa) protein Ro52 belongs to the tripartite motif (TRIM) family. In a particular embodiment, the Ro52 antigen is commercially available, e.g., from Prospec catalog number PRO-328.

Sm

Sm antigen is a non-histone nuclear protein composed of several polypeptides of differing molecular weights. They include B (26 kD), B'(27 kD), and D (13 kD). The principle reactivity has been shown to reside in the B, B', and D polypeptides. The Sm antigen is involved in normal post-transcriptional, premessenger RNA processing to excise introns. It has been demonstrated that the Sm antigenicity is both RNase and DNase resistant and partially resistant to tryptic digestion. In a particular embodiment, the Sm antigen is commercially available, e.g., from US Biological catalog number s1014-29F.

Apo-SAA

Human Apo-SAA is a 104 amino acid polypeptide that circulates primarily in association with high-density lipoproteins (HDL). The level of Apo-SAA, normally 1-5 µg/ml in plasma, increases 500-1000 fold within 24 hours of an inflammatory stimulus and, under these conditions, is the most abundant HDL apolipoprotein. The human SAA gene codes for a 122 amino acid polypeptide, which contains an 18 amino acid N-terminal signal sequence. Recombinant Apo-SAA is a consensus SAA molecule corresponding to human Apo-SAA1α, except for the presence of an N-terminal methionine, the substitution of asparagine for aspartic acid at position 60, and arginine for histidine at position 71 (the latter two substituted residues are present in Apo-SAA2β). The calculated molecular weight of Recombinant Human Apo-SAA is 11.7 kDa. In a particular embodiment, the Apo-SAA antigen is commercially available, e.g., from Peprotec catalog number 300-13.

In terms of "functional analogues", it is well understood by those skilled in the art, that inherent in the definition of a biologically functional polypeptide or peptide analogue is the concept that there is a limit to the number of changes that may be made within a defined portion of the molecule and still result in a molecule with an acceptable level of equivalent biological activity. A plurality of distinct polypeptides or peptides with different substitutions may easily be made and used in accordance with the invention. It is also understood that certain residues are particularly important to the biological or structural properties of a polypeptide, and such residues may not generally be exchanged.

Functional analogues can be generated by conservative or non-conservative amino acid substitutions. Amino acid substitutions are generally based on the relative similarity of the amino acid side-chain substituents, for example, their hydrophobicity, hydrophilicity, charge, size and the like. Thus, within the scope of the invention, conservative amino acid changes means, an amino acid change at a particular position which is of the same type as originally present; i.e. a hydrophobic amino acid exchanged for a hydrophobic amino acid, a basic amino acid for a basic amino acid, etc. Examples of conservative substitutions include the substitution of non-polar (hydrophobic) residues such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another, the substitution of a branched chain amino acid, such as isoleucine, leucine, or valine for another, the substitution of one aromatic amino acid, such as phenylalanine, tyrosine or tryptophan for another. Such amino acid changes result in functional analogues in that they do not significantly alter the overall charge and/or configuration of the polypeptide. Examples of such conservative changes are well-known to the skilled artisan and are within the scope of the present invention. Conservative substitution also includes the use of a chemically derivatized residue in place of a non-derivatized residue provided that the resulting polypeptide is a biologically functional equivalent to the polypeptide antigens.

As used herein, the "reactivity of antibodies in a sample" or "reactivity of an antibody in a sample" to "an antigen" or to "a plurality of antigens" refers to the immune reactivity of at least one antibody in the sample to at least one specific antigen selected from the plurality of antigens. The immune reactivity of the antibody to the antigen, i.e. its ability to specifically bind the antigen, may be used to determine the amount of the antibody in the sample. The calculated levels of each one of the tested antibodies in the sample are collectively referred to as the reactivity pattern of the sample to these antigens. The reactivity pattern of the sample reflects the levels of each one of the tested antibodies in the sample, thereby providing a quantitative assay. In a preferred embodiment, the antibodies are quantitatively determined.

A "significant difference" between reactivity patterns refers, in different embodiments, to a statistically significant difference, or in other embodiments to a significant difference as recognized by a skilled artisan. In yet another preferred embodiment, a significant (quantitative) difference between the reactivity pattern of the sample obtained from the subject compared to the control reactivity pattern is an indication that the subject is afflicted with SLE. In specific embodiments, up-regulation or higher reactivity of the reactivity of an antibody in a sample to an antigen refers to an increase (i.e., elevation) of about at least two, about at least three, about at least four, or about at least five times higher (i.e., greater) than the reactivity levels of the antibody to the antigen in the control. In another embodiment, down-regulation or lower reactivity of the reactivity of an antibody in a sample to an antigen refers to a decrease (i.e., reduction) of about at least two, about at least three, about at least four, or about at least five times lower than the reactivity levels of the antibody to the antigen in the control.

In particular embodiments, said significant difference is determined using a cutoff of a positive predictive value (PPV) of at least 70%, at least 85%, at least 90%. Determining a PPV for a selected marker (e.g., an antigen) is well known to the ordinarily skilled artisan and is exemplified in the methods described below. Typically, positivity for an antigen is determined if it detected above 10% of the subjects in a specific study subgroup using a selected cutoff value, such as PPV≥90%. For example, antigen i is determined to specifically characterize group A if it detected at least 10% of the subjects in group A with a PPV≥90% when compared to a different test group B. Subjects in group A that are above the cutoff of PPV≥90% for antigen i are considered to be positive for antigen i.

An antibody "directed to" an antigen, as used herein is an antibody which is capable of specifically binding the antigen. Determining the levels of antibodies directed to a plurality of antigens includes measuring the level of each antibody in the sample, wherein each antibody is directed to a specific antigen, including but not limited to, an antigen selected from Table 1. This step is typically performed using an immunoassay, as detailed herein.

In other embodiments, determining the reactivity of antibodies in said sample to said plurality of antigens, (and the levels of each one of the tested antibodies in the sample) is performed by a process comprising contacting the sample, under conditions such that a specific antigen-antibody complex may be formed, with an antigen probe set comprising said plurality of antigens, and quantifying the amount of antigen-antibody complex formed for each antigen probe. The amount of antigen-antibody complex is indicative of the level of the tested antibody in the sample (or the reactivity of the sample with the antigen).

In another embodiment the method comprises determining the reactivity of at least one IgG antibody and at least one IgM antibody in the sample to the plurality of antigens. In another embodiment, the method comprises determining the reactivity of a plurality of IgG antibodies and at least one IgM antibody in the sample to the plurality of antigens. In another embodiment, the method comprises determining the reactivity of at least one IgG antibody and a plurality of IgM antibodies in the sample to the plurality of antigens. According to another embodiment, the method comprises determining the reactivity of antibodies in the sample to a plurality of oligonucleotide antigens.

The reactivity of antibodies to the plurality of the antigens may be determined according to techniques known in the art. Typically, determining the reactivity of antibodies in the sample to the plurality of antigens is performed using an immunoassay. Advantageously, the plurality of antigens may be used in the form of an antigen array.

Antigen Probes and Antigen Probe Sets

According to further embodiments, the invention provides antigen probes and antigen probe sets useful for diagnosing SLE, as detailed herein.

The invention further provides a plurality of antigens also referred to herein as antigen probe sets. These antigen probe sets comprise a plurality of antigens which are reactive specifically with the sera of subjects having SLE. According to the principles of the invention, the plurality of antigens may advantageously be used in the form of an antigen array. According to some embodiments the antigen array is conveniently arranged in the form of an antigen chip.

A "probe" as used herein means any compound capable of specific binding to a component. According to one aspect, the present invention provides an antigen probe set comprising a plurality of antigens selected from Table 1. In one embodiment, said plurality of antigens is selected from the group consisting of: ssDNA, Sm, DNAse I, Histone III-S, Ro52, U1 snRNP, Collagen III, Apo-SAA, H2a and Oligo21, or any combinations or subset thereof.

As exemplified herein below, a subject suspected of having SLE can be differentiated from healthy controls by assaying and determining IgG and/or IgM antibody reactivities in a sample obtained from said subject. The reactivity of antibodies to the plurality of antigens of the invention may be determined according to techniques known in the art. Further, the antigens used in the present invention are known in the art and are commercially available, e.g., from Prospec or Sigma-Aldrich.

Preferably, the plurality of antigens of the methods and kits of the invention comprises a set of the antigens as disclosed herein. Yet in other embodiments, the plurality of antigens (or the antigen probe set) comprises or consists of a subset thereof, e.g. at least 2, 3, 4, 5, 6, 7, 8, 9 or 10 different antigens, each selected from the antigens of the present invention. Each possibility represents a separate embodiment of the invention. Such subsets may be selected so as to result in optimal sensitivity and/or specificity of the diagnostic assay.

Antigen probes to be used in the assays of the invention may be purified or synthesized using methods well known in the art. For example, an antigenic protein or peptide may be produced using known recombinant or synthetic methods, including, but not limited to, solid phase (e.g. Boc or f-Moc chemistry) and solution phase synthesis methods (Stewart and Young, 1963; Meienhofer, 1973; Schroder and Lupke, 1965; Sambrook et al., 2001). One of skill in the art will possess the required expertise to obtain or synthesize the antigen probes of the invention. Table 1 lists the SLE-related antigens of the invention as well as a non-limiting characterization of said antigens. Some antigen probes are also commercially available, e.g. from Prospec (Ness-Ziona, Israel) or Sigma Aldrich or additional manufactures listed in Table 1.

It should be noted, that the invention utilizes antigen probes as well as homologs, fragments, isoforms, partial sequences, mutant forms, post translationally modified forms, and derivatives thereof, as long as these homologs, fragments, isoforms, partial sequences, mutant forms, post translationally modified forms and derivatives are immunologically cross-reactive with these antigen probes. The term "immunologically cross-reactive" as used herein refers to two or more antigens that are specifically bound by the same antibody. The term "homolog" as used herein refers to a peptide or oligonucleotide which having at least 70%, at least 75%, at least 80%, at least 85% or at least 90% identity to the antigen's amino acid or nucleotide sequence. Cross-reactivity can be determined by any of a number of immunoassay techniques, such as a competition assay (measuring the ability of a test antigen to competitively inhibit the binding of an antibody to its known antigen).

The term "fragment" as used herein refers to a portion of a polypeptide, or polypeptide analog which remains immunologically cross-reactive with the antigen probes, e.g., to recognize immuno-specifically the target antigen. The fragment may have the length of about 40%, about 50%, about 60%, about 70%, about 80%, about 85%, about 90% or about 95% of the respective antigen.

The term peptide typically refers to a polypeptide of up to about 50 amino acid residues in length. According to particular embodiments, the antigenic peptides of the invention may be about 10-100, 10-80, 10-75, 10-50 or about 10-30 amino acids in length.

The term encompasses native peptides (including degradation products, synthetically synthesized peptides, or recombinant peptides), peptidomimetics (typically, synthetically synthesized peptides), and the peptide analogues peptoids and semipeptoids, and may have, for example, modifications rendering the peptides more stable while in a body or more capable of penetrating into cells. Such modifications include, but are not limited to: N-terminus modifications; C-terminus modifications; peptide bond modifications, including but not limited to $CH_2$—NH, CH—S, $CH_2$—S=O, O=C—NH, $CH_2$—O, $CH_2$—$CH_2$, S=C—NH, CH=CH, and CF=CH; backbone modifications; and residue modifications. According to some embodiments, the peptide antigens of the invention are BSA-conjugated peptides.

The antigens of the invention may be used having a terminal carboxy acid, as a carboxy amide, as a reduced terminal alcohol or as any pharmaceutically acceptable salt, e.g., as metal salt, including sodium, potassium, lithium or calcium salt, or as a salt with an organic base, or as a salt with a mineral acid, including sulfuric acid, hydrochloric acid or phosphoric acid, or with an organic acid e.g., acetic acid or maleic acid.

Functional derivatives consist of chemical modifications to amino acid side chains and/or the carboxyl and/or amino moieties of said peptides. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives, are those polypeptides, which contain one or more naturally occurring or modified amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

The amino acid residues described herein are in the "L" isomeric form, unless otherwise indicated. However, residues in the "D" isomeric form can be substituted for any L-amino acid residue, as long as the peptide substantially retains the desired antibody specificity.

Suitable analogs may be readily synthesized by nowstandard peptide synthesis methods and apparatus or recombinant methods. All such analogs will essentially be based on the antigens of the invention as regards their amino acid sequence but will have one or more amino acid residues deleted, substituted or added. When amino acid residues are substituted, such conservative replacements which are envisaged are those which do not significantly alter the structure or antigenicity of the polypeptide. For example basic amino acids will be replaced with other basic amino acids, acidic ones with acidic ones and neutral ones with neutral ones. In addition to analogs comprising conservative substitutions as detailed above, analogs comprising non-conservative amino acid substitutions are further contemplated, as long as these analogs are immunologically cross reactive with an antigen of the invention.

In other aspects, there are provided nucleic acids encoding these peptides, vectors comprising these nucleic acids and host cells containing them. These nucleic acids, vectors and host cells are readily produced by recombinant methods known in the art (see, e.g., Sambrook et al., 2001). For example, an isolated nucleic acid sequence encoding an antigen of the invention can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional peptide of the present invention.

According to the principles of the invention the kits comprise a plurality of antigens also referred to herein as antigen probe sets. These antigen probe sets comprising a plurality of antigens are reactive specifically with the sera of subjects having SLE. According to the principles of the invention, the plurality of antigens may advantageously be used in the form of an antigen array. According to some embodiments the antigen array is conveniently arranged in the form of an antigen chip.

According to another aspect, the present invention provides an article of manufacture comprising the at least one of the antigen probe sets described above.

In certain embodiments, the article of manufacture is in the form of an antigen probe array or in the form of an antigen chip or in the form of a dipstick or in the form of a lateral flow test or any other platform known to those skilled in the art. An "antigen probe array" generally refers to a plurality of antigen probes, either mixed in a single container or arranges in to or more containers. An "antigen chip" generally refers to a substantially two dimensional surface, onto which a plurality of antigens are attached or adhered. A "dipstick" generally refers to an object, onto which a plurality of antigens are attached or adhered, which is dipped into a liquid to perform a chemical test or to provide a measure of quantity found in the liquid. A "lateral flow test" generally refers to devices intended to detect the presence (or absence) of a target analyte in sample (matrix) without the need for specialized and costly equipment. In certain embodiments, the article of manufacture is in the form of a kit.

According to certain embodiments, the kit further comprises means for determining the reactivity of antibodies in a sample to at least one antigen of the plurality of antigens. According to another embodiment, the kit further comprises means for comparing reactivity of antibody in different samples to at least one antigen of the plurality of antigens. According to another embodiment, the kit further comprises instructions for use. For example, the aforementioned means may include reagents, detectable labels and/or containers which may be used for measuring specific binding of antibodies to the antigen probes of the invention. "Means" as used herein may also refer to devices, reagents and chemicals, such as vials, buffers and written protocols or instructions, used to perform biological or chemical assays.

In other embodiments, the kit may further comprise means for determining the reactivity of antibodies in a sample to the plurality of antigens. For example, the kit may contain reagents, detectable labels and/or containers which may be used for measuring specific binding of antibodies to the antigen probes of the invention. In a particular embodiment, said kit is in the form of an antigen array. In some embodiments, said kit comprises means for comparing reactivity patterns of antibodies in different samples to the plurality of antigens. In other embodiments, said kit may further comprise negative and/or positive control samples.

For example, a negative control sample may contain a sample from at least one healthy individual (e.g., an individual not-afflicted with SLE). A positive control may contain a sample from at least one individual afflicted with SLE, or a subtype of SLE which is being diagnosed. Other non-limiting examples are a panel of control samples from a set of healthy individuals or diseased individuals, or a stored set of data from control individuals.

Antibodies, Samples and Immunoassays

Antibodies, or immunoglobulins, comprise two heavy chains linked together by disulfide bonds and two light chains, each light chain being linked to a respective heavy chain by disulfide bonds in a "Y" shaped configuration. Each heavy chain has at one end a variable domain (VH) followed by a number of constant domains (CH). Each light chain has a variable domain (VL) at one end and a constant domain (CL) at its other end, the light chain variable domain being aligned with the variable domain of the heavy chain and the light chain constant domain being aligned with the first constant domain of the heavy chain (CH1). The variable domains of each pair of light and heavy chains form the antigen binding site.

The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, k) found in all antibody classes.

It should be understood that when the terms "antibody" or "antibodies" are used, this is intended to include intact antibodies, such as polyclonal antibodies or monoclonal antibodies (mAbs), as well as proteolytic fragments thereof such as the Fab or F(ab')$_2$ fragments. Further included within the scope of the invention (for example as immunoassay reagents, as detailed herein) are chimeric antibodies; recombinant and engineered antibodies, and fragments thereof.

Exemplary functional antibody fragments comprising whole or essentially whole variable regions of both light and heavy chains are defined as follows: (i) Fv, defined as a genetically engineered fragment consisting of the variable region of the light chain and the variable region of the heavy chain expressed as two chains; (ii) single-chain Fv ("scFv"), a genetically engineered single-chain molecule including the variable region of the light chain and the variable region of the heavy chain, linked by a suitable polypeptide linker; (iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof; (iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

The term "antigen" as used herein is a molecule or a portion of a molecule capable of being bound by an antibody. The antigen is typically capable of inducing an animal to produce antibody capable of binding to an epitope of that antigen. An antigen may have one or more epitopes. The specific reaction referred to above is meant to indicate that the antigen will react, in a highly selective manner, with its corresponding antibody and not with the multitude of other antibodies which may be evoked by other antigens. An "antigenic peptide" is a peptide which is capable of specifically binding an antibody.

In another embodiment, detection of the capacity of an antibody to specifically bind an antigen probe may be performed by quantifying specific antigen-antibody complex formation. The term "specifically bind" as used herein means that the binding of an antibody to an antigen probe is not competitively inhibited by the presence of non-related molecules.

In certain embodiments, the method of the present invention is performed by determining the capacity of an antigen of the invention to specifically bind antibodies of the IgG isotype, or, in other embodiments, antibodies of the IgM, isolated from a subject.

Methods for obtaining suitable antibody-containing biological samples from a subject are well within the ability of those of skill in the art. Typically, suitable samples comprise whole blood and products derived therefrom, such as plasma and serum. In other embodiments, other antibody-containing samples may be used, e.g. CSF, urine and saliva samples.

Numerous well known fluid collection methods can be utilized to collect the biological sample from the subject in order to perform the methods of the invention.

In accordance with the present invention, any suitable immunoassay can be used with the subject peptides. Such techniques are well known to the ordinarily skilled artisan and have been described in many standard immunology manuals and texts. In certain preferable embodiments, determining the capacity of the antibodies to specifically bind the antigen probes is performed using an antigen probe array-based method. Preferably, the array is incubated with suitably diluted serum of the subject so as to allow specific binding between antibodies contained in the serum and the immobilized antigen probes, washing out unbound serum from the array, incubating the washed array with a detectable label-conjugated ligand of antibodies of the desired isotype, washing out unbound label from the array, and measuring levels of the label bound to each antigen probe.

In various embodiments, the method of the present invention further comprises diluting the sample before performing the determining step. In one embodiment, the sample is diluted 1:2, for instance, using PBS. In another embodiment, the sample is diluted 1:4, 1:6, 1:8, 1:15, 1:20, 1:50, or preferably 1:10. Each possibility represents a separate embodiment of the present invention. In another embodiment, the sample is diluted in the range of times 2-times 10. In another embodiment, the sample is diluted in the range of times 4-times 10. In another embodiment, the sample is diluted in the range of times 6-times 10. In another embodiment, the sample is diluted in the range of times 8-times 10.

The Antigen Chip

Antigen microarrays are used for the high-throughput characterization of the immune response (Robinson et al., 2002, *Nat Med* 8, 295-301), and have been used to analyze immune responses in vaccination and in autoimmune disorders (Robinson et al., 2002; Robinson et al., 2003, *Nat Biotechnol.* 21, 1033-9; Quintana et al., 2004; Kanter et al., 2006, *Nat Med* 12, 138-43). It has been hypothesized, that patterns of multiple reactivities may be more revealing than single antigen-antibody relationships (Quintana et al., 2006, *Lupus* 15, 428-30) as shown in previous analyses of autoimmune repertoires of mice (Quintana et al., 2004; Quintana et al., 2001, *J Autoimmun* 17, 191-7) and humans (Merbl et al., 2007, *J Clin Invest* 117, 712-8; Quintana et al., 2003, *J Autoimmun* 21, 65-75) in health and disease. Thus, autoantibody repertoires have the potential to provide both new insights into the pathogenesis of the disease and to serve as immune biomarkers (Cohen, 2007, *Nat Rev Immunol.* 7, 569-74) of the disease process.

According to some aspects the methods of the present invention may be practiced using antigen arrays as disclosed in WO 02/08755 and U.S. 2005/0260770, the contents of which are incorporated herein by reference. WO 02/08755 is directed to a system and an article of manufacture for clustering and thereby identifying predefined antigens reactive with undetermined immunoglobulins of sera derived from patient subjects in need of diagnosis of disease or monitoring of treatment. Further disclosed are diagnostic methods, and systems useful in these methods, employing the step of clustering a subset of antigens of a plurality of antigens, said subset of antigens being reactive with a plurality of antibodies being derived from a plurality of patients, and associating or disassociating the antibodies of a subject with the resulting cluster.

U.S. Pat. App. Pub. No. 2005/0260770 discloses an antigen array system and diagnostic uses thereof. The application provides a method of diagnosing an immune disease, particularly diabetes type 1, or a predisposition thereto in a subject, comprising determining a capacity of immunoglobulins of the subject to specifically bind each antigen probe of an antigen probe set. The teachings of said disclosures are incorporated in their entirety as if fully set forth herein.

In other embodiments, various other immunoassays may be used, including, without limitation, enzyme-linked immunosorbent assay (ELISA), flow cytometry with multiplex beads (such as the system made by Luminex), surface plasmon resonance (SPR), elipsometry, and various other immunoassays which employ, for example, laser scanning, light detecting, photon detecting via a photo-multiplier, photographing with a digital camera based system or video system, radiation counting, fluorescence detecting, electronic, magnetic detecting and any other system that allows quantitative measurement of antigen-antibody binding.

Various methods have been developed for preparing arrays suitable for the methods of the present invention. State-of-the-art methods involves using a robotic apparatus to apply or "spot" distinct solutions containing antigen probes to closely spaced specific addressable locations on the surface of a planar support, typically a glass support, such as a microscope slide, which is subsequently processed by suitable thermal and/or chemical treatment to attach antigen probes to the surface of the support. Conveniently, the glass surface is first activated by a chemical treatment that leaves a layer of reactive groups such as epoxy groups on the surface, which bind covalently any molecule containing free amine or thiol groups. Suitable supports may also include silicon, nitrocellulose, paper, cellulosic supports and the like.

Preferably, each antigen probe, or distinct subset of antigen probes of the present invention, which is attached to a specific addressable location of the array is attached independently to at least two, more preferably to at least three separate specific addressable locations of the array in order to enable generation of statistically robust data.

According to additional embodiments, the antigen probe set comprises at least 2, at least 3, at least 5, at least 10, at least 50, at least 100, at least 150, at least 200, at least 300 or more antigens, including one or a plurality of the antigens provided by the present invention. According to additional embodiments, the antigen probe set comprises at least 1, at least 6, at least 10, at least 100, at least 150, at least 200, or more oligonucleotide antigens, including one or a plurality of the oligonucleotide antigens provided by the present invention.

In addition to antigen probes of the invention, the array may advantageously include control antigen probes or other standard chemicals. Such control antigen probes may include normalization control probes. The signals obtained from the normalization control probes provide a control for variations in binding conditions, label intensity, "reading" efficiency and other factors that may cause the signal of a given binding antibody-probe ligand interaction to vary. For example, signals, such as fluorescence intensity, read from all other antigen probes of the antigen probe array are divided by the signal (e.g., fluorescence intensity) from the normalization control probes thereby normalizing the measurements.

Normalization control probes can be bound to various addressable locations on the antigen probe array to control for spatial variation in antibody-ligand probe efficiency. Preferably, normalization control probes are located at the corners or edges of the array to control for edge effects, as well as in the middle of the array.

The labeled antibody ligands may be of any of various suitable types of antibody ligand. Preferably, the antibody ligand is an antibody which is capable of specifically binding the Fc portion of the antibodies of the subject used. For example, where the antibodies of the subject are of the IgM isotype, the antibody ligand is preferably an antibody capable of specifically binding to the Fc region of IgM antibodies of the subject.

The ligand of the antibodies of the subject may be conjugated to any of various types of detectable labels. Preferably the label is a fluorophore, most preferably Cy3. Alternately, the fluorophore may be any of various fluorophores, including Cy5, fluorescein isothiocyanate (FITC), phycoerythrin (PE), rhodamine, Texas red, and the like. Suitable fluorophore-conjugated antibodies specific for antibodies of a specific isotype are widely available from commercial suppliers and methods of their production are well established.

Antibodies of the subject may be isolated for analysis of their antigen probe binding capacity in any of various ways, depending on the application and purpose. While the subject's antibodies may be suitably and conveniently in the form of blood serum or plasma or a dilution thereof (e.g. 1:10 dilution), the antibodies may be subjected to any desired degree of purification prior to being tested for their capacity to specifically bind antigen probes. The method of the present invention may be practiced using whole antibodies of the subject, or antibody fragments of the subject which comprises an antibody variable region.

Data Analysis

Advantageously, the methods of the invention may employ the use of learning and pattern recognition analyzers, clustering algorithms and the like, in order to discriminate between reactivity patterns of healthy control subjects to those of patients having SLE. As such, this term specifically includes a difference measured by, for example, determining the reactivity of antibodies in a test sample to a plurality of antigens, and comparing the resulting reactivity pattern to the reactivity patterns of negative and positive control samples (e.g. samples obtained from control subjects which are not afflicted with SLE or patients afflicted with SLE, respectively) using such algorithms and/or analyzers. The difference may also be measured by comparing the reactivity pattern of the test sample to a predetermined classification rule obtained in such manner.

In some embodiments, the methods of the invention may employ the use of learning and pattern recognition analyzers, clustering algorithms and the like, in order to discriminate between reactivity patterns of subjects having a subtype of SLE to control subjects. For example, the methods may include determining the reactivity of antibodies in a test sample to a plurality of antigens, and comparing the resulting pattern to the reactivity patterns of negative and positive control samples using such algorithms and/or analyzers.

Thus, in another embodiment, a significant difference between the reactivity pattern of a test sample compared to a reactivity pattern of a control sample, wherein the difference is computed using a learning and pattern recognition algorithm, indicates that the subject is afflicted with SLE. For example, the algorithm may include, without limitation, supervised or non-supervised classifiers including statistical algorithms including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor, artificial neural networks, coupled two-way clustering algorithms, multi-layer perceptrons (MLP), generalized regression neural network (GRNN), fuzzy inference systems (FIS), self-organizing map (SOM), genetic algorithms (GAS), neuro-fuzzy systems (NFS), adaptive resonance theory (ART).

In certain embodiments, the learning and pattern recognition algorithm is SVM. In machine learning, support vector machines (SVMs, also support vector networks) are supervised learning models with associated learning algorithms that analyze data and recognize patterns, used for classification and regression analysis. Given a set of training examples, each marked as belonging to one of two categories, an SVM training algorithm builds a model that assigns new examples into one category or the other, making it a non-probabilistic binary linear classifier. An SVM model is a representation of the examples as points in space, mapped so that the examples of the separate categories are divided by a clear gap that is as wide as possible. New examples are then mapped into that same space and predicted to belong to a category based on which side of the gap they fall on.

In certain embodiments, the learning and pattern recognition algorithm is logistic regression (LR). In statistics, logistic regression, or logit regression, or logit model is a type of probabilistic statistical classification model. It is also used to predict a binary response from a binary predictor, used for predicting the outcome of a categorical dependent variable (i.e., a class label) based on one or more predictor variables (features). That is, it is used in estimating the parameters of a qualitative response model. The probabilities describing the possible outcomes of a single trial are modeled, as a function of the explanatory (predictor) variables, using a logistic function. Frequently "logistic regression" is used to refer specifically to the problem in which the dependent variable is binary, that is, the number of available categories is two.

"Logistic regression" is part of a category of statistical models called generalized linear models. Logistic regression allows one to predict a discrete outcome, such as group membership, from a set of variables that may be continuous, discrete, dichotomous, or a mix of any of these. The dependent or response variable is dichotomous, for example, one of two possible types of cancer. Logistic regression models the natural log of the odds ratio, i.e., the ratio of the probability of belonging to the first group (P) over the probability of belonging to the second group (1-P), as a linear combination of the different expression levels (in log-space) and of other explaining variables. The logistic regression output can be used as a classifier by prescribing that a case or sample will be classified into the first type if P is greater than 0.5 or 50%. Alternatively, the calculated probability P can be used as a variable in other contexts such as a 1D or 2D threshold classifier.

In certain embodiments, the learning and pattern recognition algorithm is linear discriminant analysis (LDA). LDA and the related Fisher's linear discriminant are methods used in statistics, pattern recognition and machine learning to find a linear combination of features which characterizes or separates two or more classes of objects or events. The resulting combination may be used as a linear classifier or, more commonly, for dimensionality reduction before later classification.

In certain embodiments, the learning and pattern recognition algorithm is Quadratic Discriminant analysis (QDA). A quadratic classifier is used in machine learning and statistical classification to separate measurements of two or more classes of objects or events by a quadric surface. It is a more general version of the linear classifier. QDA is closely related to LDA, where it is assumed that the measurements from each class are normally distributed. Unlike LDA however, in QDA there is no assumption that the covariance of each of the classes is identical. When the normality assumption is true, the best possible test for the hypothesis that a given measurement is from a given class is the likelihood ratio test.

In certain embodiments, the learning and pattern recognition algorithm is Classification and Decision Tree (CART). Decision tree learning uses a decision tree as a predictive model which maps observations about an item to conclusions about the item's target value. It is one of the predictive modelling approaches used in statistics, data mining and machine learning. Tree models where the target variable can take a finite set of values are called classification trees. In these tree structures, leaves represent class labels and branches represent conjunctions of features that lead to those class labels.

In certain embodiments, the learning and pattern recognition algorithm is random forest. Random forests are an ensemble learning method for classification, regression and other tasks, that operate by constructing a multitude of decision trees at training time and outputting the class that is the mode of the classes (classification) or mean prediction (regression) of the individual trees. Random forests correct for decision trees' habit of over fitting to their training set.

In certain embodiments, one or more algorithms or computer programs may be used for comparing the amount of each antibody quantified in the test sample against a predetermined cutoff (or against a number of predetermined cutoffs). Alternatively, one or more instructions for manually performing the necessary steps by a human can be provided.

Algorithms for determining and comparing pattern analysis include, but are not limited to, principal component analysis, Fischer linear analysis, neural network algorithms, genetic algorithms, fuzzy logic pattern recognition, and the like. After analysis is completed, the resulting information can, for example, be displayed on display, transmitted to a host computer, or stored on a storage device for subsequent retrieval.

Many of the algorithms are neural network based algorithms. A neural network has an input layer, processing layers and an output layer. The information in a neural network is distributed throughout the processing layers. The processing layers are made up of nodes that simulate the neurons by the interconnection to their nodes. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In some embodiments, the Fisher linear discriminant analysis (FLDA) and canonical discriminant analysis (CDA) as well as combinations thereof are used to compare the output signature and the available data from the database.

In other embodiments, principal component analysis is used. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

Principal component analysis compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a constant. Another relationship between matrices is that they share principal components in common, but their eigenvalues differ. The mathematical technique used in principal component analysis is called eigenanalysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows of this matrix.

In another embodiment, the algorithm is a classifier. One type of classifier is created by "training" the algorithm with data from the training set and whose performance is evaluated with the test set data. Examples of classifiers used in conjunction with the invention are discriminant analysis, decision tree analysis, receiver operator curves or split and score analysis.

The term "classification" refers to a procedure and/or algorithm in which individual items are placed into groups or classes based on quantitative information on one or more characteristics inherent in the items (referred to as traits, variables, characters, features, etc.) and based on a statistical model and/or a training set of previously labeled items.

As use herein, the term "data set" refers to numerical values obtained from the analysis. These numerical values associated with analysis may be values such as peak height and area under the curve.

The phrase "k-nearest neighbor" refers to a classification method that classifies a point by calculating the distances between the point and points in the training data set. It then assigns the point to the class that is most common among its k-nearest neighbors (where k is an integer).

The term "FDR" used herein when performing multiple statistical tests, for example in comparing the signal between two groups in multiple data features, there is an increasingly high probability of obtaining false positive results, by random differences between the groups that can reach levels that would otherwise be considered statistically significant. In order to limit the proportion of such false discoveries, statistical significance is defined only for data features in which the differences reached a p-value (by two-sided t-test) below a threshold, which is dependent on the number of tests performed and the distribution of p-values obtained in these tests.

The term "decision tree" refers to a classifier with a flow-chart-like tree structure employed for classification. Decision trees consist of repeated splits of a data set into subsets. Each split consists of a simple rule applied to one variable, e.g., "if value of "variable 1" larger than "threshold 1"; then go left, else go right". Accordingly, the given feature space is partitioned into a set of rectangles with each rectangle assigned to one class.

The terms "test set" or "unknown" or "validation set" refer to a subset of the entire available data set consisting of those entries not included in the training set. Test data is applied to evaluate classifier performance.

The terms "training set" or "known set" or "reference set" refer to a subset of the respective entire available data set. This subset is typically randomly selected, and is solely used for the purpose of classifier construction.

"Sensitivity," as used herein, may mean a statistical measure of how well a binary classification test correctly identifies a condition, for example, how frequently it correctly classifies a sample into the correct type out of two possible types. The sensitivity for class A is the proportion of cases that are determined to belong to class "A" by the test out of the cases that are in class "A," as determined by some absolute or gold standard.

"Specificity," as used herein, may mean a statistical measure of how well a binary classification test correctly identifies a condition, for example, how frequently it correctly classifies a sample into the correct type out of two possible types. The sensitivity for class A is the proportion of cases that are determined to belong to class "not A" by the test out of the cases that are in class "not A," as determined by some absolute or gold standard.

As used herein, the term "threshold" means the numerical value assigned for each run, which reflects a statistically significant point above the calculated baseline.

Diagnostic Methods

As used herein the term "diagnosing" or "diagnosis" refers to the process of identifying a medical condition or disease (e.g., SLE) by its signs, symptoms, and in particular from the results of various diagnostic procedures, including e.g. detecting the reactivity of antibodies in a biological sample (e.g. serum) obtained from an individual, to a plurality of antigens. Furthermore, as used herein the term "diagnosing" or "diagnosis" encompasses screening for a disease, detecting a presence or a severity of a disease, distinguishing a disease from other diseases including those diseases that may feature one or more similar or identical symptoms, providing prognosis of a disease, monitoring disease progression or relapse, as well as assessment of treatment efficacy and/or relapse of a disease, disorder or condition, as well as selecting a therapy and/or a treatment for a disease, optimization of a given therapy for a disease, selecting effective dosages or schedules for administering a therapeutic product, monitoring the treatment of a disease, and/or predicting the suitability of a therapy for specific patients or subpopulations or determining the appropriate dosing of a therapeutic product in patients or subpopulations.

Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis. The "accuracy" of a diagnostic assay is the proximity of measurement results to the true value. The "p value" of a diagnostic assay is the probability of obtaining the observed sample results (or a more extreme result) when the null hypothesis is actually true.

In some embodiments, the methods of the invention are useful in diagnosing systemic lupus erythematosus (SLE) or lupus. "Lupus" as used herein is an autoimmune disease or disorder involving antibodies that attack connective tissue.

In another embodiment, the methods may result in determining a level of SLE disease activity. In a further embodiment, the methods may result in providing the comparison to an entity for monitoring SLE disease activity. In these embodiments, the methods can be used, for example, to differentiate between subjects with active disease (flare) and those with non-active disease (in remission).

In one embodiment, the subject being diagnosed according to the methods of the invention is symptomatic. In other embodiments, the subject is asymptomatic. In certain embodiments, the subject is not or was not receiving an immunosuppressive drug or an immunosuppressive treatment.

In one embodiment, the subject being diagnosed according to the methods of the invention is symptomatic. In other embodiments, the subject is asymptomatic. The diagnostic procedure can be performed in vivo or in vitro, preferably in vitro. In certain embodiments of the methods of the present invention, the diagnostic procedure is performed by non-invasive means or methods. According to some embodiments, the invention provides diagnostic methods useful for the detection of SLE or for ruling out of SLE.

The diagnostic procedure and platform of the present invention may be suitable for use as point of care device or point of service in clinic, in physician's office, in hospital laboratories, or in commercial diagnostic laboratories.

Criteria for Diagnosing Systemic Lupus Erythematosus (SLE)

The 1982 American College of Rheumatology (ACR) criteria describes features necessary to diagnose SLE. The presence of as few as 4 of the 11 criteria yields a sensitivity of 85% and a specificity of 95% for SLE. Patients with SLE may present with any combination of clinical features and serologic evidence of lupus. The ACR's criteria are (1) Serositis (pleurisy, pericarditis on examination or diagnostic ECG or imaging), (2) Oral ulcers (oral or nasopharyngeal, usually painless; palate is most specific), (3) Arthritis (non-erosive, two or more peripheral joints with tenderness or swelling), (4) Photosensitivity (unusual skin reaction to light exposure), (5) Blood disorders (leukopenia ($<4\times10^3$ cells/µL on more than one occasion), lymphopenia ($<1500$ cells/µL on more than one occasion), thrombocytopenia ($<100\times10^3$ cells/µL in the absence of offending medications), hemolytic anemia), (6) Renal involvement (proteinuria ($>0.5$ g/d or 3+ positive on dipstick testing) or cellular casts), (7) ANAs (higher titers generally more specific ($>1:160$); must be in the absence of medications associated with drug-induced lupus), (8) Immunologic phenomena (dsDNA; anti-Smith (Sm) antibodies; antiphospholipid antibodies (anticardiolipin immunoglobulin G [IgG] or immunoglobulin M [IgM] or lupus anticoagulant); biologic false-positive serologic test results for syphilis, lupus erythematosus (LE) cells (omitted in 1997)), (9) Neurologic disorder (seizures or psychosis in the absence of other causes), (10) Malar rash (fixed erythema over the cheeks and nasal bridge, flat or raised), and (11) Discoid rash (erythematous raised-rimmed lesions with keratotic scaling and follicular plugging, often scarring).

The Systemic Lupus Collaborating Clinics (SLICC) recently revised and validated the American College of Rheumatology (ACR) SLE classification criteria in order to improve clinical relevance, meet stringent methodology requirements and incorporate new knowledge in SLE immunology (Petri et al., Arthritis and Rheumatism, 2012, Vol. 64, pages 2677-2686). Seventeen criteria were identified, including 11 clinical criteria and 6 immunological criteria. The SLICC criteria for SLE classification requires fulfillment of at least four criteria, with at least one clinical criterion and one immunologic criterion, or lupus nephritis as the sole clinical criterion in the presence of ANA or anti-dsDNA antibodies.

Two of the most commonly used instruments for SLE diagnosis are the Systemic Lupus Erythematosus Disease Activity Index (SLEDAI) and the Systemic Lupus Activity Measure (SLAM).

The SLEDAI is an index that measures disease activity by weighting the importance of each organ system involved. The SLEDAI includes 24 items, representing nine organ systems. The variables are obtained by history, physical examination and laboratory assessment. Each item is weighted from 1 to 8 based on the significance of the organ involved. For example, mouth ulcers are scored as 2, while seizures are scored as 8. The laboratory parameters that are included in the SLEDAI include white blood cell count, platelet count, urinalysis, serum C3, C4 and anti-dsDNA. The total maximum score is 105. SLEDAI class definition according to the present invention: Low SLEDAI: $<=4$ ("under control"). High SLEDAI: $=>5$ The SLAM includes 32 items representing 11 organ systems. The items are scored not only as present/absent, but graded on a scale of 1 to 3 based on severity. The total possible score for the SLAM is 86. Both the SLEDAI and the SLAM have been shown to be valid, reliable, and sensitive to change over time (Liang et al. 1989, *Arth Rheum* 32:1107-18), and are widely used in research protocols and clinical trials. These indices are particularly useful for examining the value of newly proposed serologic or inflammatory markers of disease activity in SLE.

Despite the obvious utility of these instruments, there are some drawbacks. First, there is not always complete agreement between the SLAM and the SLEDAI in the same set of patients. There are several possible reasons for these discrepancies. Unlike the SLEDAI, the SLAM includes constitutional symptoms such as fatigue and fever, which may or may not be considered attributable to active SLE; this activity index relies on physician interpretation. In addition, the SLEDAI does not capture mild degrees of activity in some organ systems and does not have descriptors for several types of activity, such as hemolytic anemia.

The following examples are presented in order to more fully illustrate some embodiments of the invention. They should, in no way be construed, however, as limiting the broad scope of the invention.

EXAMPLES

Example 1

Unique Antigen-Autoantibody Reactivity Patterns Capable of Differentiating SLE Patients from Healthy Control Group Materials and Methods Human Subjects The study was approved by the Institutional Review Boards of the participating clinical unit; informed consent was obtained from all participants. All patient identifiers were kept confidential.

Serum samples were collected from 246 SLE patients from four independent sources (Albert Einstein College of Medicine, Medical University of South Carolina, Johns Hopkins University and Emory University) and were compared with sera samples of 252 healthy controls obtained from five independent sources.

To be considered an SLE patient, the following criteria had to be met: females, age 18-60 at time of sample collection, not pregnant, known demographics (age, race), medication record at time of sample collection, serum samples collected within three years of diagnosis of SLE, definitive diagnosis of SLE: ACR score >=4 (out of 11 criteria).

To be considered a healthy control, the following criteria had to be met: females, age 18-60 at time of sample collection, not pregnant, known demographics (age, race); no record of immunologically active disease, no steroid use within the past three months and no first degree relatives with SLE.

Sample Demographics

For the classifier development and verification, 196 SLE samples (average age-35) were collected from African patients (109), Hispanic patients (40) White and Caucasian patients (37), Indian/Asian/middle eastern patients (4) and others (6). 201 healthy control samples were collected from subjects with similar demographic distribution and similar average age.

For the classifier validation, 50 SLE samples (average age-40) were collected from African patients (23), Hispanic patients (9), White and Caucasian patients (15), Indian/Asian/middle eastern patient (1) and others (2). 51 healthy control samples were collected from subjects with similar demographic distribution and similar average age.

Antigen Microarrays and Serum Testing

Antigen microarray chips were prepared as previously described (Quintana et al. Lupus. 2006; 15: 428-30). Briefly, the antigens were spotted on epoxy-activated glass substrates (in-house produced epoxyhexyltriethoxysilane (EHTES) activated epoxy slides) using a Scienion S-11 non-contact microarray printer (Scienion AG, Germany). The microarrays were then blocked with 1% casein for one hour at room temperature. Test serum samples in 1% casein blocking buffer (1:20 dilution) were incubated under a coverslip for one hour at 37°. The arrays were then washed and incubated for one hour at 37° with a 1:500 dilution of two detection antibodies, mixed together: a goat anti-human IgG Cy3-conjugated antibody, and a goat anti-human IgM AF647-conjugated antibody (Jackson ImmunoResearch Laboratories Inc., West Grove, Pa.). Image acquisition was performed by laser at two wavelengths: 530 nm and 630 nm (Agilent Technologies, Santa Clara, Calif.) and the results were analyzed using Genepix pro 7 software (Molecular devices, Sunnyvale, Calif.). The quantitative range of signal intensity of binding to each antigen spot was 0-65,000; this range of detection made it possible to obtain reliable data at a 1:20 dilution of test samples.

Classifier Development and Verification

A total of 397 sera samples from SLE patients and healthy controls (HC) were tested; and 45 slides were tested with reference serum used as process control. Training was performed on a subset of 146 SLE patients and 151 healthy controls using four independent classification methods. Verification was performed on an additional set of 50 SLE patients and 50 healthy control samples.

Testing sessions: 23 test sessions were performed. 15 print batches were mixed and split for the 23 testing sessions, keeping constant ratios of SLE/HC, race, age, ACR score and sample source between the different testing sessions in order to eliminate testing bias resulting from one of these parameters. Each test session contained two print lots. SLE pool control slides were added (one slide per each print lot on each test session) as a process control and a basis for comparison between different testing sessions and print lots.

Scanning was performed on an Agilent fluorescence reader using PMT20 setting due to saturated intensities (>65,000) obtained for some of the SLE entities.

Classifier Validation

A total of 115 slides tested over 101 SLE/HC sera samples and 14 slides were used as process controls. Of the 101 sera samples tested, 50 samples were obtained from SLE patients and 51 samples were obtained from HC.

Validation testing sessions: seven test sessions were performed. Six print batches were mixed and split for the seven testing sessions, keeping constant ratios of SLE/HC, race, age and ACR score matched samples between the different testing sessions in order to eliminate testing bias resulting from one of these parameters. Each test session contained two print lots. SLE pool control slides were added (one slide per each print lot on each test session) as a process control and basis for comparison between different testing sessions and print lots. Test procedure and scanning were performed as described in the Classifier Development section.

Preprocessing

Images were extracted using Genepix Pro 7.0 with default settings and preprocessed as follows:
1. Signals were represented by spot mean intensity minus the median of the local background, followed by log (base 2) transformation for non-negative spots.
2. Negative spots were imputed by artificial low intensity values, a process performed separately for each channel.
3. The median intensities of all slides were adjusted equal to 9, for each channel separately.
4. Antigens printed in two sets (such as base iChip) were considered as two independent antigens.
   a. Antigen intensity per slide was represented by the median across all spots, excluding outlier spots and spots flagged by Genepix.

Classifier Development

Various feature selection and classifier construction methods were evaluated. The upper limit of the training accuracy (median score of bootstrapping sessions on set 1) was 88%, with several algorithm combinations reaching this level of performance. Four leading algorithms (SVM, LR, QDA, and LDA) were further considered for classifier formation.

Antigen Selection by Linear Discriminant Analysis (LDA) Algorithm

Antigens were ranked according to their selection frequency over bootstrapping iterations. The antigen list was screened in order to remove highly correlated features, i.e., Rho >=0.9. The final list includes six features, most of which were also selected by other methods, three of which are in the IgG channel and three are in the IgM channel:

TABLE 2

List of SLE related antigens having high separation capabilities identified by the LDA algorithm

| Fraction of Appearances | Antigen | Isotype |
| --- | --- | --- |
| 1 | Calf ssDNA | IgG |
| 0.793333 | U1 snRNP | IgG |
| 0.636667 | Sm | IgG |
| 0.656667 | Histone III-S | IgM |
| 0.633333 | U1 snRNP | IgM |
| 0.52 | Oligo21 | IgM |

Antigen Selection by the Quadratic Discriminant Classifier (QDA) Algorithm

Antigens were ranked according to their selection frequency over bootstrapping. The antigen list was screened in order to remove highly correlated features, i.e. Rho >=0.9. The final list includes six features, five of which are in the IgG channel and one is in IgM channel.

TABLE 3

List of SLE related antigens having high separation capabilities identified by the QDA algorithm

| Fraction of Appearances | Antigen | Isotype |
| --- | --- | --- |
| 1 | Calf ssDNA | IgG |
| 0.923333 | U1 snRNP | IgG |
| 0.996667 | H2a | IgM |
| 0.433333 | Sm | IgG |
| 0.8 | Apo-SAA | IgG |
| 0.753333 | Ro52 | IgG |

Antigen Selection by the Support Vector Machines (SVM) Algorithm

Antigens were ranked according to their average score over bootstrapping. The antigen list was screened in order to remove correlated features, i.e., Rho >=0.9. The final list includes six features, most of which were also selected by other methods, five of which are in the IgG channel and one is in IgM channel:

TABLE 4

List of SLE related antigens having high separation capabilities identified by the SVM algorithm

| Average score | Antigen | Isotype |
| --- | --- | --- |
| 0.919544 | Calf ssDNA | IgG |
| 0.477504 | Ro52 | IgG |

TABLE 4-continued

List of SLE related antigens having high separation capabilities identified by the SVM algorithm

| Average score | Antigen | Isotype |
| --- | --- | --- |
| 0.312718 | Sm | IgG |
| 0.559492 | U1 snRNP | IgG |
| 0.479361 | Histone III-S | IgM |
| 0.32738 | DNAse I | IgG |

Antigen Selection by the Logistic Regression (LR) Algorithm

Antigens were ranked according to their selection frequency over bootstrapping. The antigen list was manually screened in order to remove correlated features, i.e., Rho >=0.9. The final list includes six features, most of which were also selected by other methods, five of which are in the IgG channel and one is in the IgM channel.

TABLE 5

List of SLE related antigens having high separation capabilities identified by the LR algorithm

| Fraction of Appearances | Antigen | Isotype |
| --- | --- | --- |
| 1 | Calf ssDNA | IgG |
| 1 | U1 snRNP | IgG |
| 1 | Ro52 | IgG |
| 1 | Collagen III | IgG |
| 0.99 | Apo-SAA | IgG |
| 1 | Histone III-S | IgM |

TABLE 6

The performance of the classification methods used in the validation test

| Validation | SVM | Logistic Regression | QDA | LDA | Majority |
| --- | --- | --- | --- | --- | --- |
| AUC | 0.95 | 0.95 | 0.95 | 0.94 | |
| Sensitivity | 98% | 98% | 88% | 94% | 98% |
| Specificity | 59% | 59% | 76% | 75% | 67% |
| Accuracy | 78% | 78% | 82% | 84% | 82% |
| PPV | 70% | 70% | 79% | 78% | 74% |
| NPV | 96.7% | 97% | 87% | 93% | 97% |

As shown in FIG. 1 and Table 6, all five classification methods (SVM, LR, QDA, LDA and Majority Vote) used in the validation test allowed for the differentiation between SLE patients and healthy subjects with high sensitivity ranging between 88-98% and specificity between 59-76% using a relatively small subset of <10 SLE-specific antigens.

Figure 2:
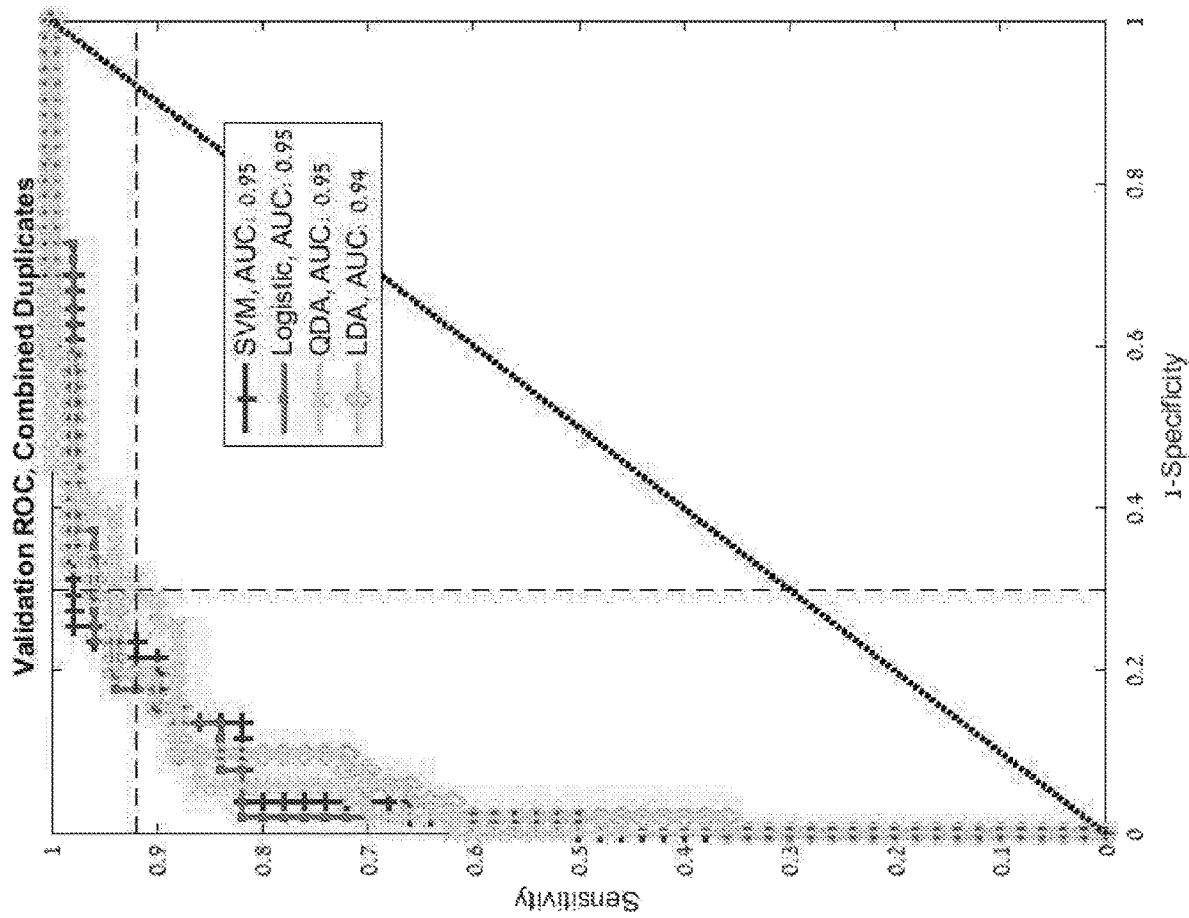
FIG. 2 demonstrates the verification of four classification methods (SVM, LR, QDA and LDA) as was performed by determining the area under the Receiver Operating Characteristics (ROC) curve for each classification method. The area under the curve (AUC) calculated were 0.95, 0.95, 0.95 and 0.94 respectively.
Figure 3:
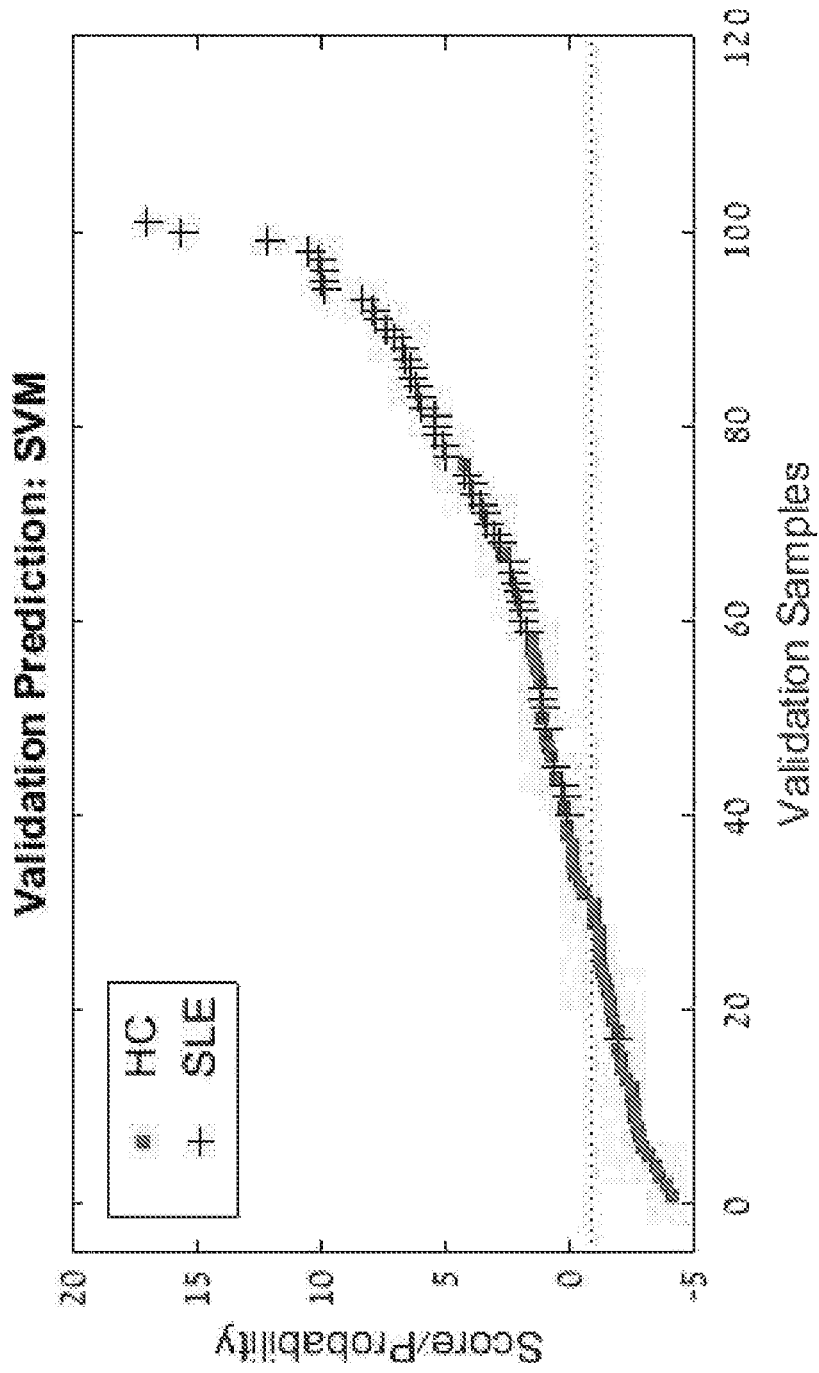
FIG. 3 demonstrates the distribution of score/probabilities (y-axis) of the validation samples (x-axis) using the SVM classifier for the separation between samples originating from healthy control (circle labeled) and samples originating from SLE patients (cross labeled). Dotted line represents the threshold.
Figure 4:
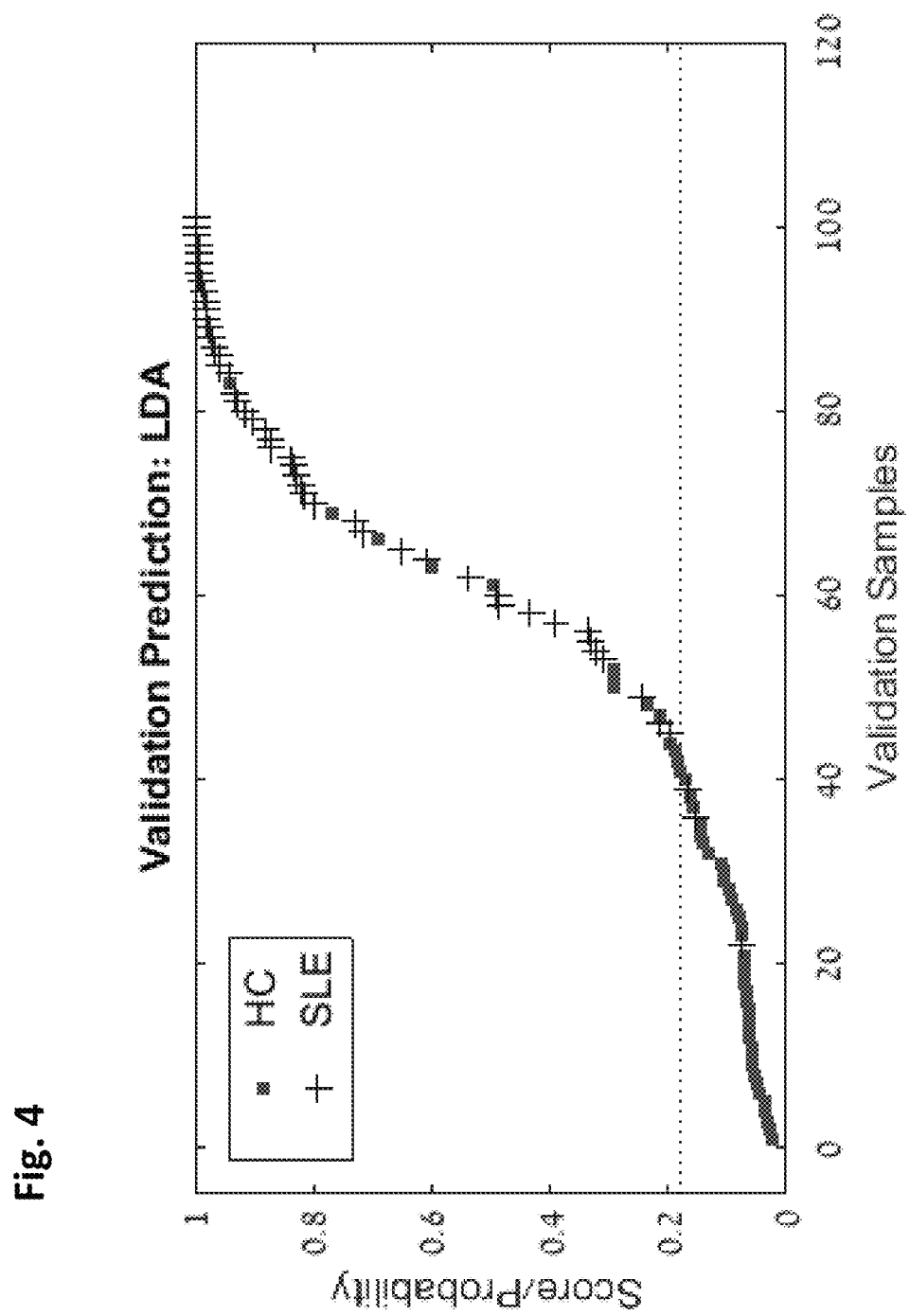
FIG. 4 demonstrates the distribution of score/probabilities (y-axis) of the validation samples (x-axis) using the LDA classifier for the separation between samples originating from healthy control (circle labeled) and samples originating from SLE patients (cross labeled). Dotted line represents the threshold.
Figure 5:
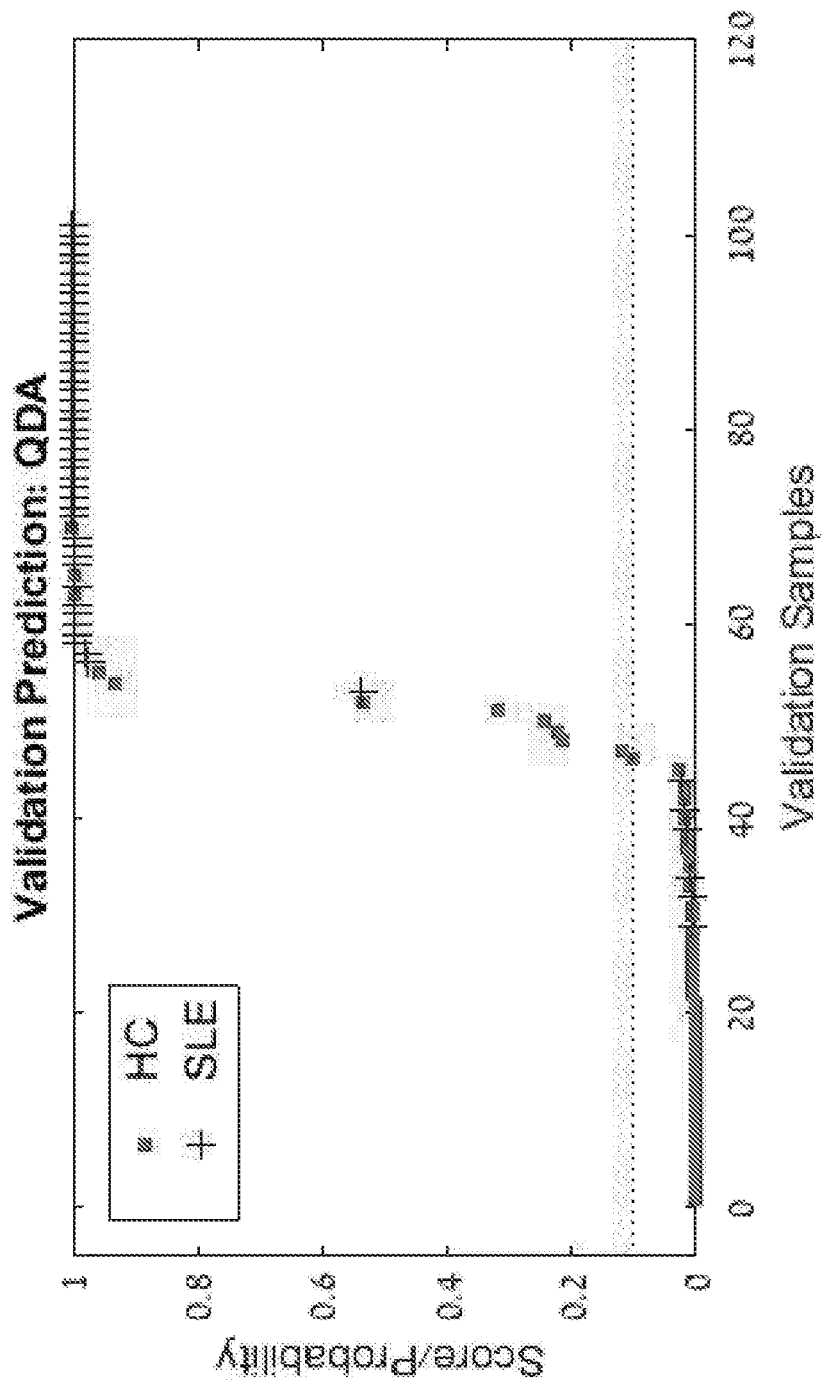
FIG. 5 demonstrates the distribution of score/probabilities (y-axis) of the validation samples (x-axis) using the QDA classifier for the separation between samples originating from healthy control (circle labeled) and samples originating from SLE patients (cross labeled). Dotted line represents the threshold.
Figure 6:
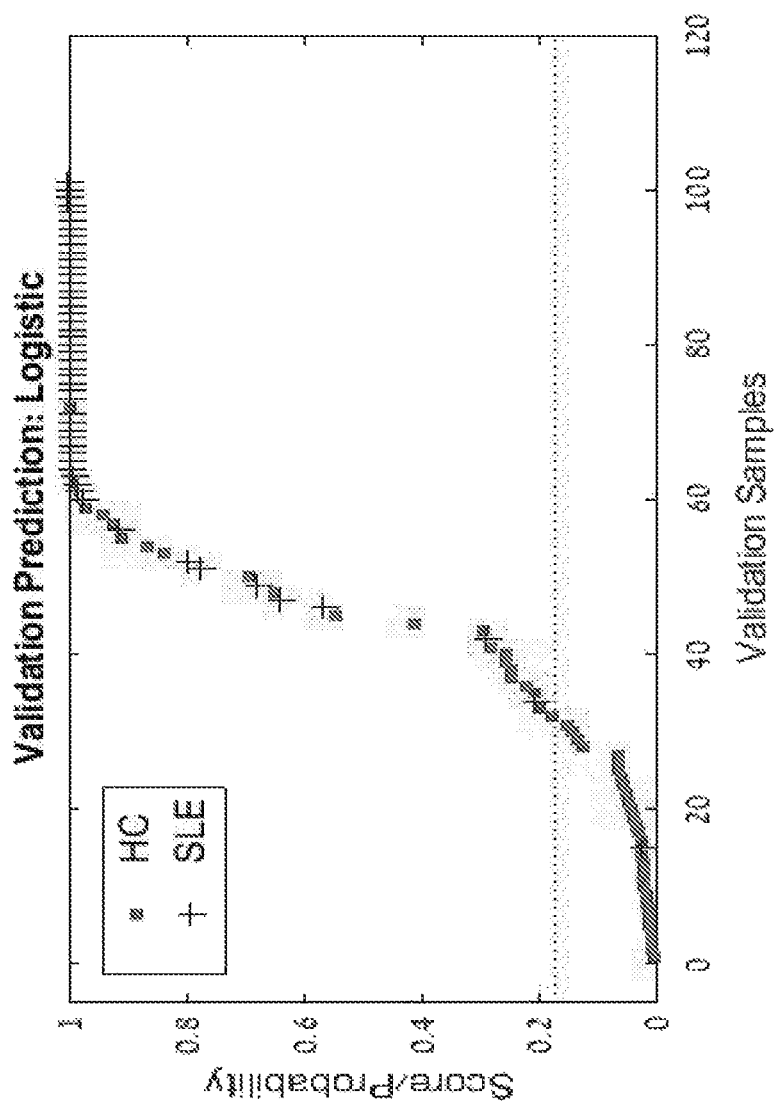
FIG. 6 demonstrates the distribution of score/probabilities (y-axis) of the validation samples (x-axis) using the LR classifier for the separation between samples originating from healthy control (circle labeled) and samples originating from SLE patients (cross labeled). Dotted line represents the threshold.

As demonstrated in FIG. 2 the verification of the four classification methods (SVM, LR, QDA and LDA) was performed by determining the area under the Receiver Operating Characteristics (ROC) curve for each method. The area under the curve (AUC) calculated were 0.95, 0.95, 0.95 and 0.94 respectively. Validation results appear in Table 6 above. Each of the different classification methods was based on subset of antigen features with some antigens being represented in all four classification methods. FIG. 3 demonstrates the distribution of score/probabilities for the validation samples using the SVM classifier between healthy control (circle labeled) and SLE patients (cross labeled) based on the antigens disclosed in Table 4. FIG. 4 demonstrates the distribution of score/probabilities for the validation samples using the LDA classifier between healthy control (circle labeled) and SLE patients (cross labeled) based on the antigens disclosed in Table 2. FIG. 5 demonstrates the distribution of score/probabilities for the validation samples using the QDA classifier between healthy control (circle labeled) and SLE patients (cross labeled) based on the antigens disclosed in Table 3. FIG. 6 demonstrates the distribution of score/probabilities for the LR validation samples using the classifier between healthy control (circle labeled) and SLE patients (cross labeled) based on the antigens disclosed in Table 5.

Example 2

Rule Out of ANA Positive Patients

Anti-nuclear antigen (ANA) testing is part of the diagnostic decision making matrix in the diagnosis of SLE. ANA testing is characterized by high false positive rate (10-20%).

In order to test whether the classification methods of the present invention can better assess potential for SLE in ANA (+) otherwise healthy-appearing patients, fluorescent ANA test (FANA) was conducted on 136 healthy control patients. 24 patients scored positive (17.6%) at a ratio greater or equal to 1:80. As shown in Table 7 the test of the present invention ruled out a diagnosis of SLE in 50-80% of ANA (+) patients. Accordingly, the Rule Out test of the present invention can exclude SLE from the diagnosis in ANA+ patients with a high degree of confidence. The Rule-Out test of the present invention can be used as a decision support tool for physicians in ruling out a diagnosis of SLE with a sensitivity of 94%, specificity of 75% and NPV of 93%. In the validation study, the inventors of the present invention were able to successfully rule out the diagnosis of SLE in up to 80% of ANA+ subjects depending on the analytic approach.

TABLE 7

The performance of the Rule Out test
24 ANA Positive Healthy Controls (>1:80)
SLE-key ®

| | | |
|---|---|---|
| SVM | Negative | 17 (71%) |
| | Positive | 7 |
| Logistic Regression | Negative | 13 (54%) |
| | Positive | 11 |
| QDA | Negative | 20 (83%) |
| | Positive | 4 |
| LDA | Negative | 16 (67%) |
| | Positive | 8 |
| Majority Vote | Negative | 18 (75%) |
| | Positive | 6 |

Figure 12:
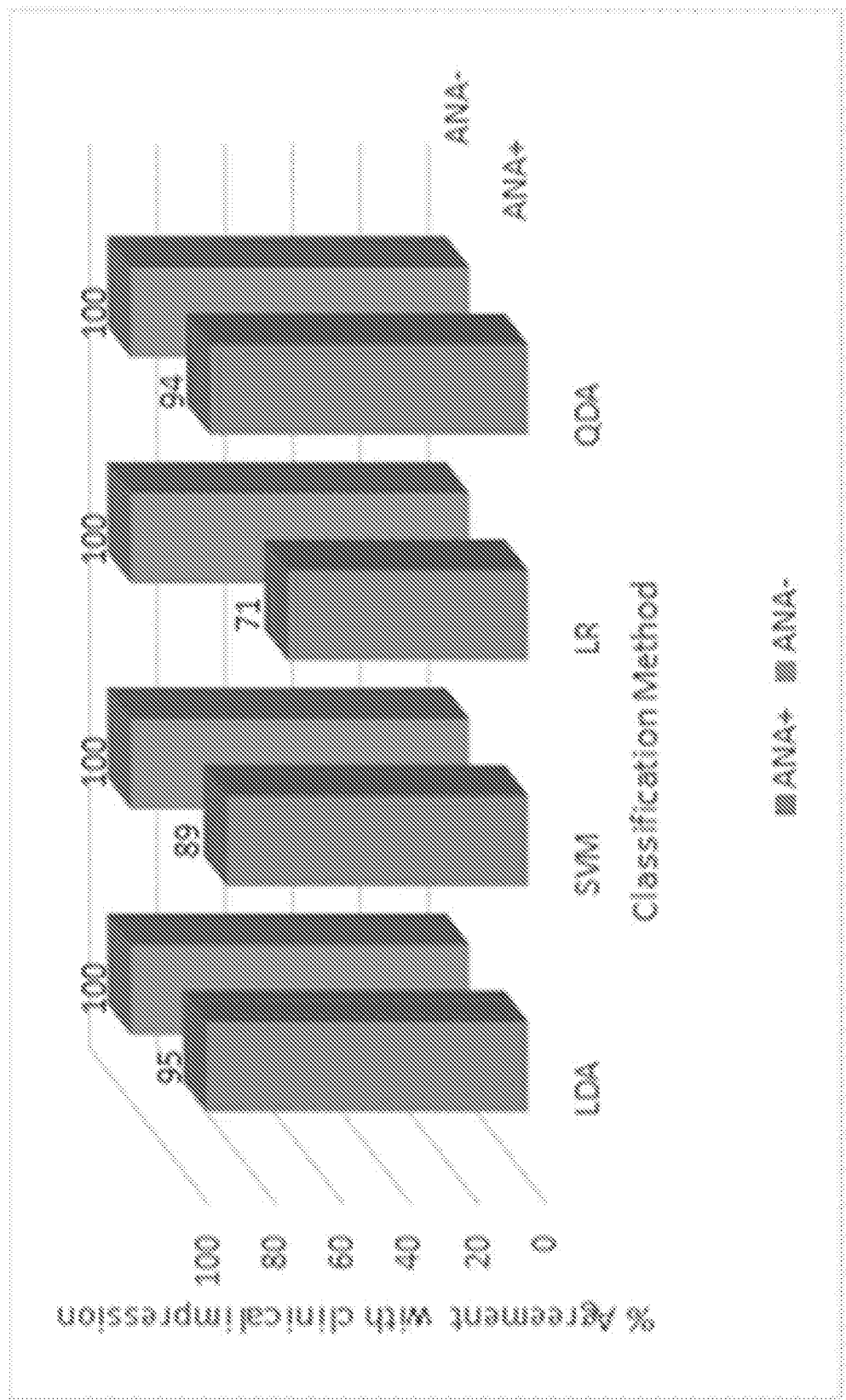
FIG. 12 demonstrates the agreement between the referring physician's clinical impression and the SLE-test results for both ANA+ and ANA− subjects, for the four classification models (SVM, LR, QDA, LDA).

As part of the diagnostic program, 154 clinical samples were evaluated with the SLE Rule-Out test. ANA test results obtained from 58 of the patients. Of these 35 were ANA+ (60%) and 23 patients were ANA− (40%). As demonstrated in FIG. 12, results of post-hoc analysis suggests that the Rule-Out test results are highly correlated with the referring rheumatologist's clinical impression for both the ANA+(up to 95% agreement) and ANA-populations (100% agreement).

Example 3

Development of Disease Activity Monitoring Test for SLE

In order to develop a model that can classify high and low disease activity (SLEDAI class) with high specificity and high confidence that the patient's disease is under control (SLEDAI<=4), three analytical stages were included: 1. Development of a classifier: feature selection by training and testing, prediction on full dataset, model evaluation and comparison. 2. Verification, applying the classifier on data from the same print-lots and evaluating performance; and 3. Validation, applying the classifier on data from different print-lots.

The analysis was performed on 382 antigen intensities (both isotypes the IgG and the IgM). Serum samples were collected from 232 female SLE patients, of which 162 (~70%) have SLEDAI<=4 and 70 (~30%) have SLEDAI=>5. The samples were obtained from four US sites: Medical University of South Carolina (MUSC), Albert Einstein College of Medicine, Johns Hopkins University and Emory University.

1. Classification:

The analysis consisted of two stages: (i) Selection of a group of antigens that evidently have a classification potential, and (ii) final classification modeling. Three classification approaches were used: classification and regression tree (CART), support vector machine (SVM) and logistic regression (LR). The first stage consisted of repeated sampling of 80% of the data. For each sampled subset, a model was fitted. The fitting procedure included sequential model reduction procedures for the logistic regression and support vector machines, which are helpful in selecting a group of antigens that are not correlated with each other and thus their contribution to the model is not redundant. For each fitting iteration, the coefficients of the antigens that were included in the model were recorded, and the value zero was assigned for those that were not included. The coefficients were averaged across all 1000 iterations, and the averages were plotted in a descending order. Such a curve decays quickly towards a low baseline level that represents the antigens with no effect. Thus only antigens of which averages appeared before the baseline region were selected for the final classification model. In the second stage, the final model for each modeling approach was obtained by fitting a model on the full dataset using only the selected antigens and the class assignment in accordance with each model was done for each observation.

2. Evaluation:

Sensitivity and specificity were used for evaluating the performance of each model and for comparing the performance between the models. The support vector machine and logistic regression models yield a probability of belonging to the high SLEDAI class for each observation. Thus for these models specificity and sensitivity are subjected to the probability threshold determined, and the collection of all their possible combinations yield an ROC curve. For model evaluation and comparison, the ROC curve of the two models was plotted and the single sensitivity-specificity combination achieved by the decision tree model was superimposed on the plot.

Figure 7:
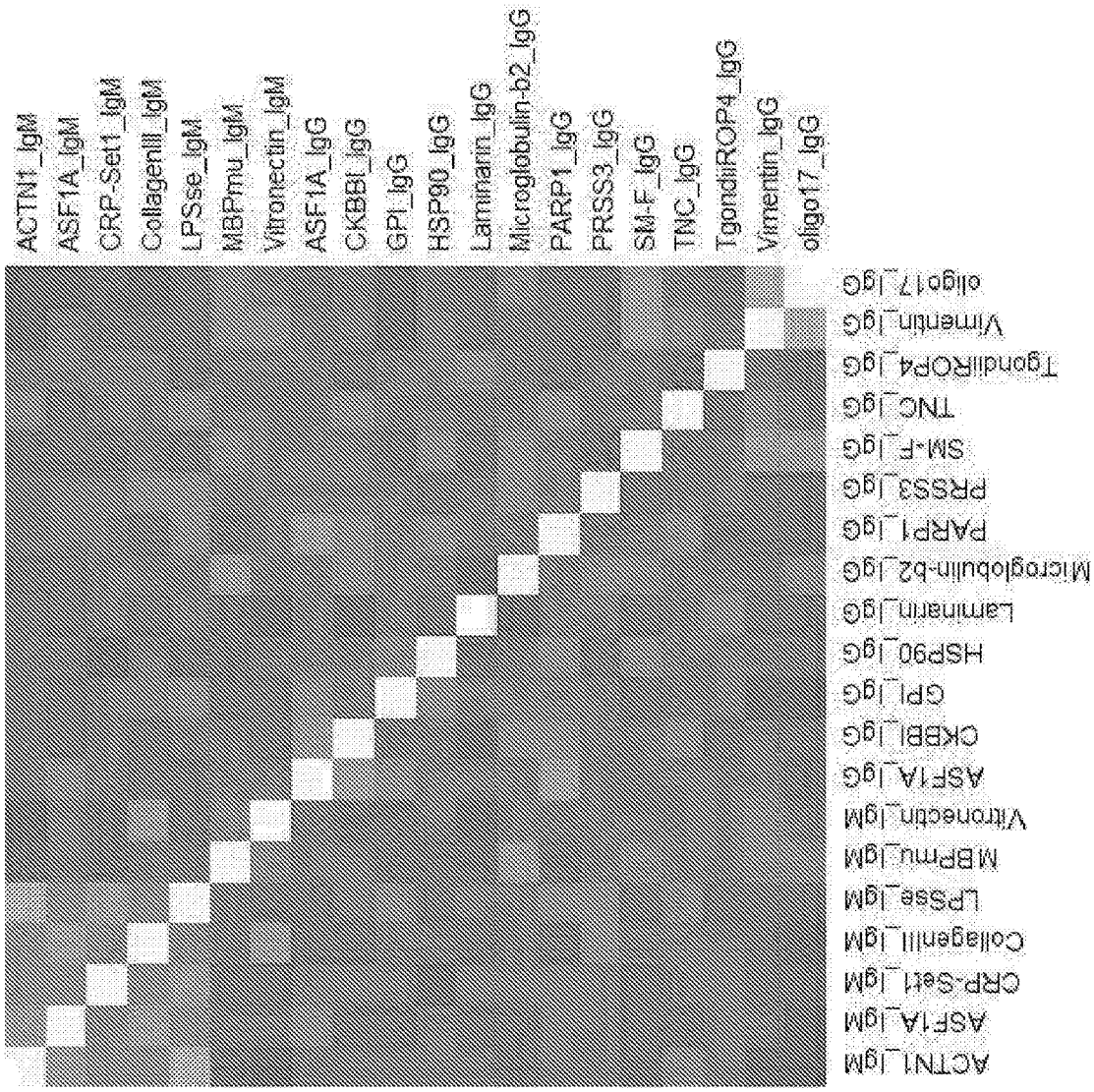
FIG. 7 demonstrates the correlation heat-map for selected antigens using the logistic regression classifier for the prediction of disease activity.
Figure 8:
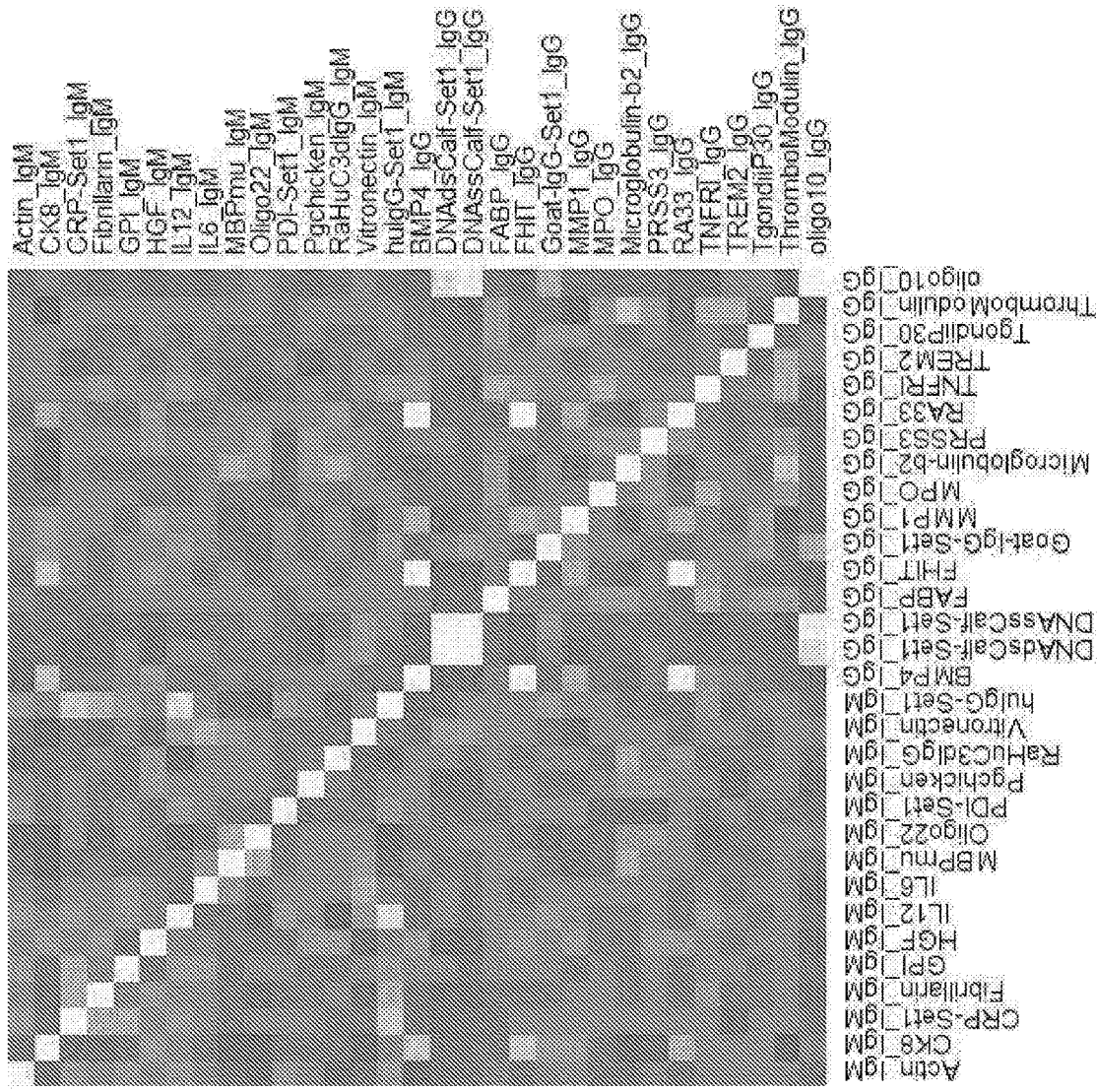
FIG. 8 demonstrates the correlation heat-map for selected antigens using the SVM classifier for the prediction of disease activity.
Figure 9:
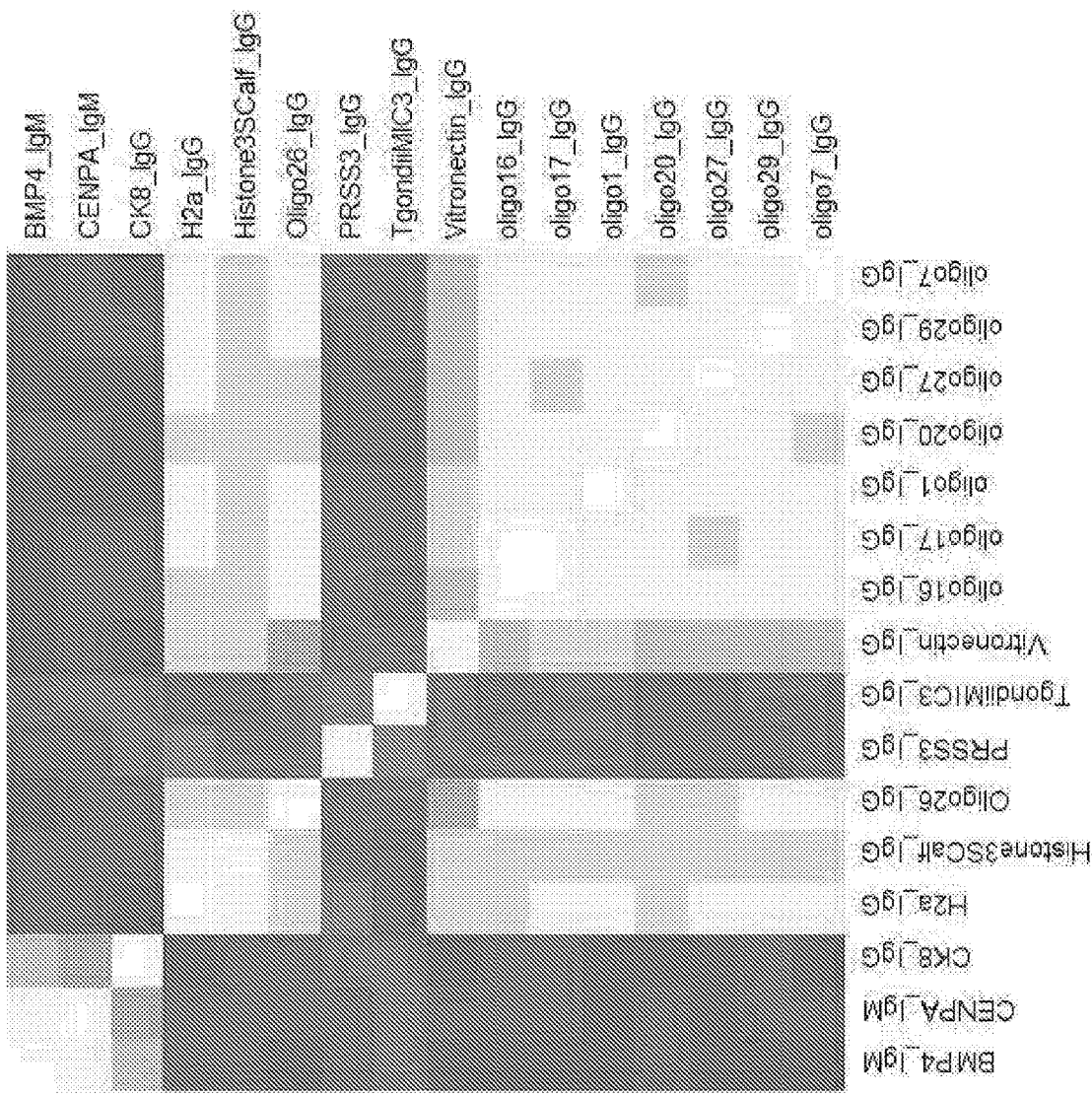
FIG. 9 demonstrates the correlation heat-map for selected antigens using the CART classifier for the prediction of disease activity.

3. Results:

a. Antigen Selection:

For the logistic regression model, 20 antigens were selected, for the SVM model 22 antigens were selected, and for the decision tree model, 16 antigens were selected. As shown in Table 8, SVM and logistic regression generated antigen lists that are relatively similar, while the decision tree model generated a list that was included antigens with an evident difference between the classes at the univariate level. However, while the antigens selected by the logistic regression and SVM models are not correlated (see the hit-maps presented in FIGS. 7 and 8), most of these antigens selected by the decision tree model are highly correlated with each other (FIG. 9).

Figure 10:
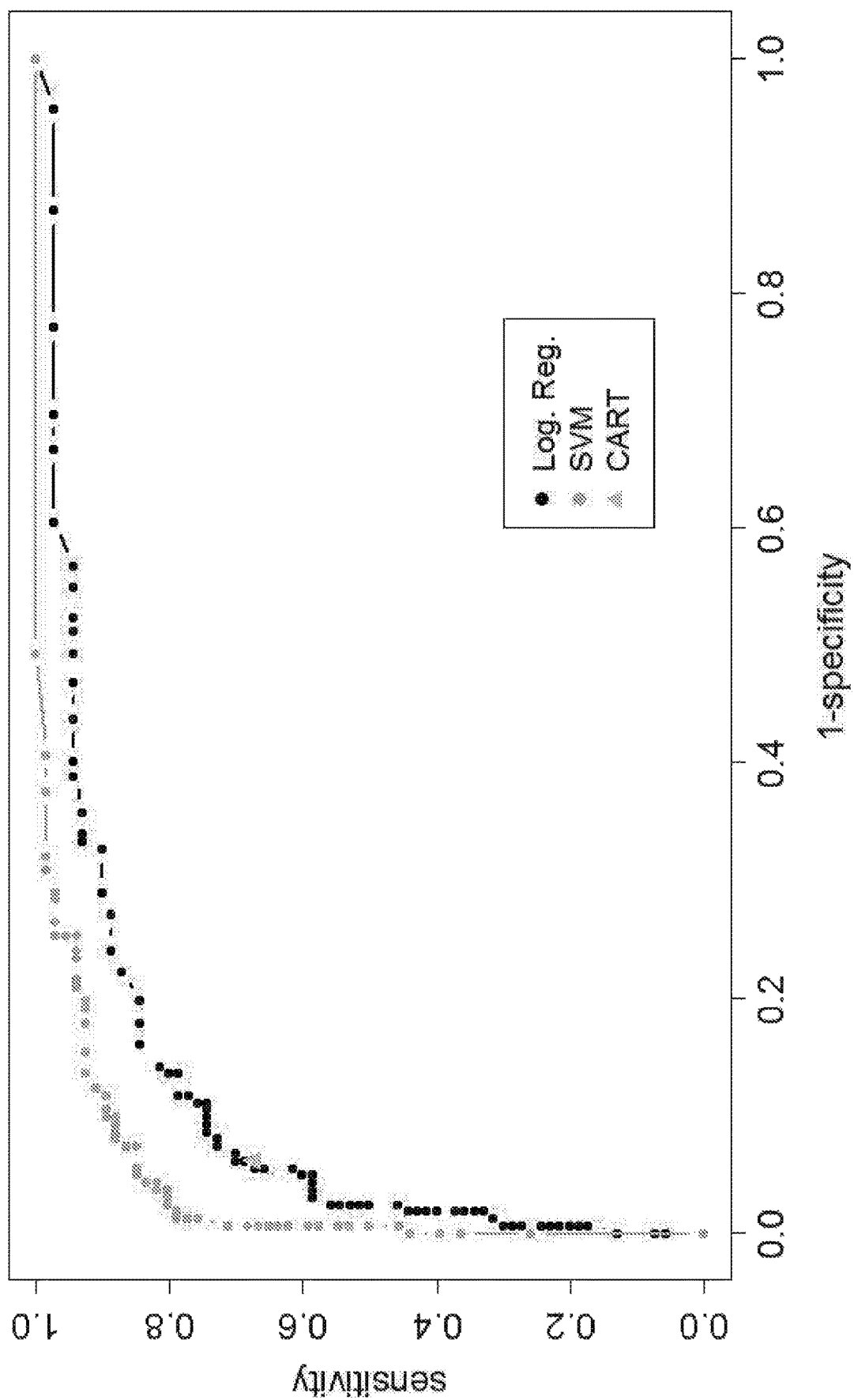
FIG. 10 demonstrates the ROC curve model performance comparison.
Figure 11:
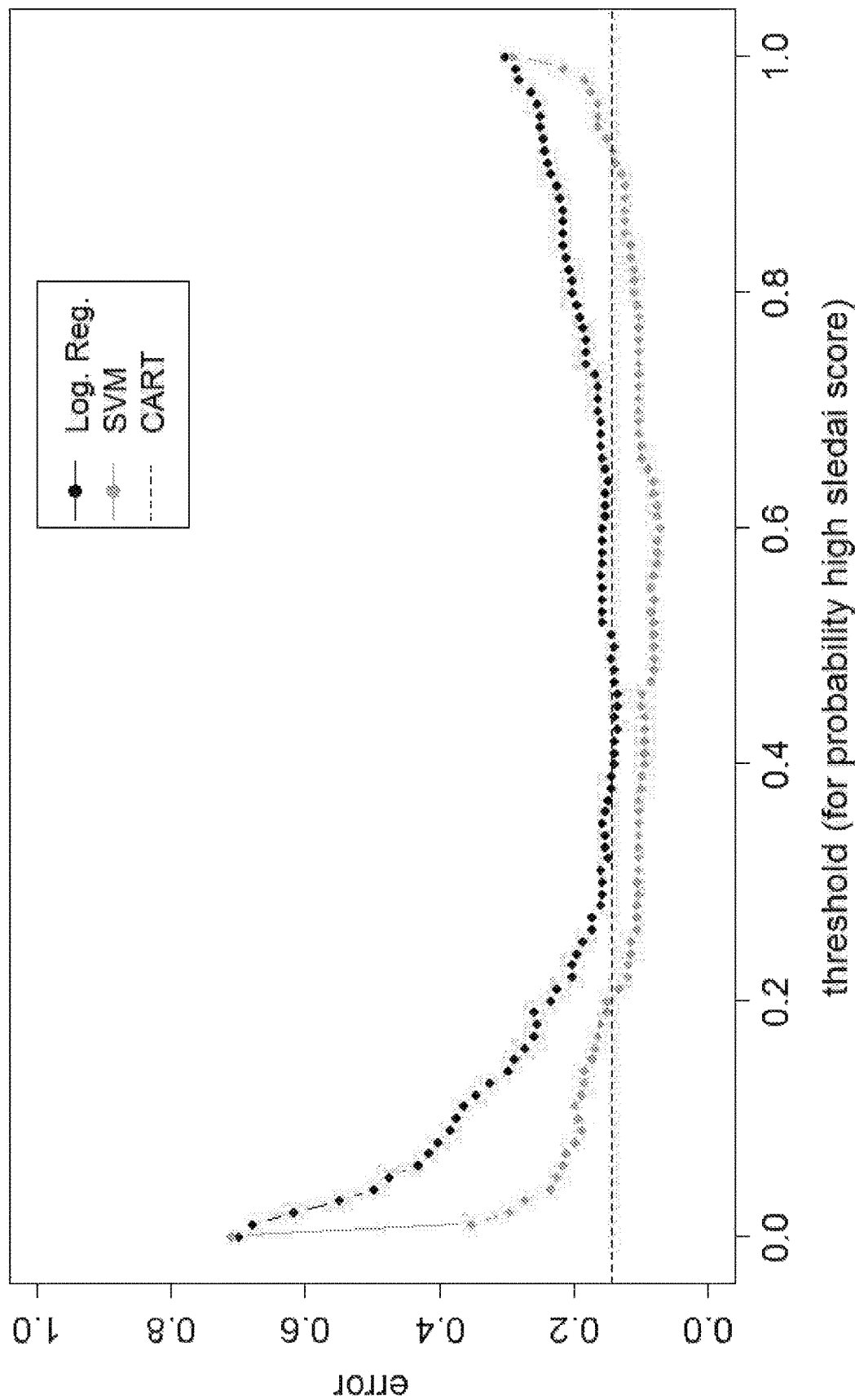
FIG. 11 demonstrates the total misclassification rate model performance comparison.

As can be seen by ROC curves shown in FIG. 10, SVM has better performance in terms of errors, compared to logistic regression, and both models outperformed the decision trees model. Considering the optimal probability threshold as the value corresponding to the minimal total error (FIG. 11), the logistic regression achieved sensitivity of 0.73 and specificity of 0.93, and the SVM model achieves sensitivity 0.89 of and specificity of 1. The decision tree model achieved sensitivity 0.67 of and specificity of 0.94

TABLE 8

List of antigens used for SLE activity monitoring test

| Classifier used | Antibody | Antigen name | full name | SEQ ID NO: | Manufacturer | cat# |
|---|---|---|---|---|---|---|
| SVM | huIgG-Set1_IgM | huIgG | huIgG | | Jacksonimmuno Reasearch | 009-000-003 |
| SVM | Gal2_IgG | Gal2 | Galectin-2 Human | 7 | Prospec | cyt-725 |
| SVM | MBPmu_IgM | MBPmu | Myelin Basic Protein from mouse | 8 | Sigma | M2941 |
| SVM | PRSS3_IgG | PRSS3 | Protease, serine, 3 | 9 | AntibodiesOnline | ABIN807 673 |
| SVM | TgondiiP30_IgG | TgondiiP30 | Toxoplasma Gondii p30 (SAG1) | 10 | Prospec | tox-264 |
| SVM | CRCP_IgM | CRCP | Calcitonin gene-related peptide-receptor component protein | 11 | Prospec | pro-919 |
| SVM | Vitronectin_IgM | Vitronectin | Serum spreading factor | 12 | Peprotech | 140-09 |
| SVM | TREM2_IgG | TREM2 | triggering receptor expressed on myeloid cells 2 | 13 | SINOBIOLOGICAL, INC | 11084-H08H |
| SVM | CK8_IgM | CK8 | Cytokeratin 8 full length | 14 | Prospec | pro-298 |
| SVM | IL12_IgM | IL12 | Interleukin-12 rh (p70) | 15 | Peprotech | 200-12 |
| SVM | CRP-Set1_IgM | CRP | C-Reactive Protein | 16 | Sigma | C4063 |
| SVM | U1 snRNP_IgM | U1 snRNP | U1 small nuclear ribonucleoprotein 70 kDa | 17 | Prospec | pro-445 |
| SVM | CENPH_IgM | CENPH | centromere protein H | 18 | Prospec | pro-966 |
| SVM | HMGB1_IgG | HMGB1 | Human high mobility group box 1 | 19 | Prospec | pro-581 |
| SVM | TPO_IgM | TPO | Thyroid Peroxidase | | Prospec | enz-285 |

TABLE 8-continued

List of antigens used for SLE activity monitoring test

| Classifier used | Antibody | Antigen name | full name | SEQ ID NO: | Manufacturer | cat# |
|---|---|---|---|---|---|---|
| SVM | Microglobulin-b2_IgG | Microglobulin-b2 | microglobulin beta2, monocyte chemoattractant protein, | 20 | Sigma | M4890 |
| SVM | HGF_IgM | HGF | Hepatocyte Growth Factor | 21 | Prospec | CYT-244 |
| SVM | DNAssCalf-Set1_IgG | DNA ss Calf | DNA single stranded | | Sigma | D8899 |
| SVM | RaHuC3dIgG_IgM | RaHuC3dIgG | Rat anti Human c3d (Isotype IgG2a) monoclonal | | USBIOLOGICAL | C0010-16C |
| SVM | TNFSF12_IgG | TNFSF12 | human TNF ligand superfamily member12 | 23 | Peprotech | 310-06 |
| SVM | Laminarin_IgG | Laminarin | Laminarin from Laminaria digitata | | Sigma | L9634 |
| SVM | HaRooster-Set1_IgG | HaRooster | Hyaluronic acid sodium salt from rooster comb | | Sigma | H5388 |
| Logistic Regression | Vitronectin_IgM | Vitronectin | Serum spreading factor | 12 | Peprotech | 140-09 |
| Logistic Regression | MBP mu_IgM | MBPmu | Myelin Basic Protein from mouse | 8 | Sigma | M2941 |
| Logistic Regression | ASF1A_IgG | ASF1A | ASF1 anti-silencing function 1 homolog 1 | 25 | Prospec | pro-682 |
| Logistic Regression | CollagenIII_IgM | CollagenIII | Collagen III (s X) | 2 | AKRONbiotech | AK9914 |
| Logistic Regression | ASF1A_IgM | ASF1A | ASF1 anti-silencing function 1 homolog 1 | 25 | Prospec | pro-682 |
| Logistic Regression | ACTN1_IgM | ACTN1 | Alpha-actinin-1 | 26 | Prospec | pro-518 |
| Logistic Regression | PRSS3_IgG | PRSS3 | Protease, serine, 3 | 9 | AntibodiesOnline | ABIN807673 |

TABLE 8-continued

List of antigens used for SLE activity monitoring test

| Classifier used | Antibody | Antigen name | full name | SEQ ID NO: | Manufacturer | cat# |
|---|---|---|---|---|---|---|
| Logistic Regression | CRP-Set1_IgM | CRP | C-Reactive Protein | 16 | Sigma | C4063 |
| Logistic Regression | Laminarin_IgG | Laminarin | Laminarin from Laminaria digitata | | Sigma | L9634 |
| Logistic Regression | Microglobulin-b2_IgG | Microglobulin-b2 | microglobulin beta2, monocyte chemoattractant protein, | 20 | Sigma | M4890 |
| Logistic Regression | HSP90_IgG | HSP90 | HSP90 bovine, Hsp90 Native Human Protein, | 6 | Sigma | H6774 |
| Logistic Regression | LPSse_IgM | LPSse | Lipopolysaccharides from Salmonella enterica serotype abortus equi purified by phenol extraction | | Sigma | L5886 |
| Logistic Regression | oligo17_IgG | oligo17 | CCATAATTGCAAAG CTTCTG (2) | 22 CCA TAA TTG CAA AGC TTC TG | SBSGenetechCo.,Ltd | n/a |
| Logistic Regression | SM-F_IgG | SM-F | small nuclear ribonucleoprotein polypeptide F | 24 | Prospec | pro-041 |
| Logistic Regression | TgondiiROP4_IgG | TgondiiROP4 | Toxoplasma Gondii ROP4 (RH2) Mosaic | 27 | Prospec | tox-266 |
| Logistic Regression | GPI_IgG | GPI | Glucose-6-Phosphate Isomerase | 28 | Prospec | enz-430 |
| Logistic Regression | CKBBI_IgG | CKBBI | Creatine kinase B chain | 29 | Prospec | CKI-268 |
| Logistic Regression | PARP1_IgG | PARP1 | Poly (ADP-Ribose) Polymerase 1 Human | 30 | Prospec | enz-477 |
| Logistic | TNC_IgG | TNC | Cardiac TrponinC | 31 | Prospec | pro-322 |

TABLE 8-continued

List of antigens used for SLE activity monitoring test

| Classifier used | Antibody | Antigen name | full name | SEQ ID NO: | Manufacturer | cat# |
|---|---|---|---|---|---|---|
| Logistic Regression | Vimentin_IgG | Vimentin | Human Vimentin from bovine lens | 32 | Peprotech | 110-10 |
| CART | Histone3SCalf_IgG | Histone3SCalf | Histone from calf thymus Type III-S | | Sigma | H5505 |
| CART | oligo17_IgG | oligo17 | CCATAATTGCAAAG CTTCTG (2) | 22 CCA TAA TTG CAA AGC TTC TG | SBSGenetechCo.,Ltd | n/a |
| CART | Olig07_IgG | Olig07 | | 33 GAG AGA GAG AGA GAG AGA GA | SBSGenetechCo.,Ltd | n/a |
| CART | CENPA_IgM | CENPA | Centromere Protein-A, rh | 34 | Prospec | pro-389 |
| CART | TgondiiMIC3_IgG | TgondiiMIC3 | Toxoplasma Gondii MIC 3 | 35 | Prospec | tox-261 |
| CART | oligo16_IgG | oligo16 | CCATAATTGCAAAC GTTCTG (1) | 36 CCA TAA TTG CAA ACG TTC TG | SBSGenetechCo.,Ltd | n/a |
| CART | Vitronectin_IgG | Vitronectin | Serum spreading factor | 12 | Peprotech | 140-09 |
| CART | PRSS3_IgG | PRSS3 | Protease, serine, 3 | 9 | AntibodiesOnline | ABIN807 673 |
| CART | Olig029_IgG | Olig029 | G9 | 37 | SBSGenetechCo.,Ltd | n/a |

TABLE 8-continued

List of antigens used for SLE activity monitoring test

| Classifier used | Antibody | Antigen name | full name | SEQ ID NO: | Manufacturer | cat# |
|---|---|---|---|---|---|---|
| | | | | GGG GGG GGG | | |
| CART | CK8_IgG | CK8 | Cytokeratin 8 full length | 14 | Prospec | pro-298 |
| CART | Oligo026_IgG | Oligo026 | T16G2 | 38 TTT TTT TTT TTT TTT TGG | SBSGenetechCo.,Ltd | n/a |
| CART | oligo1_IgG | oligo1 | A20 | 39 AAA AAA AAA AAA AA | SBSGenetechCo.,Ltd | n/a |
| CART | BMP4_IgM | BMP4 | Bone Morphogenetic protein-4,rh | 40 | Peprotech | 120-05ET |
| CART | oligo27_IgG | oligo27 | G16T1 | 41 GGG GGG GGG GGG GT | SBSGenetechCo.,Ltd | n/a |
| CART | oligo20_IgG | oligo20 | CCA TAT TCG AAA CGT TCT G (3) | 42 CCA TAA TTC GAA ACG TTC TG | SBSGenetechCo.,Ltd | n/a |

Example 4

Correlation Between SLE-Key LDA Classification Score and SLE Disease Activity Index Score In order to test whether the classification method (LDA) of the present invention can identify SLE autoantibodies profile in both active and in-active SLE patients, the correlation between SLEDAI score and the classification method (LDA) score of the present invention was tested.

The analysis was performed on 100 female SLE patients (validation set). The samples were obtained from four US sites: Medical University of South Carolina (MUSC), Albert Einstein College of Medicine, Johns Hopkins University and Emory University.

Figure 13:
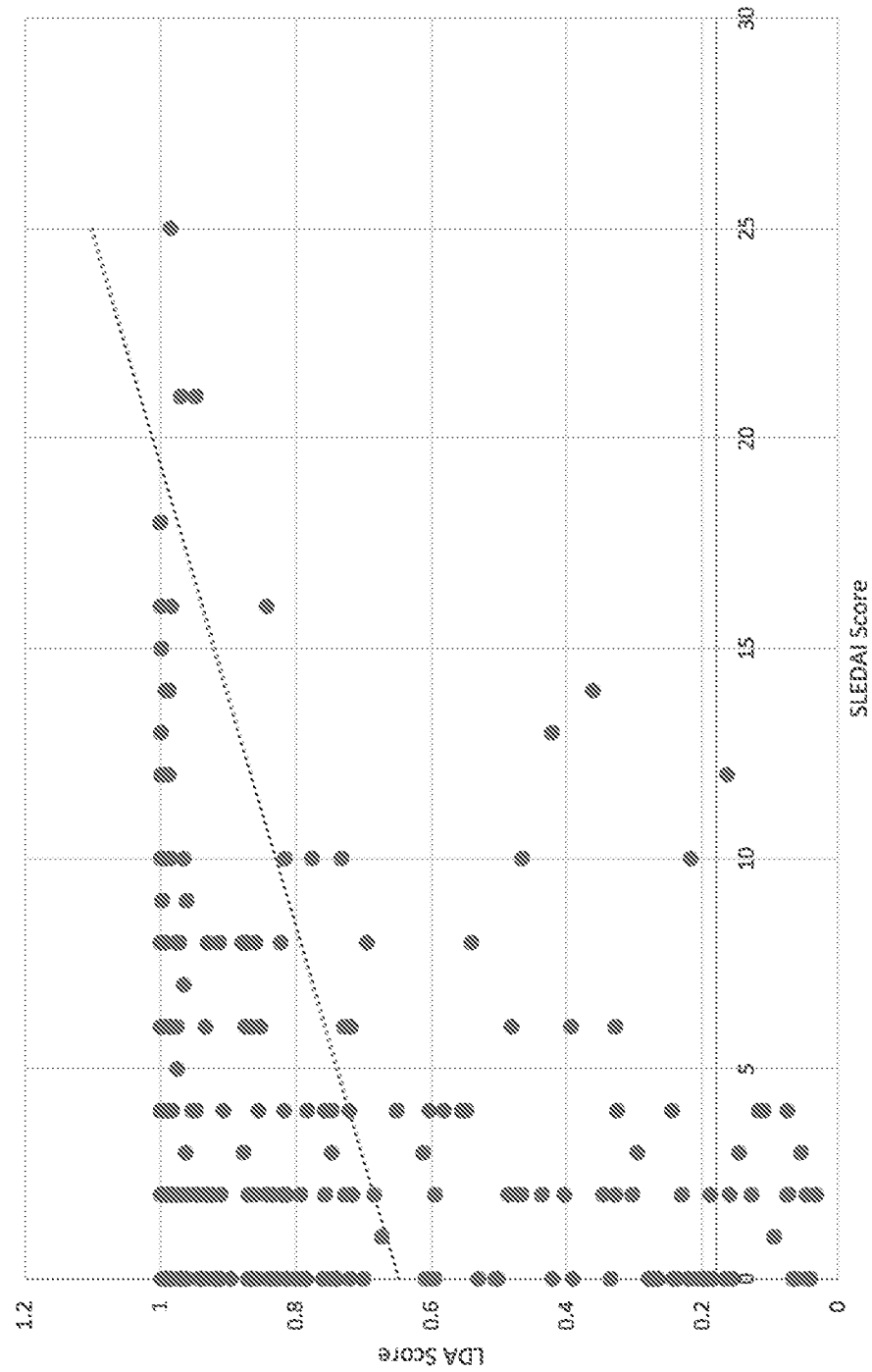
FIG. 13 demonstrates the correlation between SLE disease activity Index (SLEDAI) and LDA Score (from the validation sample set).

As shown in FIG. 13, the LDA score was correlated with the SLEDAI score. The LDA classifier score is higher for active disease state patients. Furthermore, the LDA classifier does not exclude SLE from the diagnosis for patients with an in-active disease state (i.e. SLEDAI score=0). These results suggest that the lupus autoantibodies profile is maintained in both active and in-active SLE patients and that the LDA classifier is robust and reliable in distinguishing between SLE and healthy controls autoantibodies fingerprint, regardless of the disease state.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

---

The invention claimed is:

1. A method of detecting the levels of:

IgG antibodies reactive to ssDNA, IgG antibodies reactive to U1 snRNP, and IgG antibodies reactive to Sm; and IgM antibodies reactive to Histone III-S, IgM antibodies reactive to U1 snRNP, and IgM antibodies reactive to an oligonucleotide antigen of the nucleic acid sequence TTA GGG TTA GGG TTA GGG TTA GGG (SEQ ID NO: 6, Oligo21), in a sample of a subject having or suspected of having systemic lupus erythematosus (SLE), the method comprising:

(i) obtaining a serum, plasma, or blood sample from the subject;

(ii) exposing antibodies in the sample to ssDNA, Sm, Histone III-S, U1 snRNP, and Oligo21; and (iii) detecting in the sample the levels of:

IgG antibodies reactive to ssDNA, IgG antibodies reactive to U1 snRNP and IgG antibodies reactive to Sm; and IgM antibodies reactive to Histone III-S, IgM antibodies reactive to U1 snRNP and IgM antibodies reactive to Oligo21, by quantifying the amount of antigen-antibody complex formed for each antigen, wherein the amount of antigen-antibody complex is indicative of the level of each respective antibody in said sample.

2. The method of claim 1, wherein said sample is a serum sample.

3. The method of claim 1, wherein the antigens are provided in the form of an antigen array, or an antigen chip.

* * * * *